US012779033B2

(12) United States Patent
Chandramouli et al.

(10) Patent No.: US 12,779,033 B2
(45) Date of Patent: Nov. 3, 2026

(54) EPSTEIN-BARR VIRUS MRNA VACCINES

(71) Applicant: ModernaTX, Inc., Cambridge, MA (US)

(72) Inventors: Sumana Chandramouli, Cambridge, MA (US); Brooke Bollman, Brookline, MA (US); Yen-Ting Lai, Cambridge, MA (US); Guillaume Stewart-Jones, Cambridge, MA (US); Andrea Carfi, Cambridge, MA (US)

(73) Assignee: ModernaTX, Inc., Cambridge, MA (US)

( * ) Notice: Subject to any disclaimer, the term of this patent is extended or adjusted under 35 U.S.C. 154(b) by 461 days.

(21) Appl. No.: 18/286,705

(22) PCT Filed: Apr. 13, 2022

(86) PCT No.: PCT/US2022/024530

§ 371 (c)(1),
(2) Date: Oct. 12, 2023

(87) PCT Pub. No.: WO2022/221359

PCT Pub. Date: Oct. 20, 2022

(65) Prior Publication Data

US 2024/0207392 A1 Jun. 27, 2024

Related U.S. Application Data

(60) Provisional application No. 63/174,287, filed on Apr. 13, 2021.

(51) Int. Cl.

| | |
|---|---|
| ***C07K 14/005*** | (2006.01) |
| ***A61K 9/51*** | (2006.01) |
| ***A61K 39/125*** | (2006.01) |
| ***A61K 39/245*** | (2006.01) |
| ***A61P 31/20*** | (2006.01) |
| ***A61P 37/04*** | (2006.01) |
| ***C07K 14/01*** | (2006.01) |
| ***C07K 14/05*** | (2006.01) |
| ***C12N 15/38*** | (2006.01) |
| *A61K 39/00* | (2006.01) |

(52) U.S. Cl.

CPC .......... *A61K 39/245* (2013.01); *A61K 9/5123* (2013.01); *A61P 31/20* (2018.01); *A61P 37/04* (2018.01); *A61K 2039/53* (2013.01); *A61K 2039/6018* (2013.01)

(58) Field of Classification Search

CPC .... A61K 39/125; C07K 14/005; C07K 14/01; C07K 14/03; C07K 14/05

See application file for complete search history.

(56) References Cited

U.S. PATENT DOCUMENTS

| | | | |
|---|---|---|---|
| 3,906,092 | A | 9/1975 | Hilleman et al. |
| 5,644,035 | A | 7/1997 | Koths et al. |
| 5,686,601 | A | 11/1997 | Weber |
| 5,763,573 | A | 6/1998 | McCormick et al. |
| 6,413,518 | B1 | 7/2002 | Koelle et al. |
| 6,500,419 | B1 | 12/2002 | Hone et al. |
| 6,514,948 | B1 | 2/2003 | Raz et al. |
| 6,610,044 | B2 | 8/2003 | Mathiesen |
| 7,001,890 | B1 | 2/2006 | Wagner et al. |
| 8,217,016 | B2 | 7/2012 | Hoerr et al. |
| 8,569,256 | B2 | 10/2013 | Heyes et al. |
| 8,609,142 | B2 | 12/2013 | Troiano et al. |
| 8,613,954 | B2 | 12/2013 | Zale et al. |
| 8,617,608 | B2 | 12/2013 | Zale et al. |
| 8,673,316 | B2 | 3/2014 | Kinney et al. |
| 8,691,961 | B1 | 4/2014 | Puffer et al. |
| 8,710,200 | B2 | 4/2014 | Schrum et al. |
| 8,734,832 | B2 | 5/2014 | O'Hagan et al. |
| 8,734,853 | B2 | 5/2014 | Sood et al. |
| 8,754,062 | B2 | 6/2014 | De Fougerolles et al. |
| 8,822,663 | B2 | 9/2014 | Schrum et al. |
| 8,980,864 | B2 | 3/2015 | Hoge et al. |
| 8,999,380 | B2 | 4/2015 | Bancel et al. |
| 9,000,141 | B2 | 4/2015 | Chang et al. |
| 9,221,891 | B2 | 12/2015 | Bancel et al. |
| 9,255,126 | B2 | 2/2016 | Polo et al. |
| 9,267,114 | B2 | 2/2016 | Yamshchikov et al. |
| 9,283,287 | B2 | 3/2016 | Bancel et al. |
| 9,303,079 | B2 | 4/2016 | Bancel et al. |
| 9,464,124 | B2 | 10/2016 | Bancel et al. |
| 9,512,456 | B2 | 12/2016 | Wang et al. |
| 9,533,047 | B2 | 1/2017 | de Fougerolles et al. |
| 9,572,896 | B2 | 2/2017 | Bancel et al. |
| 9,597,380 | B2 | 3/2017 | Chakraborty et al. |
| 9,675,668 | B2 | 6/2017 | Bancel et al. |
| 9,868,691 | B2 | 1/2018 | Benenato et al. |
| 9,868,692 | B2 | 1/2018 | Benenato |

(Continued)

FOREIGN PATENT DOCUMENTS

| | | | |
|---|---|---|---|
| AU | 652831 | B2 | 9/1994 |
| AU | 2015210364 | A1 | 3/2017 |

(Continued)

OTHER PUBLICATIONS

International Search Report and Written Opinion for Application No. PCT/US2022/024530, mailed Jun. 10, 2022.
[No Author Listed], "Messenger RNA", Internet: Wikipedia. Jun. 19, 2013, XP002699196, Retrieved from the Internet: URL: http://en.wikipedia.org/wiki/Messenger RNA.
[No Author Listed], Center for Drug Evaluation and Research Approval Package for New Drug Application No. 50-718/S-50 for Doxil®. Approved Dec. 28, 2015. 97 pages.

(Continued)

*Primary Examiner* — Barry A Chestnut
(74) *Attorney, Agent, or Firm* — Fish & Richardson P.C.

(57) ABSTRACT

The disclosure relates to Epstein-Barr virus ribonucleic acid vaccines as well as methods of using the vaccines and compositions comprising the vaccines.

24 Claims, 5 Drawing Sheets

Specification includes a Sequence Listing.

(56) References Cited

U.S. PATENT DOCUMENTS 9,872,900 B2 1/2018 Ciaramella et al.
9,950,068 B2 4/2018 De Fougerolles et al.
10,022,435 B2 7/2018 Ciaramella et al.
10,023,626 B2 7/2018 Bolen et al.
10,064,934 B2 9/2018 Ciaramella et al.
10,064,935 B2 9/2018 Ciaramella et al.
10,124,055 B2 11/2018 Ciaramella et al.
10,207,010 B2 2/2019 Besin et al.
10,232,055 B2 3/2019 Kariko et al.
10,273,269 B2 4/2019 Ciaramella
10,286,086 B2 5/2019 Roy et al.
10,323,076 B2 6/2019 Ellsworth et al.
10,385,088 B2 8/2019 Fraley et al.
10,449,244 B2 10/2019 Ciaramella et al.
10,465,190 B1 11/2019 Chen et al.
10,493,143 B2 12/2019 Ciaramella et al.
10,526,629 B2 1/2020 Rabideau et al.
10,653,712 B2 5/2020 Hoge
10,653,767 B2 5/2020 Ciaramella et al.
10,695,419 B2 6/2020 Ciaramella et al.
10,709,779 B2 7/2020 Ciaramella et al.
10,857,105 B2 12/2020 Benenato et al.
10,898,574 B2 1/2021 de Fougerolles et al.
10,925,958 B2 2/2021 Ciaramella
11,027,025 B2 6/2021 Hoge et al.
11,045,540 B2 6/2021 Ciaramella
11,066,355 B2 7/2021 Benenato et al.
11,103,578 B2 8/2021 Ciaramella et al.
11,174,500 B2 11/2021 Parella et al.
11,351,242 B1 6/2022 Lori et al.
11,384,352 B2 7/2022 Miracco
11,406,703 B2 8/2022 Kramarczyk et al.
11,464,848 B2 10/2022 Ciaramella et al.
11,485,960 B2 11/2022 Dousis et al.
11,497,807 B2 11/2022 Ciaramella et al.
11,564,893 B2 1/2023 Smith
11,576,961 B2 2/2023 Ciaramella et al.
11,643,441 B1 5/2023 Ciaramella et al.
11,696,946 B2 7/2023 Ciaramella
11,752,206 B2 9/2023 Ciaramella et al.
11,786,607 B2 10/2023 Hoge et al.
11,851,694 B1 12/2023 Mauger et al.
11,866,696 B2 1/2024 Issa et al.
11,872,278 B2 1/2024 Ciaramella et al.
11,905,525 B2 2/2024 Brito et al.
11,911,453 B2 2/2024 Ciaramella et al.
11,911,474 B2 2/2024 de Fougerolles et al.
11,912,982 B2 2/2024 Issa et al.
2001/0001066 A1 5/2001 Cezayirli et al.
2003/0032615 A1 2/2003 Felgner et al.
2003/0092653 A1 5/2003 Kisich et al.
2004/0005667 A1 1/2004 Ratti et al.
2005/0032730 A1 2/2005 Von Der Mulbe et al.
2005/0059624 A1 3/2005 Hoerr et al.
2005/0250723 A1 11/2005 Hoerr et al.
2006/0172003 A1 8/2006 Meers et al.
2006/0172966 A1 8/2006 Lipford et al.
2007/0280929 A1 12/2007 Hoerr et al.
2007/0292453 A1 12/2007 Floyd et al.
2008/0025944 A1 1/2008 Hoerr et al.
2008/0171711 A1 7/2008 Hoerr et al.
2009/0181044 A1 7/2009 Apt et al.
2009/0305324 A1 12/2009 Kuzushima et al.
2010/0112042 A1 5/2010 Polisky et al.
2010/0130588 A1 5/2010 Yaworski et al.
2010/0189729 A1 7/2010 Hoerr et al.
2010/0203076 A1 8/2010 Fotin-Mleczek et al.
2010/0239608 A1 9/2010 Mulbe et al.
2010/0291156 A1 11/2010 Barner et al.
2010/0303851 A1 12/2010 Hoerr et al.
2010/0305196 A1 12/2010 Probst et al.
2011/0250225 A1 10/2011 Fotin-Mleczek et al.
2011/0269950 A1 11/2011 Mulbe et al.
2011/0311472 A1 12/2011 Hoerr et al.
2012/0009221 A1 1/2012 Hoerr et al.
2012/0189700 A1 7/2012 Aguilar et al.
2012/0219573 A1 8/2012 Baumhof et al.
2012/0258046 A1 10/2012 Mutske
2012/0276209 A1 11/2012 Cullis et al.
2013/0022538 A1 1/2013 Rossi
2013/0102034 A1 4/2013 Schrum et al.
2013/0121988 A1 5/2013 Hoerr et al.
2013/0142818 A1 6/2013 Baumhof et al.
2013/0156849 A1 6/2013 De Fougerolles et al.
2013/0171241 A1 7/2013 Geall
2013/0183355 A1 7/2013 Jain et al.
2013/0189351 A1 7/2013 Geall
2013/0195867 A1 8/2013 Hoerr et al.
2013/0195967 A1 8/2013 Guild et al.
2013/0195968 A1 8/2013 Geall et al.
2013/0195969 A1 8/2013 Geall et al.
2013/0202684 A1 8/2013 Geall et al.
2013/0236533 A1 9/2013 Von Andrian et al.
2013/0236974 A1 9/2013 De Fougerolles
2013/0243848 A1 9/2013 Lobovkina et al.
2013/0245103 A1 9/2013 de Fougerolles et al.
2013/0259923 A1 10/2013 Bancel et al.
2013/0266640 A1 10/2013 De Fougerolles et al.
2013/0295043 A1 11/2013 Kallen et al.
2013/0336998 A1 12/2013 Kallen et al.
2014/0023673 A1 1/2014 Weiner et al.
2014/0037660 A1 2/2014 Folin-Mleczek et al.
2014/0065228 A1 3/2014 Yarowoski et al.
2014/0134201 A1 5/2014 Tureci et al.
2014/0147432 A1 5/2014 Bancel et al.
2014/0148502 A1 5/2014 Bancel et al.
2014/0193482 A1 7/2014 Bancel et al.
2014/0206752 A1 7/2014 Afeyan et al.
2014/0206753 A1 7/2014 Guild et al.
2014/0271829 A1 9/2014 Lilja et al.
2014/0378538 A1 12/2014 Bancel
2015/0051268 A1 2/2015 Bancel et al.
2015/0056253 A1 2/2015 Bancel et al.
2015/0141499 A1 5/2015 Bancel et al.
2015/0307542 A1 10/2015 Roy et al.
2015/0315541 A1 11/2015 Bancel et al.
2016/0024140 A1 1/2016 Issa et al.
2016/0024141 A1 1/2016 Issa et al.
2016/0032273 A1 2/2016 Shahrokh et al.
2016/0038612 A1 2/2016 Hoge et al.
2016/0194368 A1 7/2016 Hoge et al.
2016/0194625 A1 7/2016 Hoge et al.
2016/0243221 A1 8/2016 Hoge et al.
2016/0271272 A1 9/2016 Bancel et al.
2016/0303224 A1 10/2016 Kanekiyo et al.
2016/0317647 A1 11/2016 Ciaramella et al.
2016/0331828 A1 11/2016 Ciaramella et al.
2016/0361411 A1 12/2016 Gindy et al.
2016/0367658 A1 12/2016 Kinney et al.
2017/0009244 A1 1/2017 Sahin et al.
2017/0043037 A1 2/2017 Kariko et al.
2017/0065675 A1 3/2017 Bancel et al.
2017/0079916 A1 3/2017 Khan et al.
2017/0130255 A1 5/2017 Wang et al.
2017/0161635 A1 6/2017 Oona et al.
2017/0202979 A1 7/2017 Chakraborty et al.
2017/0204152 A1 7/2017 Nelson et al.
2017/0239371 A1 8/2017 Guild et al.
2017/0340724 A1 11/2017 Ciaramella et al.
2017/0340725 A1 11/2017 Ciaramella et al.
2018/0000953 A1 1/2018 Almarsson et al.
2018/0002393 A1 1/2018 Bancel et al.
2018/0028645 A1 2/2018 Ciaramella et al.
2018/0028664 A1 2/2018 Besin et al.
2018/0078634 A1 3/2018 Ogembo et al.
2018/0161422 A1 6/2018 Probst et al.
2018/0237849 A1 8/2018 Thompson
2018/0243225 A1 8/2018 Ciaramella
2018/0243230 A1 8/2018 Smith
2018/0251754 A1 9/2018 DeRosa et al.
2018/0256628 A1 9/2018 Hoge et al.
2018/0271795 A1 9/2018 Martini et al.
2018/0271970 A1 9/2018 Ciaramella et al.
2018/0273977 A1 9/2018 Mousavi et al.

(56) References Cited

U.S. PATENT DOCUMENTS

2018/0274009 A1 9/2018 Marquardt et al.
2018/0280496 A1 10/2018 Ciaramella et al.
2018/0289792 A1 10/2018 Ciaramella et al.
2018/0303929 A1 10/2018 Ciaramella et al.
2018/0311336 A1 11/2018 Ciaramella et al.
2018/0311343 A1 11/2018 Huang et al.
2018/0312549 A1 11/2018 Ciaramella
2018/0318409 A1 11/2018 Valiante et al.
2018/0363019 A1 12/2018 Hoge
2018/0369374 A1 12/2018 Frederick et al.
2018/0371047 A1 12/2018 Ticho et al.
2019/0002890 A1 1/2019 Martini et al.
2019/0008887 A1 1/2019 Mousavi et al.
2019/0008938 A1 1/2019 Ciaramella et al.
2019/0008948 A1 1/2019 Ciaramella et al.
2019/0015501 A1 1/2019 Ciaramella et al.
2019/0085368 A1 3/2019 Bancel et al.
2019/0099481 A1 4/2019 Ciaramella et al.
2019/0125839 A1 5/2019 Frederick et al.
2019/0161728 A1 5/2019 Zagury et al.
2019/0175517 A1 6/2019 Martini et al.
2019/0175727 A1 6/2019 Huang et al.
2019/0192646 A1 6/2019 Cohen et al.
2019/0192653 A1 6/2019 Hoge et al.
2019/0211065 A1 7/2019 Ciaramella
2019/0247417 A1 8/2019 Hoge et al.
2019/0275170 A1 9/2019 Benenato et al.
2019/0298657 A1 10/2019 Martini et al.
2019/0298658 A1 10/2019 Benenato
2019/0300906 A1 10/2019 Martini et al.
2019/0314292 A1 10/2019 Benenato et al.
2019/0336452 A1 11/2019 Brader
2019/0336595 A1 11/2019 Ciaramella
2019/0351040 A1 11/2019 Valiante et al.
2019/0367561 A1 12/2019 Cui et al.
2019/0382774 A1 12/2019 Hoge et al.
2019/0390181 A1 12/2019 Benenato et al.
2020/0030432 A1 1/2020 Ciaramella et al.
2020/0032274 A1 1/2020 Mauger et al.
2020/0038499 A1 2/2020 Narayanan et al.
2020/0054737 A1 2/2020 Ciaramella et al.
2020/0069599 A1 3/2020 Smith et al.
2020/0069793 A1 3/2020 Ciaramella
2020/0069794 A1 3/2020 Ciaramella et al.
2020/0071689 A1 3/2020 Miracco
2020/0085916 A1 3/2020 Martini et al.
2020/0109420 A1 4/2020 Brito et al.
2020/0129445 A1 4/2020 Patel et al.
2020/0129608 A1 4/2020 Ciaramella et al.
2020/0129615 A1 4/2020 Ciaramella et al.
2020/0131550 A1 4/2020 Rabideau et al.
2020/0163878 A1 5/2020 Baumhof et al.
2020/0164059 A1 5/2020 Mcguire et al.
2020/0172928 A1 6/2020 Yao
2020/0206362 A1 7/2020 Besin et al.
2020/0239869 A1 7/2020 Issa et al.
2020/0246453 A1 8/2020 Ciaramella et al.
2020/0254086 A1 8/2020 Hoge et al.
2020/0276295 A1 9/2020 Ogembo et al.
2020/0276296 A1 9/2020 Ciaramella et al.
2020/0282047 A1 9/2020 Ciaramella et al.
2020/0289638 A1 9/2020 Ciaramella et al.
2020/0289639 A1 9/2020 Ciaramella et al.
2020/0306191 A1 10/2020 Schariter et al.
2020/0338004 A1 10/2020 Hansson et al.
2020/0338190 A1 10/2020 Ciaramella et al.
2020/0368162 A1 11/2020 Martini
2020/0368343 A1 11/2020 Ciaramella et al.
2020/0368344 A1 11/2020 Ciaramella et al.
2020/0399322 A1 12/2020 Baumhof et al.
2021/0015896 A1 1/2021 Nabel et al.
2021/0046173 A1 2/2021 Ciaramella et al.
2021/0087135 A1 3/2021 Benenato et al.
2021/0128716 A1 5/2021 Probst et al.
2021/0145982 A1 5/2021 Hoge et al.
2021/0163919 A1 6/2021 Issa et al.
2021/0187097 A1 6/2021 Ciaramella et al.
2021/0206818 A1 7/2021 Huang et al.
2021/0217484 A1 7/2021 Giessel et al.
2021/0220467 A1 7/2021 Ciaramella et al.
2021/0228707 A1 7/2021 Mektar et al.
2021/0268086 A1 9/2021 Zhong et al.
2021/0309976 A1 10/2021 Dousis et al.
2021/0378980 A1 12/2021 Horhota et al.
2021/0395792 A1 12/2021 Rabideau et al.
2022/0031631 A1 2/2022 Almarsson et al.
2022/0047518 A1 2/2022 Hennessy et al.
2022/0054653 A1 2/2022 Martini et al.
2022/0062175 A1 3/2022 Smith et al.
2022/0062408 A1 3/2022 Kramarczyk et al.
2022/0096521 A1 3/2022 Hoge et al.
2022/0096522 A1 3/2022 Hoge et al.
2022/0096626 A1 3/2022 Ciaramella et al.
2022/0125899 A1 4/2022 Ashburn et al.
2022/0145381 A1 5/2022 Elich et al.
2022/0152178 A1 5/2022 Ciaramella et al.
2022/0175906 A1 6/2022 Ciaramella et al.
2022/0193223 A1 6/2022 Ciaramella et al.
2022/0202934 A1 6/2022 Ciaramella et al.
2022/0236253 A1 7/2022 Hopson
2022/0241399 A1 8/2022 Lusso et al.
2022/0257746 A1 8/2022 Ciaramella et al.
2022/0265857 A1 8/2022 Besin et al.
2022/0290125 A1 9/2022 Miracco
2022/0323572 A1 10/2022 Metkar et al.
2022/0347292 A1 11/2022 Panther et al.
2022/0348900 A1 11/2022 Shamashkin et al.
2022/0349006 A1 11/2022 Amato et al.
2022/0370616 A1 11/2022 Hennessy
2022/0378904 A1 12/2022 Panther et al.
2022/0401551 A1 12/2022 Kramarczyk et al.
2022/0409720 A1 12/2022 Ciaramella
2023/0000970 A1 1/2023 Nachbagauer et al.
2023/0020362 A1 1/2023 Ciaramella et al.
2023/0104080 A1 4/2023 Dousis et al.
2023/0108894 A1 4/2023 Stewart-Jones et al.
2023/0114180 A1 4/2023 Ciaramella et al.
2023/0116376 A1 4/2023 Ciaramella et al.
2023/0142529 A1 5/2023 White et al.
2023/0181481 A1 6/2023 White et al.
2023/0190761 A1 6/2023 Brader et al.
2023/0212645 A1 7/2023 Marquardt et al.
2023/0270836 A1 8/2023 Ciaramella et al.
2023/0286903 A1 9/2023 Benenato et al.
2023/0287437 A1 9/2023 Smith et al.
2023/0303632 A1 9/2023 Ciaramella et al.
2023/0310576 A1 10/2023 Ciaramella et al.
2023/0338506 A1 10/2023 Shaw et al.
2023/0346907 A1 11/2023 Ciaramella et al.
2023/0346914 A1 11/2023 Stewart-Jones et al.
2023/0355743 A1 11/2023 Stewart-Jones et al.
2023/0374079 A1 11/2023 Ciaramella et al.
2023/0381301 A1 11/2023 Ciaramella et al.
2023/0390379 A1 12/2023 Ciaramella et al.
2024/0000917 A1 1/2024 Ciaramella
2024/0100145 A1 3/2024 Bollman et al.
2024/0100151 A1 3/2024 Carfi et al.
2024/0139309 A1 5/2024 Carfi et al.
2024/0156952 A1 5/2024 Ciaramella et al.
2024/0173400 A1 5/2024 Ciaramella et al.
2024/0181030 A1 6/2024 Himansu et al.
2024/0209068 A1 6/2024 Deal et al.
2024/0216500 A1 7/2024 Nachbagauer et al.
2024/0226277 A1 7/2024 Nachbagauer et al.
2024/0229109 A1 7/2024 Rabideau et al.
2024/0285754 A1 8/2024 Stewart-Jones
2024/0293534 A1 9/2024 Stewart-Jones
2024/0299531 A1 9/2024 Stewart-Jones

(56) References Cited

U.S. PATENT DOCUMENTS

2024/0335526 A1 10/2024 Ciaramella et al.
2025/0312442 A1 10/2025 Ciaramella et al.

FOREIGN PATENT DOCUMENTS

| | | | |
|---|---|---|---|
| CA | 2473135 | | 6/2003 |
| CA | 3194325 | A1 | 5/2022 |
| CN | 108366604 | A | 8/2018 |
| CN | 113999128 | A | 2/2022 |
| DE | 10 2004 035227 | A1 | 2/2006 |
| EP | 1026253 | | 8/2000 |
| EP | 1083232 | | 2/2005 |
| EP | 1301614 | B1 | 11/2006 |
| EP | 1383556 | B1 | 10/2007 |
| EP | 1905844 | A2 | 2/2008 |
| EP | 2188379 | B1 | 1/2013 |
| EP | 2548960 | A1 | 1/2013 |
| EP | 3608308 | A | 2/2020 |
| JP | 2015-518472 | A | 7/2015 |
| JP | 2015-519346 | A | 7/2015 |
| JP | 2016-515815 | A | 6/2016 |
| JP | 2017-513956 | A | 6/2017 |
| JP | 2020-515522 | A | 5/2020 |
| JP | 2021-504445 | A | 2/2021 |
| WO | WO 1987/005326 | A1 | 9/1987 |
| WO | WO 1990/011092 | A1 | 10/1990 |
| WO | WO 1992/019752 | A1 | 11/1992 |
| WO | WO 1993/014778 | A1 | 8/1993 |
| WO | WO 1995/024485 | A2 | 9/1995 |
| WO | WO 1995/026204 | A1 | 10/1995 |
| WO | WO 1995/033835 | A1 | 12/1995 |
| WO | WO 1998/014586 | A1 | 4/1998 |
| WO | WO 1999/033982 | A2 | 7/1999 |
| WO | WO 1999/052503 | A2 | 10/1999 |
| WO | WO 2001/021810 | A1 | 3/2001 |
| WO | WO 2004/058166 | A2 | 7/2004 |
| WO | WO 2004/076645 | A1 | 9/2004 |
| WO | WO 2005/007689 | A1 | 1/2005 |
| WO | WO 2005/009346 | | 2/2005 |
| WO | WO 2005/120152 | | 12/2005 |
| WO | WO 2006/056027 | A1 | 6/2006 |
| WO | WO 2006/071903 | | 7/2006 |
| WO | WO 2006/095259 | | 9/2006 |
| WO | WO 2007/095976 | A2 | 8/2007 |
| WO | WO 2008/014979 | A3 | 2/2008 |
| WO | WO 2008/052770 | A2 | 5/2008 |
| WO | WO 2008/083949 | A2 | 7/2008 |
| WO | WO 2009/030254 | A1 | 3/2009 |
| WO | WO 2009/030481 | A1 | 3/2009 |
| WO | WO 2009/095226 | | 8/2009 |
| WO | WO 2009/127230 | A1 | 10/2009 |
| WO | WO 2010/037408 | A1 | 4/2010 |
| WO | WO 2010/037539 | A1 | 4/2010 |
| WO | WO 2010/042877 | A1 | 4/2010 |
| WO | WO 2010/054406 | A1 | 5/2010 |
| WO | WO 2010/088927 | A1 | 8/2010 |
| WO | WO 2010/115046 | A2 | 10/2010 |
| WO | WO 2011/005799 | A2 | 1/2011 |
| WO | WO 2011/026641 | A9 | 3/2011 |
| WO | WO 2011/068810 | A1 | 6/2011 |
| WO | WO 2011/069529 | A1 | 6/2011 |
| WO | WO 2011/069586 | A1 | 6/2011 |
| WO | WO 2011/144358 | A1 | 11/2011 |
| WO | WO 2011/150264 | A2 | 12/2011 |
| WO | WO 2012/006369 | A2 | 1/2012 |
| WO | WO 2012/006380 | A2 | 1/2012 |
| WO | WO 2012/019630 | A1 | 2/2012 |
| WO | WO 2012/019780 | A1 | 2/2012 |
| WO | WO 2012/075040 | A2 | 6/2012 |
| WO | WO 2012/089225 | A1 | 7/2012 |
| WO | WO 2012/113513 | A1 | 8/2012 |
| WO | WO 2012/116714 | A1 | 9/2012 |
| WO | WO 2012/116715 | A1 | 9/2012 |
| WO | WO 2012/116810 | A1 | 9/2012 |
| WO | WO 2012/116811 | A1 | 9/2012 |
| WO | WO 2012/140130 | A1 | 10/2012 |
| WO | WO 2013/006834 | A1 | 1/2013 |
| WO | WO 2013/006837 | A1 | 1/2013 |
| WO | WO 2013/006838 | A1 | 1/2013 |
| WO | WO 2013/006842 | A2 | 1/2013 |
| WO | WO 2013/030778 | A2 | 3/2013 |
| WO | WO 2013/052167 | A2 | 4/2013 |
| WO | WO 2013/055905 | A1 | 4/2013 |
| WO | WO 2013/056132 | A2 | 4/2013 |
| WO | WO 2013/059496 | A1 | 4/2013 |
| WO | WO 2013/090186 | A1 | 6/2013 |
| WO | WO 2013/090648 | A1 | 6/2013 |
| WO | WO 2013/102203 | A1 | 7/2013 |
| WO | WO 2013/113502 | A1 | 8/2013 |
| WO | WO 2013/120497 | A1 | 8/2013 |
| WO | WO 2013/120628 | A1 | 8/2013 |
| WO | WO 2013/120629 | A1 | 8/2013 |
| WO | WO 2013/174409 | A1 | 11/2013 |
| WO | WO 2013/185069 | A1 | 12/2013 |
| WO | WO 2014/071963 | A1 | 5/2014 |
| WO | WO 2014/072061 | A1 | 5/2014 |
| WO | WO 2014/089239 | A1 | 6/2014 |
| WO | WO 2014/089486 | A1 | 6/2014 |
| WO | WO 2014/127917 | A1 | 8/2014 |
| WO | WO 2014/136086 | A1 | 9/2014 |
| WO | WO 2014/144196 | A1 | 9/2014 |
| WO | WO 2014/152027 | A1 | 9/2014 |
| WO | WO 2014/152774 | A1 | 9/2014 |
| WO | WO 2014/152940 | A1 | 9/2014 |
| WO | WO 2014/159813 | A1 | 10/2014 |
| WO | WO 2014/160243 | A1 | 10/2014 |
| WO | WO 2015/013551 | A1 | 1/2015 |
| WO | WO 2015/024667 | A1 | 2/2015 |
| WO | WO 2015/024668 | A2 | 2/2015 |
| WO | WO 2015/054639 | A1 | 4/2015 |
| WO | WO 2015/164674 | A1 | 4/2015 |
| WO | WO 2015/062738 | A1 | 5/2015 |
| WO | WO 2015/130584 | A1 | 9/2015 |
| WO | WO 2015/134332 | A2 | 9/2015 |
| WO | WO 2015/189425 | A1 | 12/2015 |
| WO | WO 2016/044023 | A1 | 3/2016 |
| WO | WO 2016/092460 | A2 | 6/2016 |
| WO | WO 2016/116904 | A1 | 7/2016 |
| WO | WO 2016/149384 | A1 | 9/2016 |
| WO | WO 2016/164762 | A1 | 10/2016 |
| WO | WO 2016/176330 | A1 | 11/2016 |
| WO | WO 2016/184822 | A1 | 11/2016 |
| WO | WO 2016/201377 | A1 | 12/2016 |
| WO | WO 2016/203025 | A1 | 12/2016 |
| WO | WO 2017/011773 | A2 | 1/2017 |
| WO | WO 2017/015457 | A1 | 1/2017 |
| WO | WO 2017/015463 | A1 | 1/2017 |
| WO | WO 2017/020026 | A1 | 2/2017 |
| WO | WO 2017/021546 | A1 | 2/2017 |
| WO | WO 2017/049245 | A2 | 3/2017 |
| WO | WO 2017/062513 | A1 | 4/2017 |
| WO | WO 2017/066789 | A1 | 4/2017 |
| WO | WO 2017/070601 | A1 | 4/2017 |
| WO | WO 2017/070613 | A1 | 4/2017 |
| WO | WO 2017/070616 | A2 | 4/2017 |
| WO | WO 2017/070618 | A1 | 4/2017 |
| WO | WO 2017/070624 | A1 | 4/2017 |
| WO | WO 2017/075531 | A1 | 5/2017 |
| WO | WO 2017/109222 | | 6/2017 |
| WO | WO 2017/112865 | A1 | 6/2017 |
| WO | WO 2017/127750 | A1 | 7/2017 |
| WO | WO 2017/140905 | | 8/2017 |
| WO | WO 2017/147458 | | 8/2017 |
| WO | WO 2017/162265 | A1 | 9/2017 |
| WO | WO 2017/165317 | | 9/2017 |
| WO | WO 2017/201333 | A1 | 11/2017 |
| WO | WO 2017/201340 | A1 | 11/2017 |
| WO | WO 2017/201342 | A1 | 11/2017 |
| WO | WO 2017/201347 | A1 | 11/2017 |
| WO | WO 2017/208191 | A1 | 12/2017 |
| WO | WO 2017/210215 | | 12/2017 |
| WO | WO 2017/210364 | A1 | 12/2017 |
| WO | WO 2018/020271 | A1 | 2/2018 |
| WO | WO 2018/052549 | | 3/2018 |

(56) References Cited

FOREIGN PATENT DOCUMENTS

| | | | |
|---|---|---|---|
| WO | WO 2018/053209 | A1 | 3/2018 |
| WO | WO 2018/075980 | A1 | 4/2018 |
| WO | WO 2018/081459 | A1 | 5/2018 |
| WO | WO 2018/081462 | A1 | 5/2018 |
| WO | WO 2018/089851 | A1 | 5/2018 |
| WO | WO 2018/091540 | | 5/2018 |
| WO | WO 2018/107088 | A1 | 6/2018 |
| WO | WO 2018/111967 | A1 | 6/2018 |
| WO | WO 2018/132537 | A1 | 7/2018 |
| WO | WO 2018/140733 | A1 | 8/2018 |
| WO | WO 2018/144082 | A1 | 8/2018 |
| WO | WO 2018/144778 | A1 | 8/2018 |
| WO | WO 2018/151816 | A1 | 8/2018 |
| WO | WO 2018/157009 | A1 | 8/2018 |
| WO | WO 2018/170245 | A1 | 9/2018 |
| WO | WO 2018/170256 | A1 | 9/2018 |
| WO | WO 2018/170260 | A1 | 9/2018 |
| WO | WO 2018/170270 | A1 | 9/2018 |
| WO | WO 2018/170347 | A1 | 9/2018 |
| WO | WO 2018/175783 | A1 | 9/2018 |
| WO | WO 2018/187590 | A2 | 10/2018 |
| WO | WO 2018/200613 | A1 | 11/2018 |
| WO | WO 2018/200737 | A1 | 11/2018 |
| WO | WO 2018/232355 | A1 | 12/2018 |
| WO | WO 2018/232357 | A1 | 12/2018 |
| WO | WO 2019/018765 | A1 | 1/2019 |
| WO | WO 2019/036670 | A1 | 2/2019 |
| WO | WO 2019/036682 | A1 | 2/2019 |
| WO | WO 2019/036683 | A1 | 2/2019 |
| WO | WO 2019/036685 | A1 | 2/2019 |
| WO | WO 2019/055887 | A1 | 3/2019 |
| WO | WO 2019/103993 | A1 | 5/2019 |
| WO | WO 2019/148101 | A1 | 8/2019 |
| WO | WO 2019/161163 | A1 | 8/2019 |
| WO | WO 2019/195314 | A2 | 10/2019 |
| WO | WO 2019/195316 | A1 | 10/2019 |
| WO | WO 2020/006242 | A1 | 1/2020 |
| WO | WO 2020/056370 | A1 | 3/2020 |
| WO | WO 2020/061284 | A1 | 3/2020 |
| WO | WO 2020/061295 | A1 | 3/2020 |
| WO | WO 2020/061367 | A1 | 3/2020 |
| WO | WO 2020/097291 | A1 | 5/2020 |
| WO | WO 2020/172239 | A1 | 8/2020 |
| WO | WO 2020/185811 | A1 | 9/2020 |
| WO | WO 2020/190750 | A1 | 9/2020 |
| WO | WO 2020/243561 | A1 | 12/2020 |
| WO | WO 2021/030533 | A1 | 2/2021 |
| WO | WO 2021/050864 | A1 | 3/2021 |
| WO | WO 2021/055811 | A1 | 3/2021 |
| WO | WO 2021/155243 | A1 | 8/2021 |
| WO | WO 2021/155274 | A1 | 8/2021 |
| WO | WO 2021/159040 | A2 | 8/2021 |
| WO | WO 2021/159130 | A1 | 8/2021 |
| WO | WO 2021/211343 | A1 | 10/2021 |
| WO | WO 2021/222304 | A1 | 11/2021 |
| WO | WO 2021/231929 | A1 | 11/2021 |
| WO | WO 2021/231963 | A1 | 11/2021 |
| WO | WO 2021/237084 | A1 | 11/2021 |
| WO | WO 2021/247817 | A1 | 12/2021 |
| WO | WO 2022/032154 | A2 | 2/2022 |
| WO | WO 2022/067010 | A1 | 3/2022 |
| WO | PCT/US2022/024530 | | 6/2022 |
| WO | WO 2022/150717 | A1 | 7/2022 |
| WO | WO 2022/155524 | A1 | 7/2022 |
| WO | WO 2022/155530 | A1 | 8/2022 |
| WO | WO 2022/187698 | A1 | 9/2022 |
| WO | WO 2022/197624 | A1 | 9/2022 |
| WO | WO 2022/204491 | A1 | 9/2022 |
| WO | WO 2022/212191 | A1 | 10/2022 |
| WO | WO 2022/212442 | A1 | 10/2022 |
| WO | WO 2022/212711 | A1 | 10/2022 |
| WO | WO 2022/221335 | A1 | 10/2022 |
| WO | WO 2022/221336 | A1 | 10/2022 |
| WO | WO 2022/221359 | A1 | 10/2022 |
| WO | WO 2022/221440 | A1 | 10/2022 |
| WO | WO 2022/226277 | A1 | 10/2022 |
| WO | WO 2022/226318 | A1 | 10/2022 |
| WO | WO 2022/232585 | A1 | 11/2022 |
| WO | WO 2022/241103 | A1 | 11/2022 |
| WO | WO 2022/245888 | A1 | 11/2022 |
| WO | WO 2022/266010 | A1 | 12/2022 |
| WO | WO 2022/266012 | A1 | 12/2022 |
| WO | WO 2022/266389 | A1 | 12/2022 |
| WO | WO 2023/283642 | A1 | 1/2023 |
| WO | WO 2023/283645 | A1 | 1/2023 |
| WO | WO 2023/283651 | A1 | 1/2023 |
| WO | WO 2023/014649 | A1 | 2/2023 |
| WO | WO 2023/018773 | A1 | 2/2023 |
| WO | WO 2023/018923 | A1 | 2/2023 |
| WO | WO 2023/019181 | A1 | 2/2023 |
| WO | WO 2023/056401 | A1 | 4/2023 |
| WO | WO 2023/069625 | A1 | 4/2023 |
| WO | WO 2023/069895 | A1 | 4/2023 |
| WO | WO 2023/069900 | A1 | 4/2023 |
| WO | WO 2023/076358 | A1 | 5/2023 |
| WO | WO 2023/076658 | A1 | 5/2023 |
| WO | WO 2023/081311 | A1 | 5/2023 |
| WO | WO 2023/092069 | A1 | 5/2023 |
| WO | WO 2023/107999 | A2 | 6/2023 |
| WO | WO 2023/114307 | A1 | 6/2023 |
| WO | WO 2023/132885 | A1 | 7/2023 |
| WO | WO 2023/137149 | A1 | 7/2023 |
| WO | WO 2023/150256 | A1 | 8/2023 |
| WO | WO 2023/154818 | A1 | 8/2023 |
| WO | WO 2023/196914 | A1 | 10/2023 |
| WO | WO 2023/201204 | A1 | 10/2023 |
| WO | WO 2023/201294 | A1 | 10/2023 |
| WO | WO 2023/201296 | A1 | 10/2023 |
| WO | WO 2023/212696 | A1 | 11/2023 |
| WO | WO 2023/225524 | A1 | 11/2023 |
| WO | WO 2023/250119 | A1 | 12/2023 |
| WO | WO 2024/010993 | A1 | 1/2024 |
| WO | WO 2024/015890 | A1 | 1/2024 |
| WO | WO 2024/026005 | A1 | 2/2024 |
| WO | WO 2024/030369 | A1 | 2/2024 |
| WO | WO 2024/050483 | A1 | 3/2024 |
| WO | WO 2024/097874 | A1 | 5/2024 |
| WO | WO 2024/123978 | A1 | 6/2024 |
| WO | WO 2024/163465 | A1 | 8/2024 |

OTHER PUBLICATIONS

Ahmad et al., New multivalent cationic lipids reveal bell curve for transfection efficiency versus membrane charge density: lipid-DNA complexes for gene delivery. J Gene Med. Jun. 2005;7(6):739-48. doi: 10.1002/jgm.717.

Ahmed et al., Biochemistry, Lipids, Statpearls Publishing (2023) (https://www.ncbi.nlm.nih.gov/books/NBK525952/ (last accessed Aug. 24, 2023)).

Allen, "Government-Funded Scientists Laid the Groundwork for Billion-Dollar Vaccines" KFF Health News. Nov. 18, 2020. https://kffhealthnews.org/news/vaccine-pioneers-basic-research-scientists-laid-groundwork-for-billion-dollar-pharma-products/ (Year: 2020) ### pages.

Anderson et al., Incorporation of pseudouridine into mRNA enhances translation by diminishing PKR activation, Nucleic Acids Res. Sep. 2010;38(17):5884-92. doi: 10.1093/nar/gkq347. Epub May 10, 2010.

Arankalle, et. al. fusion protein [Henipavirus nipahense]. Gen Bank: ACT32614.1, Dep. May 2, 2011. (Year: 2011).

Archer, Induction of a T-cell specific antigen on bone marrow lymphocytes with thymus RNA. Immunology. Jan. 1978;34(1):123-9.

Ashley et al., Bone marrow-generated dendritic cells pulsed with tumor extracts or tumor RNA induce antitumor immunity against central nervous system tumors. J Exp Med. Oct. 6, 1997; 186(7): 1177-82.

Bahl et al., Preclinical and Clinical Demonstration of Immunogenicity by mRNA Vaccines against H10N8 and H7N9 Influenza Viruses. Mol Ther. Jun. 7, 2017;25(6):1316-1327. doi: 10.1016/j.ymthe.2017.03.035. Epub Apr. 27, 2017.

Bangham et al., Diffusion of univalent ions across the lamellae of swollen phospholipids. J Mol Biol. Aug. 1965;13(1):238-52. doi: 10.1016/s0022-2836(65)80093-6.

(56) References Cited

OTHER PUBLICATIONS

Bennett et al., Cholesterol enhances cationic liposome-mediated DNA transfection of human respiratory epithelial cells. Biosci Rep. Feb. 1995;15(1):47-53. doi: 10.1007/BF01200214.
Bettinger et al., Peptide-mediated RNA delivery: a novel approach for enhanced transfection of primary and post-mitotic cells. Nucleic Acids Res. Sep. 15, 2001;29(18):3882-91.
Bharali et al., Nanoparticles and cancer therapy: a concise review with emphasis on dendrimers. Int J Nanomedicine. 2009;4:1-7. Epub Apr. 1, 2009.
Bogers et al., Potent immune responses in rhesus macaques induced by nonviral delivery of a self-amplifying RNA vaccine expressing HIV type 1 envelope with a cationic nanoemulsion. J Infect Dis. Mar. 15, 2015;211(6):947-55. doi: 10.1093/infdis/jiu522. Epub Sep. 18, 2014.
Bonehill et al., Single-step antigen loading and activation of dendritic cells by mRNA electroporation for the purpose of therapeutic vaccination in melanoma patients. Clin Cancer Res. May 2009; 15(10): 3366-3375.
Borza et al., Use of gHgL for attachment of Epstein-Barr virus to epithelial cells compromises infection. J Virol. May 2004;78(10):5007-14. doi: 10.1128/jvi.78.10.5007-5014.2004.
Bose et al., Influence of cationic lipid concentration on properties of lipid-polymer hybrid nanospheres for gene delivery. Int J Nanomedicine. Sep. 2, 2015;10:5367-82. doi: 10.2147/IJN.S87120. eCollection 2015.
Brito et al., A cationic nanoemulsion for the delivery of next-generation RNA vaccines. Mol Ther. Dec. 2014;22(12):2118-29. doi: 10.1038/mt.2014.133. Epub Jul. 16, 2014.
Chahal et al., An RNA nanoparticle vaccine against Zika virus elicits antibody and CD8+ T cell responses in a mouse model. Sci Rep. Mar. 21, 2017;7(1):252. doi: 10.1038/s41598-017-00193-w.
Chattopadhyay et al., A chimeric vesiculo/alphavirus is an effective alphavirus vaccine. J Virol. Jan. 2013;87(1):395-402.
Chen et al., Influence of Particle Size on the in Vivo Potency of Lipid Nanoparticle Formulations of siRNA. J Control Release. Aug. 10, 2016;235:236-244. doi: 10.1016/j.jconrel.2016.05.059. Epub May 26, 2016.
Cheng et al., Multifunctional triblock copolymers for intracellular messenger RNA delivery. Biomaterials. Oct. 2012; 33(28): 6868-6876.
Cohen et al., Vaccine Development for Epstein-Barr Virus.Adv Exp Med Biol. 2018;1045:477-493. doi: 10.1007/978-981-10-7230-7_22.
Cohen, Epstein-barr virus vaccines. Clin Transl Immunology. Jan. 23, 2015;4(1):e32. doi: 10.1038/cti.2014.27. eCollection Jan. 2015.
Conry et al., Characterization of a messenger RNA polynucleotide vaccine vector. Cancer Res. Apr. 1, 1995 ;55 (7):1397-1400.
Cu et al., Enhanced Delivery and Potency of Self-Amplifying mRNA Vaccines by Electroporation in Situ, Vaccines, 2013, 1, 367-383. Abstract Only.
Cui et al., Rabbits immunized with Epstein-Barr virus gH/gL or GB recombinant proteins elicit higher serum virus neutralizing activity than gp350. Vaccine. Jul. 25, 2016;34(34):4050-5. doi: 10.1016/j.vaccine.2016.06.021. Epub Jun. 10, 2016.
Cullis et al., Lipid Nanoparticle Systems for Enabling Gene Therapies. Mol Ther. Jul. 5, 2017;25(7):1467-1475. doi: 10.1016/j.ymthe.2017.03.013. Epub Apr. 13, 2017.
Dahlman et al., In vivo endothelial siRNA delivery using polymeric nanoparticles with low molecular weight. Nat Nanotechnol. Aug. 2014;9(8):648-655. doi: 10.1038/nnano.2014.84. Epub May 11, 2014.
Deering et al., Nucleic acid vaccines: prospects for non-viral delivery of mRNA vaccines.Expert Opin Drug Deliv. Jun. 2014;11(6):885-99. doi: 10.1517/17425247.2014.901308. Epub Mar. 26, 2014.
Dicaro et al., In Vivo Delivery of Nucleic Acid-Formulated Microparticles as a Potential Tolerogenic Vaccine for Type 1 Diabetes. Rev Diabet Stud. 2012 Winter;9(4):348-56.
Diken et al., Current Developments in Actively Personalized Cancer Vaccination with a Focus on RNA as the Drug Format. Prog Tumor Res. 2015;42:44-54. doi: 10.1159/000437184. Epub Sep. 4, 2015. Review.
Dimitriadis et al., Translation of rabbit globin mRNA introduced by liposomes into mouse lymphocytes. Nature. Aug. 31, 1978;274(5674):923-4. doi: 10.1038/274923a0.
Dufourc, Sterols and membrane dynamics. J Chem Biol. Nov. 2008;1(1-4):63-77. doi: 10.1007/s12154-008-0010-6. Epub Sep. 23, 2008.
Durbin et al., RNAs Containing Modified Nucleotides Fail To Trigger RIG-I Conformational Changes for Innate Immune Signaling. mBio. Sep. 20, 2016;7(5):e00833-16. doi: 10.1128/mBio.00833-16.
Escalante et al., A Pentavalent Epstein-Barr Virus-Like Particle Vaccine Elicits High Titers of Neutralizing Antibodies against Epstein-Barr Virus Infection in Immunized Rabbits. Vaccines (Basel). Apr. 6, 2020;8(2):169. doi: 10.3390/vaccines8020169.
Ewert et al., Cationic liposome-nucleic acid complexes for gene delivery and silencing: pathways and mechanisms for plasmid DNA and siRNA. Top Curr Chem. 2010;296:191-226.
Murphy, Excerpts from Janeway's Immunobiology, 8th Ed. (2012). 250 pages.
Fleeton et al., Self-replicative RNA vaccines elicit protection against influenza A virus, respiratory syncytial virus, and a tickborne encephalitis virus. J Infect Dis. May 1, 2001;183(9):1395-8. Epub Mar. 30, 2001.
Geall et al., Nonviral delivery of self-amplifying RNA vaccines. Proc Natl Acad Sci U S A. Sep. 4, 2012;109(36):14604-9. doi: 10.1073/pnas.1209367109. Epub Aug. 20, 2012.
Gilboa et al., Cancer immunotherapy with mRNA-transfected dendritic cells. Immunol Rev. Jun. 2004;199:251-63.
Grabbe et al., Translating nanoparticulate-personalized cancer vaccines into clinical applications: case study with RNA-lipoplexes for the treatment of melanoma. Nanomedicine (Lond). Oct. 2016;11(20):2723-2734.
Graham et al., Novel Vaccine Technologies: Essential Components of an Adequate Response to Emerging Viral Diseases. JAMA. Apr. 10, 2018;319(14):1431-1432. doi: 10.1001/jama.2018.0345.
Guo et al., Nanoparticles escaping RES and endosome: Challenges for siRNA delivery for cancer therapy. J Nanomat. Jan. 2011;742895:1-12.
Haddad et al., Depletion of glycoprotein gp85 from virosomes made with Epstein-Barr virus proteins abolishes their ability to fuse with virus receptor-bearing cells. J Virol. Dec. 1989;63(12):4998-5005. doi: 10.1128/JVI.63.12.4998-5005.1989.
Hadinoto et al., Lipid-polymer Hybrid Nanoparticles as a New Generation Therapeutic Delivery Platform: A Review. Eur J Pharm Biopharm. Nov. 2013;85(3 Pt A):427-43. doi: 10.1016/j.ejpb.2013.07.002. Epub Jul. 17, 2013.
Hajj et al., Tools for translation: non-viral materials for therapeutic mRNA delivery. Nat Rev Mat. Sep. 2017;2:17056.
Hecker et al., Non-Viral DNA and mRNA Gene Delivery to the CNS Pre-Operatively for Neuroprotection and Following Neurotrauma. Molecular Therapy. 2004; 9, S258-S258.
Heiser et al., Induction of polyclonal prostate cancer-specific CTL using dendritic cells transfected with amplified tumor Rna. J Immunol. Mar. 1, 2001; 166(5):2953-60.
Hemmer et al., Minimal peptide length requirements for CD4(+) T cell clones—implications for molecular mimicry and T cell survival. Int Immunol. Mar. 2000;12(3):375-83. doi: 10.1093/intimm/12.3.375.
Heyes et al., Cationic lipid saturation influences intracellular delivery of encapsulated nucleic acids. J Control Release. Oct. 3, 2005;107(2):276-87.
Hoerr et al., In vivo application of RNA leads to induction of specific cytotoxic T lymphocytes and antibodies. EurJ Immunol. Jan. 2000;30(1):1-7.
Hoerr et al., Stabilized Messenger RNA (RNActiveTM) as a Tool for Innovative Gene Delivery. Tissue Engineering. Apr. 2007; 13(4): 865-925.
Hoerr, More than a messenger: A new class of drugs-mRNA-based therapeutics. Genetic Engineering & Biotechnology News. Jun. 18,

(56) References Cited

OTHER PUBLICATIONS 2013. http://www.genengnews.com/gen-articles/more-than-a-messenger-a-new-class-of-drugs-mrna-based-therapeutics/4916/ [last accessed Mar. 25, 2016].

Holtkamp et al., Modification of antigen-encoding RNA increases stability, translational efficacy, and T-cell stimulatory capacity of dendritic cells. Blood. Dec. 15, 2006;108(13):4009-17.

Hsu et al., Cationic lipid nanoparticles for therapeutic delivery of siRNA and miRNA to murine liver tumor. Nanomedicine. Nov. 2013;9(8):1169-80. doi: 10.1016/j.nano.2013.05.007. Epub May 30, 2013.

Huang et al., Asymmetric 1-alkyl-2-acyl phosphatidylcholine: a helper lipid for enhanced non-viral gene delivery. Int J Pharm. May 1, 2012;427(1):64-70. doi: 10.1016/j.ijpharm.2011.06.022. Epub Jun. 21, 2011.

Ito et al., Full-length EBNA1 mRNA-transduced dendritic cells stimulate cytotoxic T lymphocytes recognizing a novel HLA-Cw*0303- and -Cw*0304-restricted epitope on EBNA1-expressing cells.J Gen Virol. Mar. 2007;88(Pt 3):770-80.

Jirikowski et al., Reversal of diabetes insipidus in Brattleboro Rats: Intrahypothalamic injection of vasopressin mRNA. Science. Feb. 1992; 255(5047): 996-998.

Jochum et al., RNAs in Epstein-Barr virions control early steps of infection. Proc Natl Acad Sci U S A. May 22, 2012;109(21):E1396-404. doi: 10.1073/pnas.1115906109. Epub Apr. 27, 2012.

Jones et al., Long-term storage of DNA-free RNA for use in vaccine studies. Biotechniques. Nov. 2007;43(5):675-81. doi: 10.2144/000112593.

Kallen et al., A development that may evolve into a revolution in medicine: mRNA as the basis for novel, nucleotide-based vaccines and drugs. Ther Adv Vaccines. Jan. 2014;2(1):10-31. doi: 10.1177/2051013613508729.

Kallen et al., A novel, disruptive vaccination technology: self-adjuvanted RNActive(®) vaccines. Hum Vaccin Immunother. Oct. 2013;9(10):2263-76. doi: 10.4161/hv.25181. Epub Jun. 4, 2013. Review.

Kanapathipillai et al., Nanoparticle targeting of anti-cancer drugs that alter intracellular signaling or influence the tumor microenvironment. Adv Drug Deliv Rev. Dec. 15, 2014;79-80:107-18. doi: 10.1016/j.addr.2014.05.005. Epub May 9, 2014.

Kanasty et al., Delivery materials for siRNA therapeutics. Nat Mater. Nov. 2013;12(11):967-77. doi: 10.1038/nmat3765.

Kariko et al., Generating the optimal mRNA for therapy: HPLC purification eliminates immune activation and improves translation of nucleoside-modified, protein-encoding mRNA, Nucleic Acids Research, Oxford University Press, GB, vol. 39, No. 21, Sep. 2, 2011 (Sep. 2, 2011), e142. doi: 10.1093/nar/gkr695. Epub Sep. 2, 2011.

Kauffman et al., Efficacy and immunogenicity of unmodified and pseudouridine-modified mRNA delivered systemically with lipid nanoparticles in vivo. Biomaterials. Dec. 2016;109:78-87. doi: 10.1016/j.biomaterials.2016.09.006. Epub Sep. 25, 2016.

Kauffman et al., Materials for non-viral intracellular delivery of messenger RNA therapeutics. J Control Release. Oct. 28, 2016;240:227-234. doi: 10.1016/j.jconrel.2015.12.032. Epub Dec. 21, 2015.

Khanna et al., Vaccine strategies against Epstein-Barr virus-associated diseases: lessons from studies on cytotoxic T-cell-mediated immune regulation. Immunol Rev. Aug. 1999;170:49-64. doi: 10.1111/j.1600-065x.1999.tb01328.x.

Kirschner et al., Soluble Epstein-Barr virus glycoproteins gH, gL, and gp42 form a 1:1:1 stable complex that acts like soluble gp42 in B-cell fusion but not in epithelial cell fusion. J Virol. Oct. 2006;80(19):9444-54. doi: 10.1128/JVI.00572-06.

Kisich et al., Antimycobacterial agent based on mRNA encoding human beta-defensin 2 enables primary macrophages to restrict growth of *Mycobacterium tuberculosis*.Infect Immun. Apr. 2001;69(4):2692-9.

Kofler et al., Mimicking live flavivirus immunization with a non-infectious RNA vaccine. Proc. Natl. Acad. Sci. U S A. Feb. 2004;101(7):1951-1956.

Kozielski et al., Bioreducible Cationic Polymer-Based Nanoparticles for Efficient and Environmentally Triggered Cytoplasmic siRNA Delivery to Primary Human Brain Cancer Cells, ACS Nano. Apr. 22, 2014;8(4):3232-41. doi: 10.1021/nn500704t. Epub Apr. 3, 2014.

Kreiter et al., Intranodal vaccination with naked antigen-encoding RNA elicits potent prophylactic and therapeutic antitumoral immunity. Cancer Res. 2010; 70: 9031-9040.

Kreiter et al., Tumor vaccination using messenger RNA: prospects of a future therapy. Curr Opinion in Immun. Jun. 2011; 23(3): 399-406.

Kuhn et al., mRNA as a versatile tool for exogenous protein expression. Current Gene Therapy. Oct. 2012; 12 (5): 347-361.

Kwok et al., Genomic sequencing and comparative analysis of Epstein-Barr virus genome isolated from primary nasopharyngeal carcinoma biopsy. PLoS One. 2012;7(5):e36939. doi: 10.1371/journal.pone.0036939. Epub May 10, 2012.

Leitner et al., DNA and RNA-based vaccines: principles, progress and prospects. Vaccine. Dec. 10, 1999;18 (9-10):765-77.

Li et al., Application of ultra-high performace liquid chromatography for chemical characterization of liposome-based therapeutic small-interfering RNA, 13 American Pharmaceutical Review 102 (2010). ### pages.

Li et al., Overcoming obstacles to develop effective and safe siRNA therapeutics. Expert Opin Biol Ther. May 2009; 9(5): 609-19.

Lian et al., Trends and developments in liposome drug delivery systems. J Pharm Sci. Jun. 2001;90(6):667-80.

Liang et al., Efficient Targeting and Activation of Antigen-Presenting Cells In Vivo after Modified mRNA Vaccine Administration in Rhesus Macaques. Mol Ther. Dec. 6, 2017;25(12):2635-2647. doi: 10.1016/j.ymthe.2017.08.006. Epub Aug. 12, 2017.

Lindgren et al., Induction of Robust B Cell Responses after Influenza mRNA Vaccination Is Accompanied by Circulating Hemagglutinin-Specific ICOS+ PD-1+ CXCR3+ T Follicular Helper Cells. Front Immunol. Nov. 13, 2017;8:1539. doi: 10.3389/fimmu.2017.01539. eCollection 2017.

Liu et al., Influence of polyethylene glycol density and surface lipid on pharmacokinetics and biodistribution of lipid-calcium-phosphate nanoparticles. Biomaterials. Mar. 2014;35(9):3027-34. doi: 10.1016/j.biomaterials.2013.12.022. Epub Jan. 2, 2014.

Lorenzi et al., Intranasal vaccination with messenger RNA as a new approach in gene therapy: Use against tuberculosis. BMC Biotechnol. Oct. 2010; 10(77): 1-11.

Maclachlan, Lipid Nanoparticle-mediated delivery of messenger RNA. Presentation. 1st International mRNA Health Conference. Tubingen, Germany. Oct. 24, 2013. http://files.shareholder.com/downloads/ABEA-50QJTB/2628241206x0x699789/47543d12-db34-4e6e-88a9-f3ae5d97b1d2/MacLachlan_mRNA_Conf_2013.pdf. Last accessed Dec. 22, 2016.

Madden et al., Administration of nucleoside-modified mRNA encoding broadly neutralizing antibody protects humanized mice from HIV-1 challenge. Nat Commun. Mar. 2, 2017;8:14630. doi: 10.1038/ncomms14630. Available at https://acuitastx.com/wp-content/uploads/2015/01/Poster-Second-International-mRNA-Health-Conference.pdf.

Madden et al., Systemic delivery of mRNA therapeutics using lipid nanoparticles (LNP): improved potency for novel LNP and influence of route of administration on protein expression. 2nd International mRNA Health Conference. Nov. 12, 2014. https://acuitastx.com/wp-content/uploads/2015/01/Poster-Second-International-mRNA-Health-Conference.pdf. 1 page.

Magini et al., Self-Amplifying mRNA Vaccines Expressing Multiple Conserved Influenza Antigens Confer Protection against Homologous and Heterosubtypic Viral Challenge. PLoS One. Aug. 15, 2016;11(8):e0161193. doi: 10.1371/journal.pone.0161193. eCollection 2016.

Maier et al., Biodegradable Lipids Enabling Rapidly Eliminated Lipid Nanoparticles for Systemic Delivery of RNAi Therapeutics. Mol Ther. Aug. 2013; 21(8): 1570-1578.

Martinon et al., Induction of virus-specific cytotoxic T lymphocytes in vivo by liposome-entrapped mRNA. EurJ Immunol. Jul. 1993;23(7):1719-22.

Mckenzie et al., Nucleic acid vaccines: tasks and tactics. Immunol Res. 2001;24(3):225-44.

(56) References Cited

OTHER PUBLICATIONS

Midoux et al., Lipid-based mRNA vaccine delivery systems. Expert Rev Vaccines. Feb. 2015;14(2):221-34. doi: 10.1586/14760584.2015.986104. Epub Dec. 26, 2014. Review.
Mitchell et al., RNA transfected dendritic cells as cancer vaccines. Curr Opin Mal Ther. Apr. 2000;2(2):176-81.
Mitchell et al., RNA-transfected dendritic cells in cancer immunotherapy. J Clin Invest. Nov. 2000;106 (9):1065-9.
Mockey et al., mRNA-based cancer vaccine: prevention of B16 melanoma progression and metastasis by systemic injection of MART1 mRNA histidylated lipopolyplexes, Cancer Gene Therapy, 2007, 14, pp. 802-814.
Molesworth et al., Epstein-Barr virus gH is essential for penetration of B cells but also plays a role in attachment of virus to epithelial cells. J Virol. Jul. 2000;74(14):6324-32. doi: 10.1128/jvi.74.14.6324-6332.2000.
Muller et al., Transfection of dendritic cells with RNA induces CD4- and COB-mediated T cell immunity against breast carcinomas and reveals the immunodominance of presented T cell epitopes. J Immunol. Jun. 15, 2003;170 (12):5892-6.
Ostro et al., Evidence for translation of rabbit globin mRNA after liposome-mediated insertion into a human cell line. Nature. Aug. 31, 1978;274(5674):921-3. doi: 10.1038/274921a0.
Pardi et al., Expression Kinetics of Nucleoside-Modified mRNA Delivered in Lipid Nanoparticles to Mice by Various Routes. J Control Release. Nov. 10, 2015;217:345-51. doi: 10.1016/j.jconrel.2015.08.007. Epub Aug. 8, 2015.
Parisien et al., Rationalization and prediction of selective decoding of pseudouridine-modified nonsense and sense codons. RNA. Mar. 2012;18(3):355-67. doi: 10.1261/rna.031351.111. Epub Jan. 26, 2012.
Peabody et al., Termination-reinitiation occurs in the translation of mammalian cell mRNAs. Mol Cell Biol. Jul. 1986;6(7):2695-703. doi: 10.1128/mcb.6.7.2695-2703.1986.
Peek et al., Nanotechnology in vaccine delivery. Adv Drug Deliv Rev. May 22, 2008;60(8):915-28. doi: 10.1016/j.addr.2007.05.017. Epub Feb. 7, 2008.
Perez et al. Novel Epstein-Barr virus-like particles incorporating gH/gL-EBNA1 or GB-LMP2 induce high neutralizing antibody titers and EBV-specific T-cell responses in immunized mice. Oncotarget. Mar. 21, 2017;8(12):19255-19273. doi: 10.18632/oncotarget.13770.
Petsch et al., Protective efficacy of in vitro synthesized, specific mRNA vaccines against influenza A virus infection. Nat Biotechnol. Dec. 2012;30(12):1210-6. doi: 10.1038/nbt.2436. Epub Nov. 25, 2012.
Phua et al., Messenger RNA (mRNA) nanoparticle tumour vaccination. Nanoscale. Jul. 21, 2014;6(14):7715-29. doi: 10.1039/c4nr01346h. Review.
Pollard et al., Type I IFN counteracts the induction of antigen-specific immune responses by lipid-based delivery of mRNA vaccines. Mol Ther. Jan. 2013; 21 (1): 251-259.
Pulford et al., Liposome-siRNA-peptide complexes cross the blood-brain barrier and significantly decrease PrP'C on neuronal cells and PrP'RES in infected cell cultures. PLoS ONE. 201 O; 5(6): e11085.
Rabinovich et al., Synthetic messenger RNA as a tool for gene therapy. Hum. Gene Ther. Oct. 2006; 17: 1027-1035.
Reichmuth et al., mRNA Vaccine Delivery Using Lipid Nanoparticles. Ther Deliv. 2016;7(5):319-34. doi: 10.4155/tde-2016-0006.
Rittig et al., Intradermal vaccinations with RNA coding for TAA generate CD8+ and CD4+ immune responses and induce clinical benefit in vaccinated patients. Mol Ther. May 2011;19(5):990-9. doi: 10.1038/mt.2010.289. Epub Dec. 28, 2010.
Sathiyamoorthy et al., Inhibition of EBV-mediated membrane fusion by anti-gHgL antibodies. Proc Natl Acad Sci U S A. Oct. 10, 2017;114(41):E8703-E8710. doi: 10.1073/pnas.1704661114. Epub Sep. 22, 2017.
Schirrmacher et al., Intra-pinna anti-tumor vaccination with self-replicating infectious RNA or with DNA encoding a model tumor antigen and a cytokine. Gene Ther. Jul. 2000;7(13):1137-47.
Schmitt et al., In vitro induction of a bladder cancer-specific T-cell response by mRNA-transfected dendritic cells. J Cancer Res Clin Oncol. 2001 ;127(3):203-6.
Schott et al., Viral and non-viral approaches for transient delivery of mRNA and proteins. Current Gene Ther. 2011; 11 (5): 382-398.
Schwendener, Liposomes as vaccine delivery systems: a review of the recent advances. Ther Adv Vaccines. Nov. 2014;2(6):159-82. doi: 10.1177/2051013614541440.
Segura et al., Monitoring gene therapy by external imaging of mRNA: Pilot study on murine erythropoietin. Ther Drug Monit. Oct. 2007; 29(5): 612-8.
Sharifah, et al. Glycoprotein [Henipavirus nipahense]. GenBank: ADN51995.1, Dep. Sep. 27, 2010. (Year: 2010).
Shidhadye et al., Solid lipid nanoparticles and nanostructured lipid carriers—innovative generations of solid lipid carriers. Curr Drug Deliv. Oct. 2008;5(4):324-31. doi: 10.2174/156720108785915087.
Smits et al. RNA-based gene transfer for adult stem cells and T cells. Leukemia. 2004; 18: 1898-1902.
Sohn et al., In-vivo particle mediated delivery of mRNA to mammalian tissues: ballistic and biological effects. Wound Rep and Regen. Jul.-Aug. 2001; 287-296.
Sohn et al., Measurement of CD8+ and CD4+ T Cell Frequencies Specific for EBV LMP1 and LMP2a Using mRNA-Transfected DCs.PLoS One. May 29, 2015;10(5):e0127899. doi: 10.1371/journal.pone.0127899. eCollection 2015.
Strong et al., Incorporation of beta-globin untranslated regions into a Sindbis virus vector for augmentation of heterologous mRNA expression. Gene Ther. Jun. 1997;4(6):624-7.
Su et al., Antigen presenting cells transfected with LMP2a RNA induce CD4+ LMP2a-specific cytotoxic T lymphocytes which kill via a Fas-independent mechanism.Leuk Lymphoma. Aug. 2002;43(8):1651-62.
Sullenger et al., Emerging clinical applications of RNA. Nature. Jul. 11, 2002;418(6894):252-8.
Tavernier et al., mRNA as gene therapeutic: How to control protein expression. J. of Controlled Release. Mar. 2011; 150(3): 238-247.
Taylor et al., Therapeutic vaccination strategies to treat nasopharyngeal carcinoma. Chin Clin Oncol. Apr. 2016;5(2):23. doi: 10.21037/cco.2016.03.20.
Tekmira, Lipid Nanoparticle-mediated delivery of messenger RNA (retrieved from the internet). Published Oct. 24, 2013. Available at http://files.shareholder.com/downloads/ABEA-50QJTB/2628241206x0x699789/47543d12-db34-4e6e-88a9-f3ae5d97b1d2/MacLachlan_mRNA_Conf_2013.pdf.
Teufel et al., Human peripheral blood mononuclear cells transfected with messenger RNA stimulate antigen-specific cytotoxic T-lymphocytes in vitro. Cell Mol Life Sci. Aug. 2005;62(15):1755-62.
Thess et al., Sequence-engineered mRNA Without Chemical Nucleoside Modifications Enables an Effective Protein Therapy in Large Animals. Mol Ther. Sep. 2015;23(9):1456-64.doi: 10.1038/mt.2015.103. Epub Jun. 8, 2015.
Torrecilla et al., Lipid Nanoparticles as Carriers for RNAi Against Viral Infections: Current Status and Future Perspectives. Biomed Res Int. 2014;2014:161794. doi: 10.1155/2014/161794. Epub Aug. 12, 2014.
Vassilev et al., Microparticle-mediated RNA immunization against bovine viral diarrhea virus. Vaccine. Feb. 28, 2001;19(15-16):2012-9.
Wang et al., Epstein-Barr virus lacking glycoprotein gp42 can bind to B cells but is not able to infect. J Virol. Jan. 1998;72(1):158-63. doi: 10.1128/JVI.72.1.158-163.1998.
Wang et al., Systemic delivery of modified mRNA encoding herpes simplex virus 1 thymidine kinase for targeted cancer gene therapy. Mol Ther. Feb. 2013;21(2):358-67. doi: 10.1038/mt.2012.250. Epub Dec. 11, 2012.
Weilhammer et al., The use of nanolipoprotein particles to enhance the immunostimulatory properties of innate immune agonists against lethal influenza challenge. Biomaterials. Dec. 2013;34(38):10305-18. doi: 10.1016/j.biomaterials.2013.09.038. Epub Sep. 27, 2013.
Wong et al., An mRNA vaccine for influenza. Nat Biotechnol. Dec. 2012;30(12):1202-4. doi: 10.1038/nbt.2439.

(56) References Cited

OTHER PUBLICATIONS

Yamamoto et al., Current prospects for mRNA gene delivery. Eur J Pharm Biopharm. Mar. 2009;71(3):484-9. doi: 10.1016/j.ejpb.2008.09.016. Epub Oct. 10, 2008.
Ying et al., Cancer therapy using a self-replicating RNA vaccine. Nat Med. Jul. 1999;5(7):823-7.
Zhou et al., RNA melanoma vaccine: induction of antitumor immunity by human glycoprotein 100 mRNA immunization. Hum Gene Ther. Nov. 1, 1999;10(16):2719-24.
Zhukovsky et al., Heterogeneity of early intermediates in cell-liposome fusion mediated by influenza hemagglutinin. Biophys J. Nov. 1, 2006;91(9):3349-58. doi: 10.1529/biophysj.106.088005. Epub Aug. 11, 2006.
Lutz et al., Unmodified mRNA in LNPs constitutes a competitive technology for prophylactic vaccines. NPJ Vaccines. Oct. 19, 2017:2:29. doi: 10.1038/s41541-017-0032-6. eCollection 2017.
[No Author Listed], "Moderna Announces First Participant Dosed in Phase 1 Study of its mRNA Epstein-Barr Virus (EBV) Vaccine," Modera News Release, Jan. 5, 2022, 5 pages.
Boumber, "Tumor mutational burden (TMB) as a biomarker of response to immunotherapy in small cell lung cancer," Journal of Thoracic Disease, Aug. 2018, 10(8):4689-4693.
Collins et al., "Combining vaccines and immune checkpoint inhibitors to prime, expand, and facilitate effective tumor immunotherapy," Expert Review of Vaccines, Aug. 3, 2018, 17(8):697-705.
Del Pozo-Rodríguez et al., "Lipid nanoparticles as vehicles for macromolecules: nucleic acids and peptides," Recent Patents on Drug Delivery & Formulation, Sep. 2011, 5(3):214-226.
European Search Report in European Application No. 180881012.1, mailed on Feb. 4, 2022, 11 pages.
European Search Report in European Application No. 180881012.1, mailed on Jul. 16, 2021, 12 pages.
European Search Report in European Application No. 22788824, mailed on Jan. 27, 2025, 9 pages.
Fang et al., "Development of Lipid-Shell and Polymer Core Nanoparticles with Water-Soluble Salidroside for Anti-Cancer Therapy," International Journal of Molecular Sciences, Feb. 25, 2014, 15(3):3373-3388.
Harenberg et al., "Persistence of Th1/Tc1 responses one year after tetravalent dengue vaccination in adults and adolescents in Singapore," Human Vaccines & Immunotherapeutics, Nov. 2013, 9(11):2317-2325.
International Preliminary Report on Patentability in International Application No. PCT/US2018/061926, mailed on Jun. 4, 2020, 7 pages.
International Preliminary Report on Patentability in International Application No. PCT/US2022/024530, mailed on Oct. 26, 2023, 6 pages.
International Search Report and Written Opinion in International Application No. PCT/US2018/061926, mailed Feb. 27, 2019, 26 pages.
International Search Report and Written Opinion in International Application No. PCT/US2024/013539, mailed on Jun. 4, 2024, 11 pages.
Leuschner et al., "Therapeutic siRNA silencing in inflammatory monocytes in mice," Nature Biotechnology, Oct. 9, 2011, 29(11):1005-1010.
Li et al., "The Epstein-Barr Virus (EBV) BZLF2 Gene Product Associates with the gH and gL Homologs of EBV and Carries an Epitope Critical to Infection of B Cells but Not of Epithelial Cells," Journal of Virology, Jul. 1995, 69(7):3987-3994.
Milagre et al., "A mouse model of melanoma driven by oncogenic KRAS," Cancer Research, Jul. 2010, 70(13):5549-5557.
Pascolo, "Messenger RNA-based vaccines," Expert Opinion on Biological Therapy, Aug. 2004, 4(8):1285-1294.
Schlatterer et al., "Universal initiator nucleotides for the enzymatic synthesis of 5'-amino- and 5'-thiol-modified RNA," Biochemical and biophysical research communications, Jun. 9, 2006, 344(3):887-892.
Théry et al., "The cell biology of antigen presentation in dendritic cells," Current Opinion in Immunology, Feb. 2001, 13(1):45-51.
U.S. Appl. No. 16/036,318, filed Jul. 16, 2018, Ciaramella et al.
U.S. Appl. No. 16/144,394, filed Sep. 27, 2018, Ciaramella et al.
U.S. Appl. No. 17/204,801, filed Mar. 17, 2021, Ciaramella et al.
U.S. Appl. No. 17/683,171, filed Feb. 28, 2022, Ciaramella et al.
U.S. Appl. No. 18/176,014, filed Feb. 28, 2023, Ciaramella.
U.S. Appl. No. 18/365,948, filed Aug. 4, 2023, Ciaramella.
U.S. Appl. No. 17/819,414, filed Aug. 12, 2022, Ciaramella.
U.S. Appl. No. 15/767,600, filed Apr. 11, 2018, Ciaramella et al.
U.S. Appl. No. 18/306,082, filed Apr. 24, 2023, Ciaramella et al.
U.S. Appl. No. 15/767,609, filed Apr. 11, 2018, Ciaramella et al.
U.S. Appl. No. 15/767,613, filed Apr. 11, 2018, Ciaramella et al.
U.S. Appl. No. 18/314,980, filed May 10, 2023, Ciaramella et al.
U.S. Appl. No. 15/767,618, filed Apr. 11, 2018, Ciaramella et al.
U.S. Appl. No. 18/481,204, filed Oct. 4, 2023, Ciaramella et al.
U.S. Appl. No. 17/590,479, filed Feb. 1, 2022, Ciaramella et al.
U.S. Appl. No. 16/897,859, filed Jun. 10, 2020, Ciaramella et al.
U.S. Appl. No. 17/737,532, filed May 5, 2022, Ciaramella et al.
U.S. Appl. No. 17/839,401, filed Jun. 13, 2022, Ciaramella et al.
U.S. Appl. No. 16/897,734, filed Jun. 10, 2020, Ciaramella et al.
U.S. Appl. No. 18/528,323, filed Dec. 4, 2023, Ciaramella et al.
U.S. Appl. No. 18/322,831, filed May 24, 2023, Ciaramella.
U.S. Appl. No. 18/189,512, filed Mar. 24, 2023, Ciaramella et al.
U.S. Appl. No. 18/055,193, filed Nov. 14, 2022, Ciaramella et al.
U.S. Appl. No. 18/354,574, filed Jul. 18, 2023, Ciaramella et al.
U.S. Appl. No. 17/823,255, filed Aug. 30, 2022, Ciaramella et al.
U.S. Appl. No. 17/245,973, filed Apr. 30, 2021, Ciaramella.
U.S. Appl. No. 17/938,823, filed Oct. 7, 2022, Ciaramella et al.
U.S. Appl. No. 16/765,285, filed May 19, 2020, Ciaramella et al.
U.S. Appl. No. 17/531,211, filed Nov. 19, 2021, Ciaramella et al.
U.S. Appl. No. 16/965,589, filed Jul. 28, 2020, Ciaramella et al.
U.S. Appl. No. 18/552,346, filed Sep. 25, 2023, Himansu et al.
U.S. Appl. No. 17/439,198, filed Sep. 14, 2021, Lusso et al.
U.S. Appl. No. 17/737,581, filed May 5, 2022, Panther et al.
U.S. Appl. No. 17/641,967, filed Mar. 10, 2022, John et al.
U.S. Appl. No. 17/840,478, filed Jun. 14, 2022, Kramarczyk et al.
U.S. Appl. No. 17/796,401, filed Jul. 29, 2022, Shaw et al.
U.S. Appl. No. 18/284,919, filed Sep. 29, 2023, Deal et al.
U.S. Appl. No. 17/797,784, filed Aug. 5, 2022, Stewart-Jones et al.
U.S. Appl. No. 18/028,126, filed Mar. 23, 2023, Stewart-Jones et al.
U.S. Appl. No. 17/572,465, filed Jan. 10, 2022, Nachbagauer et al.
U.S. Appl. No. 18/272,512, filed Jul. 14, 2023, Carfi et al.
U.S. Appl. No. 18/272,496, filed Jul. 14, 2023, Carfi et al.
U.S. Appl. No. 18/284,938, filed Sep. 29, 2023, Rabideau et al.
U.S. Appl. No. 18/569,768, filed Dec. 13, 2023, Stewart-Jones.
U.S. Appl. No. 18/569,776, filed Dec. 13, 2023, Stewart-Jones.
U.S. Appl. No. 18/282,097, filed Sep. 14, 2023, Stewart-Jones et al.
U.S. Appl. No. 18/555,087, filed Oct. 12, 2023, Nachbagauer et al.
U.S. Appl. No. 18/555,130, filed Oct. 12, 2023, Nachbagauer et al.
U.S. Appl. No. 18/351,843, filed Jul. 13, 2023, Bollman et al.
U.S. Appl. No. 18/351,057, filed Jul. 12, 2023, Bollman et al.
U.S. Appl. No. 18/335,949, filed Jun. 15, 2023, Nasir et al.
U.S. Appl. No. 18/494,666, filed Oct. 25, 2023, Nasir et al.
Cai et al., "Prophylactic and Therapeutic EBV Vaccines: Major Scientific Obstacles, Historical Progress, and Future Direction," Vaccines, Nov. 7, 2021, 9(11):1290, 23 pages.
Chen et al., "Current Developments and Challenges of mRNA Vaccines," Annual Review of Biomedical Engineering, Jun. 6, 2022, 24(1):85-109.
Goldman, "Stanford Medicine study shows why mRNA COVID-19 vaccine can cause myocarditis," Dec. 10, 2025, retrieved on Feb. 26, 2026, retrieved from URL <https://med.stanford.edu/news/all-news/2025/12/myocarditis-vaccine-covid.html>, 10 pages.
International Preliminary Report on Patentability in International Application No. PCT/US2024/013539, mailed on Aug. 14, 2025, 7 pages.
Oyston et al., "The current challenges for vaccine development," Journal of Medical Microbiology, Jul. 2012, 61(7):889-894.
U.S. Appl. No. 19/084,092, filed Mar. 19, 2025, Ciaramella.
U.S. Appl. No. 16/765,285, filed May 19, 2020, Ciaramella.
U.S. Appl. No. 19/149,954, filed Jul. 22, 2025, Bollman.

EPSTEIN-BARR VIRUS MRNA VACCINES

RELATED APPLICATIONS

This application is a national stage filing under 35 U.S.C. § 371 of International Application Number PCT/US2022/024530, filed Apr. 13, 2022, which claims the benefit under 35 U.S.C. § 119 (e) of U.S. provisional application No. 63/174,287, filed Apr. 13, 2021, the entire contents of each of which are herein incorporated by reference in their entireties.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Sep. 26, 2023, is named M137870165US02-SEQ-DQB and is 67,375 bytes in size.

BACKGROUND

Epstein-Barr virus (EBV), also referred to as human herpesvirus 4, is a common herpesvirus that is spread through bodily fluids, most commonly saliva, and contracted primarily by young children and adolescents (approximately 50% and approximately 89% seropositivity, respectively). It is a major cause of infectious mononucleosis in the U.S., accounting for over 90% of the approximately 1-2 million cases annually. Infectious mononucleosis can debilitate patients for weeks to months and, in some cases, can lead to hospitalization and splenic rupture. EBV infection is associated with the development and progression of certain lymphoproliferative disorders, cancers, and an increased risk of autoimmune diseases including multiple sclerosis, an autoimmune disease of the central nervous system. There is no approved vaccine for EBV.

SUMMARY

A messenger ribonucleic acid (mRNA)-based vaccine platform has been developed based on the principle and observations that target viral proteins (antigens) can be produced in vivo by delivery and cellular uptake of the corresponding synthetic viral mRNA from delivery of a vaccine comprising the mRNA formulated in a lipid nanoparticle. The mRNA then undergoes intracellular ribosomal translation to endogenously express the viral proteins encoded by the vaccine comprising synthetic viral mRNA. These mRNA-based vaccines do not enter the cellular nucleus or interact with the human genome, are nonreplicating, and are expressed transiently. mRNA vaccines offer a mechanism to stimulate the endogenous production in human cells of multiple structurally intact, properly folded and glycosylated viral glycoproteins, for example, in a manner that mimics wild-type viral infection and is able to induce highly targeted immune responses against infectious pathogens such as EBV.

Some aspects of the present disclosure provide a vaccine, comprising a lipid nanoparticle that comprises: (a) a messenger ribonucleic acid (mRNA) comprising an open reading frame encoding an Epstein-Barr virus (EBV) glycoprotein 220 (gp220); (b) an mRNA comprising an open reading frame encoding glycoprotein 42 (gp42); (c) an mRNA comprising an open reading frame encoding glycoprotein L (gL); and (d) an mRNA comprising an open reading frame encoding glycoprotein H (gH).

In some embodiments, the gp42 is a soluble form of gp42.

In some embodiments, the mass ratio of (a):(b):(c):(d) is 4:1:1:1.5. In other embodiments, the mass ratio of (a):(b):(c):(d) is 4:1:1:1.

In some embodiments, the vaccine of claim 1 or 2, wherein mRNA of (a) is at 5×, 4.5×, 4×, 3.5×, 3×, 2.5×, 2×, or 1.5× the mRNA of (b), (c), and/or (d). In some embodiments, the mRNA of (a) is at equal mass to the mRNA of (b), (c), and/or (d).

In some embodiments, the mRNA of (b) is at 5×, 4.5×, 4×, 3.5×, 3×, 2.5×, 2×, or 1.5× the mRNA of (a), (c), and/or (d). In some embodiments, the mRNA of (b) is at equal mass to the mRNA of a), (c), and/or (d).

In some embodiments, the mRNA of (c) is at 5×, 4.5×, 4×, 3.5×, 3×, 2.5×, 2×, or 1.5× the mRNA of (a), (b), and/or (d). In some embodiments, the mRNA of (c) is at equal mass to the mRNA of (a), (b), and/or (d).

In some embodiments, the mRNA of (d) is at 5×, 4.5×, 4×, 3.5×, 3×, 2.5×, 2×, or 1.5× the mRNA of (a), (b), and/or (c). In some embodiments, the mRNA of (d) is at equal mass to the mRNA of (a), (b), and/or (c).

In some embodiments, the vaccine comprises 26.7 μg mRNA encoding EBV gp220, 6.7 μg mRNA encoding EBV gp42, 6.7 μg mRNA encoding EBV gL, and 10 μg mRNA encoding EBV gH. In other embodiments, the vaccine comprises 53.3 μg mRNA encoding EBV gp220, 13.3 μg mRNA encoding EBV gp42, 13.3 μg mRNA encoding EBV gL, and 20 μg mRNA encoding EBV gH. In still other embodiments, the vaccine comprises 106.7 μg mRNA encoding EBV gp220, 26.7 μg mRNA encoding EBV gp42, 26.7 μg mRNA encoding EBV gL, and 40 μg mRNA encoding EBV gH In some embodiments, the lipid nanoparticle further comprises (e) an mRNA comprising an open reading frame encoding glycoprotein B. In some embodiments, the mass ratio of (a):(b):(c):(d):(c) is 4:1:1:1.5:1.5.

In some embodiments, the gp220 comprises an amino acid sequence having at least 85%, at least 90%, at least 95%, or at least 98% identity to the amino acid sequence of SEQ ID NO: 4. In some embodiments, the gp220 comprises the amino acid sequence of SEQ ID NO: 4.

In some embodiments, the gL comprises an amino acid sequence having at least 85%, at least 90%, at least 95%, or at least 98% identity to the amino acid sequence of SEQ ID NO: 8. In some embodiments, the gL comprises the amino acid sequence of SEQ ID NO: 8.

In some embodiments, the gH comprises an amino acid sequence having at least 85%, at least 90%, at least 95%, or at least 98% identity to the amino acid sequence of SEQ ID NO: 6. In some embodiments, the gH comprises the amino acid sequence of SEQ ID NO: 6.

In some embodiments, the gp42 comprises an amino acid sequence having at least 85%, at least 90%, at least 95%, or at least 98% identity to the amino acid sequence of SEQ ID NO: 14. In some embodiments, the gp42 comprises the amino acid sequence of SEQ ID NO: 14.

In some embodiments, the soluble gp42 comprises an amino acid sequence having at least 85%, at least 90%, at least 95%, or at least 98% identity to the amino acid sequence of SEQ ID NO: 10. In some embodiments, the soluble gp42 comprises the amino acid sequence of SEQ ID NO: 10.

In some embodiments, the gB comprises an amino acid sequence having at least 85%, at least 90%, at least 95%, or at least 98% identity to the amino acid sequence of SEQ ID NO: 12. In some embodiments, the gB comprises the amino acid sequence of SEQ ID NO: 12.

In some embodiments, the mRNA of any one or more of (a)-(e) comprises a 5' 7mG(5')ppp(5')NlmpNp cap and a 3' polyA tail.

In some embodiments, the mRNA of any one or more of (a)-(e) comprises a 1-methylpseudourine chemical modification.

In some embodiments, the lipid nanoparticle comprises 45-55 mol % ionizable amino lipid, 15-20 mol % neutral lipid, 35-45 mol % cholesterol, and 0.5-5 mol % PEG-modified lipid.

In some embodiments, the ionizable amino lipid is Compound I:

(Compound I)

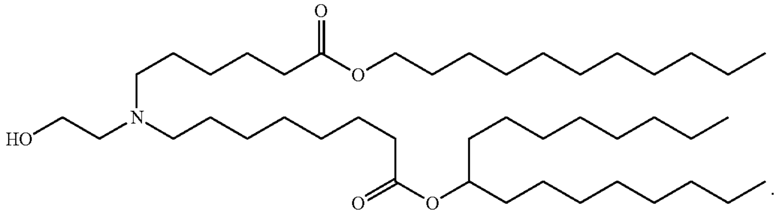

In some embodiments, the lipid nanoparticle comprises 50 mol % ionizable amino lipid. In other embodiments, the lipid nanoparticle comprises 49 mol % ionizable amino lipid. In yet other embodiments, the lipid nanoparticle comprises 48 mol % ionizable amino lipid.

Other aspects of the present disclosure provide a method comprising administering to a subject the vaccine of any one of the preceding claims in an amount effective to induce an immune response to EBV.

In some embodiments, the vaccine is administered as a single dose. In other embodiments, the vaccine is administered as an initial dose and as at least one booster dose.

BRIEF DESCRIPTION OF THE DRAWINGS

FIG. 5A: EBV gHgL; FIG. 5B: EBV gp220; FIG. 5C: EBV gp42. The mRNA vaccine was immunogenic at both doses, raising binding antibodies to all four antigens (gHgL, gp220 and sgp42).

FIG. 6A: EBV gHgL; FIG. 6B: EBV sgp42; FIG. 6C: EBV gp220. All doses evaluated elicited strong serum IgG responses against the vaccine antigens.

DETAILED DESCRIPTION

Figure 1:
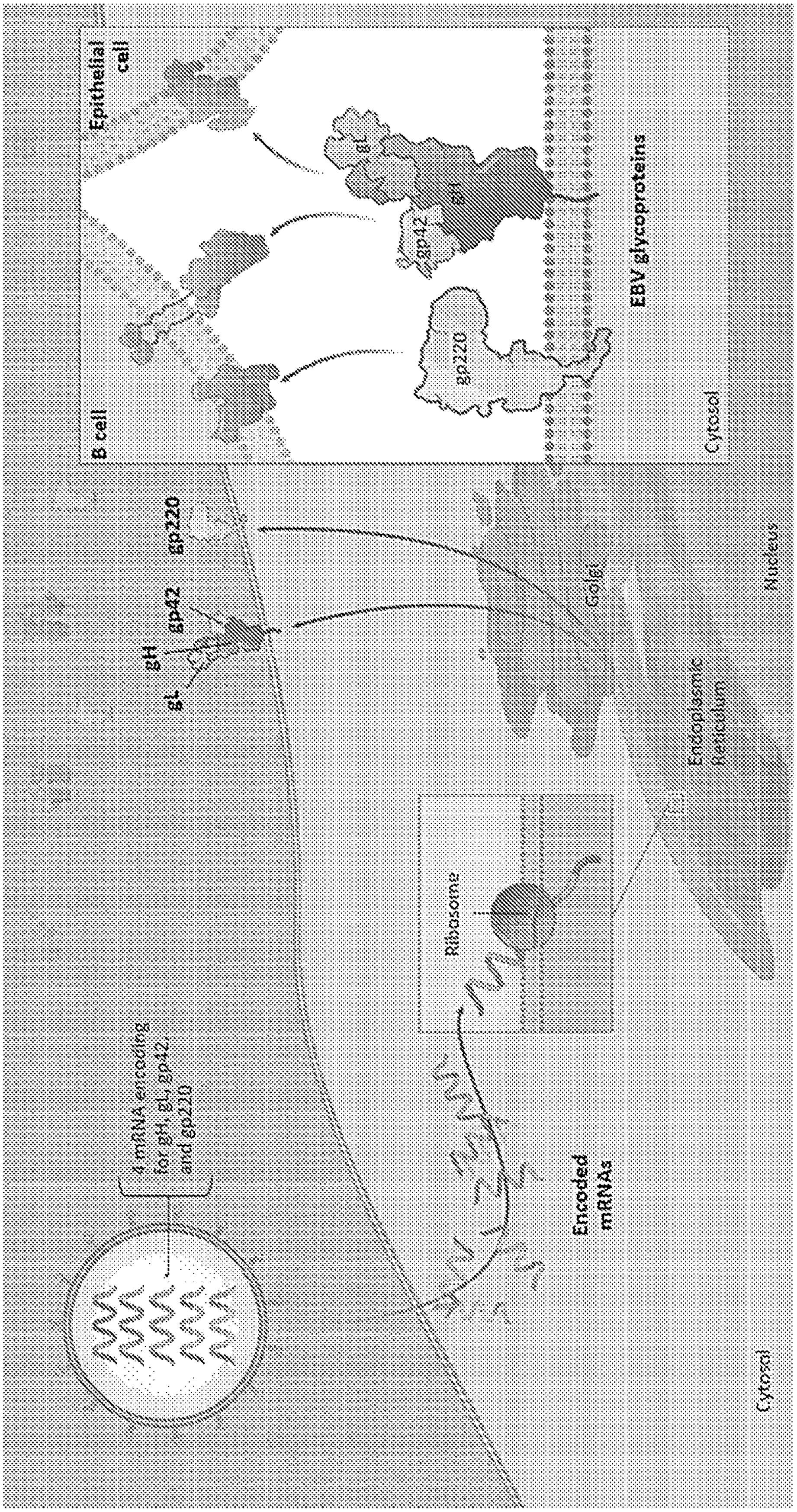
FIG. 1 is a schematic depicting intracellular delivery of the EBV mRNA vaccine and expression of the encoded EBV glycoproteins at the cell surface.

EBV is a member of the herpesvirus family that includes CMV, is spread through bodily fluids (e.g., saliva) and contracted primarily by young children and adolescents. The EBV lifecycle has lytic and latent stages, similar to other herpesviruses such as CMV, as well as multiple surface (envelope) glycoproteins that mediate virus entry in different cell types. The mRNA vaccine against EBV as provide herein contains at least four mRNAs that encode viral proteins (gp220, gp42, gH and gL) in EBV. In some embodiments, these viral proteins are expressed in their native membrane-bound form for recognition by the immune system. In other embodiments, gp42 is expressed in a soluble form. In some embodiments, the vaccine further comprises an mRNA that encodes EBV glycoprotein B (gB).

The EBV mRNA vaccines described herein are superior to current vaccines in several ways. For example, the lipid nanoparticle (LNP) delivery system used herein increases the efficacy of mRNA vaccines in comparison to other formulations, including a protamine-based approach described in the literature. The use of this LNP delivery system enables the effective delivery of chemically-modified RNA vaccines or unmodified mRNA vaccines, without requiring additional adjuvant to produce a therapeutic result (e.g., production neutralizing antibody titer). In some embodiments, the EBV mRNA vaccines disclosed herein are superior to conventional vaccines by a factor of at least 10-fold, 20-fold, 40-fold, 50-fold, 100-fold, 500-fold, or 1,000-fold when administered intramuscularly (IM) or intradermally (ID). These results can be achieved even when significantly lower doses of the mRNA are administered in comparison with RNA doses used in other classes of lipid-based formulations.

Further, unlike self-replicating RNA vaccines, which rely on viral replication pathways to deliver enough RNA to a cell to produce an immunogenic response, the vaccines of the present disclosure do not require viral replication to produce enough protein to result in a strong immune response. Thus, the vaccines of the present disclosure do not include self-replicating RNA and do not include components necessary for viral replication.

It should be understood that the mRNA of the vaccines of the present disclosure are not naturally occurring. That is, the mRNA encoding the EBV antigen, as provided herein, does not occur in nature. It should also be understood that the vaccines described herein exclude viruses (i.e., the vaccines are not, nor do they contain, viruses).

EBV Antigens

Antigens are proteins capable of inducing an immune response (e.g., causing an immune system to produce antibodies against the antigens). Herein, use of the term "antigen" encompasses immunogenic/antigenic proteins and immunogenic/antigenic fragments (e.g., an immunogenic/antigenic fragment that induces (or is capable of inducing) an immune response to human EBV). It should also be understood that the term "protein" encompasses full length proteins, truncated proteins, modified proteins, and peptides.

Exemplary nucleic acid and amino acids sequences of the EBV antigen of the vaccine provided herein are provided in Table 3.

In some embodiments, the gp220 comprises an amino acid sequence having at least 85% identity to the amino acid sequence of SEQ ID NO: 4. In some embodiments, the gp220 comprises an amino acid sequence having at least 90% identity to the amino acid sequence of SEQ ID NO: 4. In some embodiments, the gp220 comprises an amino acid sequence having at least 95% identity to the amino acid sequence of SEQ ID NO: 4. In some embodiments, the gp220 comprises an amino acid sequence having at least 98% identity to the amino acid sequence of SEQ ID NO: 4. In some embodiments, the gp220 comprises the amino acid sequence of SEQ ID NO: 4.

In some embodiments, the gL comprises an amino acid sequence having at least 85% identity to the amino acid sequence of SEQ ID NO: 8. In some embodiments, the gL comprises an amino acid sequence having at least 90% identity to the amino acid sequence of SEQ ID NO: 8. In some embodiments, the gL comprises an amino acid sequence having at least 95% identity to the amino acid sequence of SEQ ID NO: 8. In some embodiments, the gL comprises an amino acid sequence having at least at least 98% identity to the amino acid sequence of SEQ ID NO: 8. In some embodiments, the gL comprises the amino acid sequence of SEQ ID NO: 8.

In some embodiments, the gH comprises an amino acid sequence having at least 85% identity to the amino acid sequence of SEQ ID NO: 6. In some embodiments, the gH comprises an amino acid sequence having at least 90% identity to the amino acid sequence of SEQ ID NO: 6. In some embodiments, the gH comprises an amino acid sequence having at least 95% identity to the amino acid sequence of SEQ ID NO: 6. In some embodiments, the gH comprises an amino acid sequence having at least 98% identity to the amino acid sequence of SEQ ID NO: 6. In some embodiments, the gH comprises the amino acid sequence of SEQ ID NO: 6.

In some embodiments, the gp42 comprises an amino acid sequence having at least 85% identity to the amino acid sequence of SEQ ID NO: 14. In some embodiments, the gp42 comprises an amino acid sequence having at least 90% identity to the amino acid sequence of SEQ ID NO: 14. In some embodiments, the gp42 comprises an amino acid sequence having at least 95% identity to the amino acid sequence of SEQ ID NO: 14. In some embodiments, the gp42 comprises an amino acid sequence having at least 98% identity to the amino acid sequence of SEQ ID NO: 14. In some embodiments, the gp42 comprises the amino acid sequence of SEQ ID NO: 14.

In some embodiments, the soluble gp42 comprises an amino acid sequence having at least 85% identity to the amino acid sequence of SEQ ID NO: 10. In some embodiments, the soluble gp42 comprises an amino acid sequence having at least 90% identity to the amino acid sequence of SEQ ID NO: 10. In some embodiments, the soluble gp42 comprises an amino acid sequence having at least 95% identity to the amino acid sequence of SEQ ID NO: 10. In some embodiments, the soluble gp42 comprises an amino acid sequence having at least 98% identity to the amino acid sequence of SEQ ID NO: 10. In some embodiments, the soluble gp42 comprises the amino acid sequence of SEQ ID NO: 10.

In some embodiments, the gB comprises an amino acid sequence having at least 85% identity to the amino acid sequence of SEQ ID NO: 12. In some embodiments, the gB comprises an amino acid sequence having at least 90% identity to the amino acid sequence of SEQ ID NO: 12. In some embodiments, the gB comprises an amino acid sequence having at least 95% identity to the amino acid sequence of SEQ ID NO: 12. In some embodiments, the gB comprises an amino acid sequence having at least 98% identity to the amino acid sequence of SEQ ID NO: 12. In some embodiments, the gB comprises the amino acid sequence of SEQ ID NO: 12.

It should be understood that the mRNA F protein described herein may or may not comprise a signal sequence.

EBV Nucleic Acids

The vaccines of the present disclosure comprise a (at least one) mRNA having an open reading frame (ORF) encoding an EBV antigen. In some embodiments, the mRNA further comprises a 5' UTR, 3' UTR, a poly(A) tail and/or a 5' cap analog.

It should also be understood that the mRNA vaccine of the present disclosure may include any 5' untranslated region (UTR) and/or any 3' UTR. Exemplary UTR sequences are provided in the Sequence Listing (e.g., SEQ ID NOs: 2-5); however, other UTR sequences may be used or exchanged for any of the UTR sequences described herein. UTRs may also be omitted from the mRNA polynucleotides provided herein.

Nucleic acids comprise a polymer of nucleotides (nucleotide monomers). Thus, nucleic acids are also referred to as polynucleotides. Nucleic acids may be or may include, for example, deoxyribonucleic acids (DNAs), ribonucleic acids (RNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) and/or chimeras and/or combinations thereof.

Messenger RNA (mRNA) is any RNA that encodes a (at least one) protein (a naturally occurring, non-naturally occurring, or modified polymer of amino acids) and can be translated to produce the encoded protein in vitro, in vivo, in situ, or ex vivo. The skilled artisan will appreciate that, except where otherwise noted, nucleic acid sequences set forth in the instant application may recite "T"s in a representative DNA sequence but where the sequence represents mRNA, the "T"'s would be substituted for "U"s. Thus, any of the DNAs disclosed and identified by a particular sequence identification number herein also disclose the corresponding mRNA sequence complementary to the DNA, where each "T" of the DNA sequence is substituted with "U."

An open reading frame (ORF) is a continuous stretch of DNA or RNA beginning with a start codon (e.g., methionine (ATG or AUG)) and ending with a stop codon (e.g., TAA, TAG or TGA, or UAA, UAG or UGA). An ORF typically encodes a protein. It will be understood that the sequences disclosed herein may further comprise additional elements, e.g., 5' and 3' UTRs, but that those elements, unlike the ORF, need not necessarily be present in an mRNA polynucleotide of the present disclosure.

Variants

In some embodiments, the vaccines of the present disclosure include mRNA that encodes an EBV antigen variant. Antigen variants or other polypeptide variants refers to molecules that differ in their amino acid sequence from a wild-type, native, or reference sequence. The antigen/polypeptide variants may possess substitutions, deletions, and/or insertions at certain positions within the amino acid sequence, as compared to a native or reference sequence. Ordinarily, variants possess at least 50% identity to a wild-type, native or reference sequence. In some embodiments, variants share at least 80%, at least 85%, or at least 90% identity with a wild-type, native, or reference sequence.

Variant antigens/polypeptides encoded by nucleic acids of the disclosure may contain amino acid changes that confer any of a number of desirable properties, e.g., that enhance their immunogenicity, enhance their expression, and/or improve their stability or PK/PD properties in a subject. Variant antigens/polypeptides can be made using routine mutagenesis techniques and assayed as appropriate to determine whether they possess the desired property. Assays to determine expression levels and immunogenicity are well known in the art and exemplary such assays are set forth in the Examples section. Similarly, PK/PD properties of a protein variant can be measured using art recognized techniques, e.g., by determining expression of antigens in a vaccinated subject over time and/or by looking at the durability of the induced immune response. The stability of protein(s) encoded by a variant nucleic acid may be measured by assaying thermal stability or stability upon urea denaturation or may be measured using in silico prediction. Methods for such experiments and in silico determinations are known in the art.

In some embodiments, a vaccine comprises an mRNA or an mRNA open reading frame that comprises a nucleotide sequence of any one of the sequences provided herein (see, e.g., Sequence Listing and Table 3), or comprises a nucleotide sequence at least 80%, at least 85%, at least 90%, at least 95%, at least 96%, at least 97%, at least 98%, or at least 99% identical to a nucleotide sequence of any one of the sequences provided herein.

The term "identity" refers to a relationship between the sequences of two or more polypeptides (e.g., antigens) or polynucleotides (nucleic acids), as determined by comparing the sequences. Identity also refers to the degree of sequence relatedness between or among sequences as determined by the number of matches between strings of two or more amino acid residues or nucleic acid residues. Identity measures the percent of identical matches between the smaller of two or more sequences with gap alignments (if any) addressed by a particular mathematical model or computer program (e.g., "algorithms"). Identity of related antigens or nucleic acids can be readily calculated by known methods. "Percent (%) identity" as it applies to polypeptide or polynucleotide sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Methods and computer programs for the alignment are well known in the art. It is understood that identity depends on a calculation of percent identity but may differ in value due to gaps and penalties introduced in the calculation. Generally, variants of a particular polynucleotide or polypeptide (e.g., antigen) have at least 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, et al (1997), "Gapped BLAST and PSI-BLAST: a new generation of protein database search programs", Nucleic Acids Res. 25:3389-3402). Another popular local alignment technique is based on the Smith-Waterman algorithm (Smith, T. F. & Waterman, M. S. (1981) "Identification of common molecular subsequences." J. Mol. Biol. 147:195-197). A general global alignment technique based on dynamic programming is the Needleman-Wunsch algorithm (Needleman, S. B. & Wunsch, C. D. (1970) "A general method applicable to the search for similarities in the amino acid sequences of two proteins." J. Mol. Biol. 48:443-453). More recently a Fast Optimal Global Sequence Alignment Algorithm (FOGSAA) has been developed that purportedly produces global alignment of nucleotide and protein sequences faster than other optimal global alignment methods, including the Needleman-Wunsch algorithm.

As such, polynucleotides encoding peptides or polypeptides containing substitutions, insertions and/or additions, deletions and covalent modifications with respect to reference sequences, in particular the polypeptide (e.g., antigen) sequences disclosed herein, are included within the scope of this disclosure. For example, sequence tags or amino acids, such as one or more lysines, can be added to peptide sequences (e.g., at the N-terminal or C-terminal ends). Sequence tags can be used for peptide detection, purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble or linked to a solid support. In some embodiments, sequences for (or encoding) signal sequences, termination sequences, transmembrane domains, linkers, multimerization domains (such as, e.g., foldon regions) and the like may be substituted with alternative sequences that achieve the same or a similar function. In some embodiments, cavities in the core of proteins can be filled to improve stability, e.g., by introducing larger amino acids. In other embodiments, buried hydrogen bond networks may be replaced with hydrophobic resides to improve stability. In yet other embodiments, glycosylation sites may be removed and replaced with appropriate residues. Such sequences are readily identifiable to one of skill in the art. It should also be understood that some of the sequences provided herein contain sequence tags or terminal peptide sequences (e.g., at the N-terminal or C-terminal ends) that may be deleted, for example, prior to use in the preparation of an mRNA vaccine.

As recognized by those skilled in the art, protein fragments, functional protein domains, and homologous proteins are also considered to be within the scope of EBV antigens of interest. For example, provided herein is any protein fragment (meaning a polypeptide sequence at least one amino acid residue shorter than a reference antigen sequence but otherwise identical) of a reference protein, provided that the fragment is immunogenic and confers a protective immune response to the EBV. In addition to variants that are identical to the reference protein but are truncated, in some embodiments, an antigen includes 2, 3, 4, 5, 6, 7, 8, 9, 10, or more mutations, as shown in any of the sequences provided or referenced herein. Antigens/antigenic polypeptides can range in length from about 4, 6, or 8 amino acids to full length proteins.

Stabilizing Elements

Naturally occurring eukaryotic mRNA molecules can contain stabilizing elements, including, but not limited to untranslated regions (UTR) at their 5'-end (5' UTR) and/or at their 3'-end (3' UTR), in addition to other structural features, such as a 5'-cap structure or a 3'-poly(A) tail. Both the 5' UTR and the 3' UTR are typically transcribed from the genomic DNA and are elements of the premature mRNA. Characteristic structural features of mature mRNA, such as the 5'-cap and the 3'-poly(A) tail are usually added to the transcribed (premature) mRNA during mRNA processing.

In some embodiments, a vaccine includes an mRNA having an open reading frame encoding at least one antigenic polypeptide having at least one modification, at least one 5' terminal cap, and is formulated within a lipid nanoparticle. 5'-capping of polynucleotides may be completed concomitantly during the in vitro-transcription reaction using the following chemical RNA cap analogs to generate the 5'-guanosine cap structure according to manufacturer protocols: 3'-O-Me-m7G(5')ppp(5') G [the ARCA cap]; G(5')ppp(5')A; G(5')ppp(5')G; m7G(5')ppp(5')A; m7G(5')ppp(5')G (New England BioLabs, Ipswich, MA). 5'-capping of mRNA may be completed post-transcriptionally using a Vaccinia Virus Capping Enzyme to generate the "Cap 0" structure: m7G(5')ppp(5')G (New England BioLabs, Ipswich, MA). Cap 1 structure may be generated using both Vaccinia Virus Capping Enzyme and a 2'-O methyl-transferase to generate: m7G(5')ppp(5')G-2'-O-methyl. Cap 2 structure may be generated from the Cap 1 structure followed by the 2'-O-methylation of the 5'-antepenultimate nucleotide using a 2'-O methyl-transferase. Cap 3 structure may be generated from the Cap 2 structure followed by the 2'-O-methylation of the 5'-preantepenultimate nucleotide using a 2'-O methyl-transferase. Enzymes may be derived from a recombinant source.

The 3'-poly(A) tail is typically a stretch of adenine nucleotides added to the 3'-end of the transcribed mRNA. It can, in some instances, comprise up to about 400 adenine nucleotides. In some embodiments, the length of the 3'-poly (A) tail may be an essential element with respect to the stability of the individual mRNA.

In some embodiments, a vaccine includes a stabilizing element. Stabilizing elements may include for instance a histone stem-loop. A stem-loop binding protein (SLBP), a 32 kDa protein has been identified. It is associated with the histone stem-loop at the 3'-end of the histone messages in both the nucleus and the cytoplasm. Its expression level is regulated by the cell cycle; it peaks during the S-phase, when histone mRNA levels are also elevated. The protein has been shown to be essential for efficient 3'-end processing of histone pre-mRNA by the U7 snRNP. SLBP continues to be associated with the stem-loop after processing, and then stimulates the translation of mature histone mRNAs into histone proteins in the cytoplasm. The mRNA binding domain of SLBP is conserved through metazoa and protozoa; its binding to the histone stem-loop depends on the structure of the loop. The minimum binding site includes at least three nucleotides 5' and two nucleotides 3' relative to the stem-loop.

In some embodiments, an mRNA includes a coding region, at least one histone stem-loop, and optionally, a poly(A) sequence or polyadenylation signal. The poly(A) sequence or polyadenylation signal generally should enhance the expression level of the encoded protein. The encoded protein, in some embodiments, is not a histone protein, a reporter protein (e.g. Luciferase, GFP, EGFP, β-Galactosidase, EGFP), or a marker or selection protein (e.g. alpha-Globin, Galactokinase and Xanthine:guanine phosphoribosyl transferase (GPT)).

In some embodiments, an mRNA includes the combination of a poly(A) sequence or polyadenylation signal and at least one histone stem-loop, even though both represent alternative mechanisms in nature, acts synergistically to increase the protein expression beyond the level observed with either of the individual elements. The synergistic effect of the combination of poly(A) and at least one histone stem-loop does not depend on the order of the elements or the length of the poly(A) sequence.

In some embodiments, an mRNA does not include a histone downstream element (HDE). "Histone downstream element" (HDE) includes a purine-rich polynucleotide stretch of approximately 15 to 20 nucleotides 3' of naturally occurring stem-loops, representing the binding site for the U7 snRNA, which is involved in processing of histone pre-mRNA into mature histone mRNA. In some embodiments, the nucleic acid does not include an intron.

An mRNA may or may not contain an enhancer and/or promoter sequence, which may be modified or unmodified or which may be activated or inactivated. In some embodiments, the histone stem-loop is generally derived from histone genes and includes an intramolecular base pairing of two neighbored partially or entirely reverse complementary sequences separated by a spacer, consisting of a short sequence, which forms the loop of the structure. The unpaired loop region is typically unable to base pair with either of the stem loop elements. It occurs more often in RNA, as is a key component of many RNA secondary structures but may be present in single-stranded DNA as well. Stability of the stem-loop structure generally depends on the length, number of mismatches or bulges, and base vaccine of the paired region. In some embodiments, wobble base pairing (non-Watson-Crick base pairing) may result. In some embodiments, the at least one histone stem-loop sequence comprises a length of 15 to 45 nucleotides.

In some embodiments, an mRNA has one or more AU-rich sequences removed. These sequences, sometimes referred to as AURES are destabilizing sequences found in the 3'UTR. The AURES may be removed from the mRNA vaccines. Alternatively, the AURES may remain in the mRNA vaccine.

Signal Peptides

In some embodiments, a vaccine comprises an mRNA having an open reading frame that encodes a signal peptide fused to the EBV antigen. Signal peptides, comprising the N-terminal 15-60 amino acids of proteins, are typically needed for the translocation across the membrane on the secretory pathway and, thus, universally control the entry of most proteins both in eukaryotes and prokaryotes to the secretory pathway. In eukaryotes, the signal peptide of a nascent precursor protein (pre-protein) directs the ribosome to the rough endoplasmic reticulum (ER) membrane and initiates the transport of the growing peptide chain across it for processing. ER processing produces mature proteins, wherein the signal peptide is cleaved from precursor proteins, typically by a ER-resident signal peptidase of the host cell, or they remain uncleaved and function as a membrane anchor. A signal peptide may also facilitate the targeting of the protein to the cell membrane.

A signal peptide may have a length of 15-60 amino acids. For example, a signal peptide may have a length of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids. In some embodiments, a signal peptide has a length of 20-60, 25-60, 30-60, 35-60, 40-60, 45-60, 50-60, 55-60, 15-55, 20-55, 25-55, 30-55, 35-55, 40-55, 45-55, 50-55, 15-50, 20-50, 25-50, 30-50, 35-50, 40-50, 45-50, 15-45, 20-45, 25-45, 30-45, 35-45, 40-45, 15-40, 20-40, 25-40, 30-40, 35-40, 15-35, 20-35, 25-35, 30-35, 15-30, 20-30, 25-30, 15-25, 20-25, or 15-20 amino acids.

Signal peptides from heterologous genes (which regulate expression of genes other than EBV antigens in nature) are known in the art and can be tested for desired properties and then incorporated into a nucleic acid of the disclosure. In some embodiments, the signal peptide may comprise one of the following sequences: MDSKGSSQKGSRLLLLLVVSNLLLPQGVVG (SEQ ID NO: 26), MDWTWILFLVAAATRVHS (SEQ ID NO: 27); METPAQLLFLLLLWLPDTTG (SEQ ID NO: 28); MLGSNSGQRVVFTILLLLVAPAYS (SEQ ID NO: 29); MKCLLYLAFLFIGVNCA (SEQ ID NO: 30); MWLVSLAIVTACAGA (SEQ ID NO: 31).

Fusion Proteins

In some embodiments, a vaccine of the present disclosure includes an mRNA encoding an antigenic fusion protein. Thus, the encoded antigen or antigens may include two or more proteins (e.g., protein and/or protein fragment) joined together. Alternatively, the protein to which a protein antigen is fused does not promote a strong immune response to itself, but rather to the EBV antigen. Antigenic fusion proteins, in some embodiments, retain the functional property from each original protein.

Scaffold Moieties

The mRNA vaccines as provided herein, in some embodiments, encode fusion proteins that comprise EBV antigens linked to scaffold moieties. In some embodiments, such scaffold moieties impart desired properties to an antigen encoded by a nucleic acid of the disclosure. For example, scaffold proteins may improve the immunogenicity of an antigen, e.g., by altering the structure of the antigen, altering the uptake and processing of the antigen, and/or causing the antigen to bind to a binding partner.

In some embodiments, the scaffold moiety is protein that can self-assemble into protein nanoparticles that are highly symmetric, stable, and structurally organized, with diameters of 10-150 nm, a highly suitable size range for optimal interactions with various cells of the immune system. In some embodiments, viral proteins or virus-like particles can be used to form stable nanoparticle structures. Examples of such viral proteins are known in the art. For example, in some embodiments, the scaffold moiety is a hepatitis B surface antigen (HBsAg). HBsAg forms spherical particles with an average diameter of ~22 nm and which lacked nucleic acid and hence are non-infectious (Lopez-Sagaseta, J. et al. Computational and Structural Biotechnology Journal 14 (2016) 58-68). In some embodiments, the scaffold moiety is a hepatitis B core antigen (HBcAg) self-assembles into particles of 24-31 nm diameter, which resembled the viral cores obtained from HBV-infected human liver. HBcAg produced in self-assembles into two classes of differently sized nanoparticles of 300 Å and 360 Å diameter, corresponding to 180 or 240 protomers. In some embodiments, the EBV antigen is fused to HBSAG or HBcAG to facilitate self-assembly of nanoparticles displaying the EBV antigen.

In some embodiments, bacterial protein platforms may be used. Non-limiting examples of these self-assembling proteins include ferritin, lumazine and encapsulin.

Ferritin is a protein whose main function is intracellular iron storage. Ferritin is made of 24 subunits, each composed of a four-alpha-helix bundle, that self-assemble in a quaternary structure with octahedral symmetry (Cho K. J. et al. *J Mol Biol.* 2009; 390:83-98). Several high-resolution structures of ferritin have been determined, confirming that *Helicobacter pylori* ferritin is made of 24 identical protomers, whereas in animals, there are ferritin light and heavy chains that can assemble alone or combine with different ratios into particles of 24 subunits (Granier T. et al. *J Biol Inorg Chem.* 2003; 8:105-111; Lawson D. M. et al. *Nature.* 1991; 349:541-544). Ferritin self-assembles into nanoparticles with robust thermal and chemical stability. Thus, the ferritin nanoparticle is well-suited to carry and expose antigens.

Lumazine synthase (LS) is also well-suited as a nanoparticle platform for antigen display. LS, which is responsible for the penultimate catalytic step in the biosynthesis of riboflavin, is an enzyme present in a broad variety of organisms, including archaea, bacteria, fungi, plants, and eubacteria (Weber S. E. Flavins and Flavoproteins. Methods and Protocols, Series: Methods in Molecular Biology. 2014). The LS monomer is 150 amino acids long and consists of beta-sheets along with tandem alpha-helices flanking its sides. A number of different quaternary structures have been reported for LS, illustrating its morphological versatility: from homopentamers up to symmetrical assemblies of 12 pentamers forming capsids of 150 Å diameter. Even LS cages of more than 100 subunits have been described (Zhang X. et al. J Mol Biol. 2006; 362:753-770).

Encapsulin, a novel protein cage nanoparticle isolated from thermophile *Thermotoga maritima*, may also be used as a platform to present antigens on the surface of self-assembling nanoparticles. Encapsulin is assembled from 60 copies of identical 31 kDa monomers having a thin and icosahedral T=1 symmetric cage structure with interior and exterior diameters of 20 and 24 nm, respectively (Sutter M. et al. Nat Struct Mol Biol. 2008, 15: 939-947). Although the exact function of encapsulin in *T. maritima* is not clearly understood yet, its crystal structure has been recently solved and its function was postulated as a cellular compartment that encapsulates proteins such as DyP (Dye decolorizing peroxidase) and Flp (Ferritin like protein), which are involved in oxidative stress responses (Rahmanpour R. et al. FEBS J. 2013, 280: 2097-2104).

Linkers and Cleavable Peptides

In some embodiments, the mRNAs of the disclosure encode more than one polypeptide, referred to herein as fusion proteins. In some embodiments, the mRNA further encodes a linker located between at least one or each domain of the fusion protein. The linker can be, for example, a cleavable linker or protease-sensitive linker. In some embodiments, the linker is selected from the group consisting of F2A linker, P2A linker, T2A linker, E2A linker, and combinations thereof. This family of self-cleaving peptide linkers, referred to as 2A peptides, has been described in the art (see for example, Kim, J. H. et al. (2011) *PLOS ONE* 6:018556). In some embodiments, the linker is an F2A linker. In some embodiments, the linker is a GGGS linker. In some embodiments, the fusion protein contains three domains with intervening linkers, having the structure: domain-linker-domain-linker-domain.

Cleavable linkers known in the art may be used in connection with the disclosure. Exemplary such linkers include: F2A linkers, T2A linkers, P2A linkers, E2A linkers (See, e.g., WO2017127750). The skilled artisan will appreciate that other art-recognized linkers may be suitable for use in the mRNAs of the disclosure (e.g., encoded by the nucleic acids of the disclosure). The skilled artisan will likewise appreciate that other polycistronic mRNA encoding more than one antigen/polypeptide separately within the same molecule) may be suitable for use as provided herein.

Sequence Optimization

In some embodiments, an ORF encoding an antigen of the disclosure is codon optimized. Codon optimization methods are known in the art. For example, an ORF of any one or more of the sequences provided herein may be codon optimized. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g., glycosylation sites); add, remove or shuffle protein domains; insert or delete restriction sites; modify ribosome binding sites and mRNA degradation sites; adjust translational rates to allow the various domains of the protein to fold properly; or reduce or eliminate problem secondary structures within the polynucleotide. Codon optimization tools, algorithms and services are known in the art—non-limiting examples include services from GeneArt (Life Technologies), DNA2.0 (Menlo Park CA) and/or proprietary methods. In some embodiments, the open reading frame (ORF) sequence is optimized using optimization algorithms.

In some embodiments, a codon optimized sequence shares less than 95% sequence identity to a naturally occurring or wild-type sequence ORF (e.g., a naturally occurring or wild-type mRNA sequence encoding an EBV antigen). In some embodiments, a codon optimized sequence shares less than 90% sequence identity to a naturally occurring or wild-type sequence (e.g., a naturally occurring or wild-type mRNA sequence encoding an EBV antigen). In some embodiments, a codon optimized sequence shares less than 85% sequence identity to a naturally occurring or wild-type sequence (e.g., a naturally occurring or wild-type mRNA sequence encoding an EBV antigen). In some embodiments, a codon optimized sequence shares less than 80% sequence identity to a naturally occurring or wild-type sequence (e.g., a naturally occurring or wild-type mRNA sequence encoding an EBV antigen). In some embodiments, a codon optimized sequence shares less than 75% sequence identity to a naturally occurring or wild-type sequence (e.g., a naturally occurring or wild-type mRNA sequence encoding an EBV antigen).

In some embodiments, a codon optimized sequence shares between 65% and 85% (e.g., between about 67% and about 85% or between about 67% and about 80%) sequence identity to a naturally occurring or wild-type sequence (e.g., a naturally occurring or wild-type mRNA sequence encoding an EBV antigen). In some embodiments, a codon optimized sequence shares between 65% and 75% or about 80% sequence identity to a naturally occurring or wild-type sequence (e.g., a naturally occurring or wild-type mRNA sequence encoding an EBV antigen).

In some embodiments, a codon-optimized sequence encodes an antigen that is as immunogenic as, or more immunogenic than (e.g., at least 10%, at least 20%, at least 30%, at least 40%, at least 50%, at least 100%, or at least 200% more), than an EBV antigen encoded by a non-codon-optimized sequence.

When transfected into mammalian host cells, the modified mRNAs have a stability of between 12-18 hours, or greater than 18 hours, e.g., 24, 36, 48, 60, 72, or greater than 72 hours and are capable of being expressed by the mammalian host cells.

In some embodiments, a codon optimized mRNA may be one in which the levels of G/C are enhanced. The G/C-content of nucleic acid molecules (e.g., mRNA) may influence the stability of the mRNA. RNA having an increased amount of guanine (G) and/or cytosine (C) residues may be functionally more stable than mRNA containing a large amount of adenine (A) and thymine (T) or uracil (U) nucleotides. As an example, WO02/098443 discloses a pharmaceutical composition containing an mRNA stabilized by sequence modifications in the translated region. Due to the degeneracy of the genetic code, the modifications work by substituting existing codons for those that promote greater mRNA stability without changing the resulting amino acid. The approach is limited to coding regions of the mRNA.

Chemically Unmodified Nucleotides

In some embodiments, an mRNA is not chemically modified and comprises the standard ribonucleotides consisting of adenosine, guanosine, cytosine and uridine. In some embodiments, nucleotides and nucleosides of the present disclosure comprise standard nucleoside residues such as those present in transcribed mRNA (e.g., A, G, C, or U). In some embodiments, nucleotides and nucleosides of the present disclosure comprise standard deoxyribonucleosides such as those present in DNA (e.g., dA, dG, dC, or dT).

Chemical Modifications

The vaccines of the present disclosure comprise, in some embodiments, an mRNA having an open reading frame encoding an EBV antigen, wherein the nucleic acid comprises nucleotides and/or nucleosides that can be standard (unmodified) or modified as is known in the art. In some embodiments, nucleotides and nucleosides of the present disclosure comprise modified nucleotides or nucleosides. Such modified nucleotides and nucleosides can be naturally occurring modified nucleotides and nucleosides or non-naturally occurring modified nucleotides and nucleosides. Such modifications can include those at the sugar, backbone, or nucleobase portion of the nucleotide and/or nucleoside as are recognized in the art.

In some embodiments, a naturally occurring modified nucleotide or nucleotide of the disclosure is one as is generally known or recognized in the art. Non-limiting examples of such naturally occurring modified nucleotides and nucleotides can be found, inter alia, in the widely recognized MODOMICS database.

In some embodiments, a non-naturally occurring modified nucleotide or nucleoside of the disclosure is one as is generally known or recognized in the art. Non-limiting examples of such non-naturally occurring modified nucleotides and nucleosides can be found, inter alia, in published US application Nos. PCT/US2012/058519; PCT/US2013/075177; PCT/US2014/058897; PCT/US2014/058891; PCT/US2014/070413; PCT/US2015/36773; PCT/US2015/36759; PCT/US2015/36771; or PCT/IB2017/051367 all of which are incorporated by reference herein.

Hence, nucleic acids of the disclosure (e.g., DNA nucleic acids and RNA nucleic acids, such as mRNA nucleic acids) can comprise standard nucleotides and nucleosides, naturally occurring nucleotides and nucleosides, non-naturally occurring nucleotides and nucleosides, or any combination thereof.

Nucleic acids of the disclosure (e.g., DNA nucleic acids and RNA nucleic acids, such as mRNA nucleic acids), in some embodiments, comprise various (more than one) different types of standard and/or modified nucleotides and nucleosides. In some embodiments, a particular region of a nucleic acid contains one, two or more (optionally different) types of standard and/or modified nucleotides and nucleosides.

In some embodiments, a modified mRNA, introduced to a cell or organism, exhibits reduced degradation in the cell or organism, respectively, relative to an unmodified nucleic acid comprising standard nucleotides and nucleosides.

In some embodiments, a modified mRNA, introduced into a cell or organism, may exhibit reduced immunogenicity in the cell or organism, respectively (e.g., a reduced innate response) relative to an unmodified nucleic acid comprising standard nucleotides and nucleosides.

Nucleic acids (e.g., RNA nucleic acids, such as mRNA nucleic acids), in some embodiments, comprise non-natural modified nucleotides that are introduced during synthesis or post-synthesis of the nucleic acids to achieve desired functions or properties. The modifications may be present on internucleotide linkages, purine or pyrimidine bases, or sugars. The modification may be introduced with chemical synthesis or with a polymerase enzyme at the terminal of a chain or anywhere else in the chain. Any of the regions of a nucleic acid may be chemically modified.

The present disclosure provides for modified nucleosides and nucleotides of a nucleic acid (e.g., RNA nucleic acids, such as mRNA nucleic acids). A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside, including a phosphate group. Modified nucleotides may by synthesized by any useful method, such as, for example, chemically, enzymatically, or recombinantly, to include one or more modified or non-natural nucleosides. Nucleic acids can comprise a region or regions of linked nucleosides. Such regions may have variable backbone linkages. The linkages can be standard phosphodiester linkages, in which case the nucleic acids would comprise regions of nucleotides.

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures, such as, for example, in those nucleic acids having at least one chemical modification. One example of such non-standard base pairing is the base pairing between the modified nucleotide inosine and adenine, cytosine or uracil. Any combination of base/sugar or linker may be incorporated into nucleic acids of the present disclosure.

In some embodiments, modified nucleobases in nucleic acids (e.g., RNA nucleic acids, such as mRNA nucleic acids) comprise 1-methyl-pseudouridine (m1ψ), 1-ethyl-pseudouridine (e1ψ), 5-methoxy-uridine (mo5U), 5-methyl-cytidine (m5C), and/or pseudouridine (ψ). In some embodiments, modified nucleobases in nucleic acids (e.g., RNA nucleic acids, such as mRNA nucleic acids) comprise 5-methoxymethyl uridine, 5-methylthio uridine, 1-methoxymethyl pseudouridine, 5-methyl cytidine, and/or 5-methoxy cytidine. In some embodiments, the polyribonucleotide includes a combination of at least two (e.g., 2, 3, 4 or more) of any of the aforementioned modified nucleobases, including but not limited to chemical modifications.

In some embodiments, a mRNA of the disclosure comprises 1-methyl-pseudouridine (m1ψ) substitutions at one or more or all uridine positions of the nucleic acid.

In some embodiments, a mRNA of the disclosure comprises 1-methyl-pseudouridine (m1ψ) substitutions at one or more or all uridine positions of the nucleic acid and 5-methyl cytidine substitutions at one or more or all cytidine positions of the nucleic acid.

In some embodiments, a mRNA of the disclosure comprises pseudouridine (ψ) substitutions at one or more or all uridine positions of the nucleic acid.

In some embodiments, a mRNA of the disclosure comprises pseudouridine (ψ) substitutions at one or more or all uridine positions of the nucleic acid and 5-methyl cytidine substitutions at one or more or all cytidine positions of the nucleic acid.

In some embodiments, a mRNA of the disclosure comprises uridine at one or more or all uridine positions of the nucleic acid.

In some embodiments, mRNAs are uniformly modified (e.g., fully modified, modified throughout the entire sequence) for a particular modification. For example, a nucleic acid can be uniformly modified with 1-methyl-pseudouridine, meaning that all uridine residues in the mRNA sequence are replaced with 1-methyl-pseudouridin. Similarly, a nucleic acid can be uniformly modified for any type of nucleoside residue present in the sequence by replacement with a modified residue such as those set forth above.

The nucleic acids of the present disclosure may be partially or fully modified along the entire length of the molecule. For example, one or more or all or a given type of nucleotide (e.g., purine or pyrimidine, or any one or more or all of A. G. U. C) may be uniformly modified in a nucleic acid of the disclosure, or in a predetermined sequence region thereof (e.g., in the mRNA including or excluding the poly(A) tail). In some embodiments, all nucleotides X in a nucleic acid of the present disclosure (or in a sequence region thereof) are modified nucleotides, wherein X may be any one of nucleotides A, G. U. C, or any one of the combinations A+G, A+U, A+C, G+U, G+C, U+C, A+G+U, A+G+C, G+U+C or A+G+C.

The nucleic acid may contain from about 1% to about 100% modified nucleotides (either in relation to overall nucleotide content, or in relation to one or more types of nucleotide, i.e., any one or more of A. G. U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%). It will be understood that any remaining percentage is accounted for by the presence of unmodified A, G, U, or C.

The mRNAs may contain at a minimum 1% and at maximum 100% modified nucleotides, or any intervening percentage, such as at least 5% modified nucleotides, at least 10% modified nucleotides, at least 25% modified nucleotides, at least 50% modified nucleotides, at least 80% modified nucleotides, or at least 90% modified nucleotides. For example, the nucleic acids may contain a modified pyrimidine such as a modified uracil or cytosine. In some embodiments, at least 5%, at least 10%, at least 25%, at least 50%, at least 80%, at least 90% or 100% of the uracil in the nucleic acid is replaced with a modified uracil (e.g., a 5-substituted uracil). The modified uracil can be replaced by a compound having a single unique structure or can be replaced by a plurality of compounds having different structures (e.g., 2, 3, 4 or more unique structures). In some embodiments, at least 5%, at least 10%, at least 25%, at least 50%, at least 80%, at least 90% or 100% of the cytosine in the nucleic acid is replaced with a modified cytosine (e.g., a 5-substituted cytosine). The modified cytosine can be replaced by a compound having a single unique structure or can be replaced by a plurality of compounds having different structures (e.g., 2, 3, 4 or more unique structures).

Untranslated Regions (UTRs)

The mRNAs of the present disclosure may comprise one or more regions or parts which act or function as an untranslated region. Where mRNAs are designed to encode at least one antigen of interest, the nucleic may comprise one or more of these untranslated regions (UTRs). Wild-type untranslated regions of a nucleic acid are transcribed but not translated. In mRNA, the 5' UTR starts at the transcription start site and continues to the start codon but does not include the start codon; whereas the 3' UTR starts immediately following the stop codon and continues until the transcriptional termination signal. There is growing body of evidence about the regulatory roles played by the UTRs in terms of stability of the nucleic acid molecule and translation. The regulatory features of a UTR can be incorporated into the polynucleotides of the present disclosure to, among other things, enhance the stability of the molecule. The specific features can also be incorporated to ensure controlled down-regulation of the transcript in case they are misdirected to undesired organs sites. A variety of 5' UTR and 3' UTR sequences are known and available in the art.

A 5' UTR is region of an mRNA that is directly upstream (5') from the start codon (the first codon of an mRNA transcript translated by a ribosome). A 5' UTR does not encode a protein (is non-coding). Natural 5' UTRs have features that play roles in translation initiation. They harbor signatures like Kozak sequences which are commonly known to be involved in the process by which the ribosome initiates translation of many genes. Kozak sequences have the consensus CCR(A/G)CCAUGG (SEQ ID NO: 32), where R is a purine (adenine or guanine) three bases upstream of the start codon (AUG), which is followed by another 'G'. 5' UTRs also have been known to form secondary structures which are involved in elongation factor binding.

In some embodiments of the disclosure, a 5' UTR is a heterologous UTR, i.e., is a UTR found in nature associated with a different ORF. In another embodiment, a 5' UTR is a synthetic UTR, i.e., does not occur in nature. Synthetic UTRs include UTRs that have been mutated to improve their properties, e.g., which increase gene expression as well as those which are completely synthetic. Exemplary 5' UTRs include Xenopus or human derived a-globin or b-globin (U.S. Pat. Nos. 8,278,063; 9,012,219), human cytochrome b-245 a polypeptide, and hydroxysteroid (17b) dehydrogenase, and Tobacco etch virus (U.S. Pat. Nos. 8,278,063, 9,012,219). CMV immediate-early 1 (IE1) gene (US20140206753, WO2013/185069), the sequence GGGAUCCUACC (SEQ ID NO: 33) (WO2014144196) may also be used. In another embodiment, 5' UTR of a TOP gene is a 5' UTR of a TOP gene lacking the 5' TOP motif (the oligopyrimidine tract) (e.g., WO/2015101414, WO2015101415, WO/2015/062738, WO2015024667, WO2015024667; 5' UTR element derived from ribosomal protein Large 32 (L32) gene (WO/2015101414, WO2015101415, WO/2015/062738), 5' UTR element derived from the 5'UTR of an hydroxysteroid (17-β) dehydrogenase 4 gene (HSD17B4) (WO2015024667), or a 5' UTR element derived from the 5' UTR of ATP5A1 (WO2015024667) can be used. In some embodiments, an internal ribosome entry site (IRES) is used instead of a 5' UTR.

In some embodiments, a 5' UTR of the present disclosure comprises a sequence selected from SEQ ID NO: 1 and SEQ ID NO: 24.

A 3' UTR is region of an mRNA that is directly downstream (3') from the stop codon (the codon of an mRNA transcript that signals a termination of translation). A 3' UTR does not encode a protein (is non-coding). Natural or wild type 3' UTRs are known to have stretches of adenosines and uridines embedded in them. These AU rich signatures are particularly prevalent in genes with high rates of turnover. Based on their sequence features and functional properties, the AU rich elements (AREs) can be separated into three classes (Chen et al, 1995): Class I AREs contain several dispersed copies of an AUUUA motif within U-rich regions. C-Myc and MyoD contain class I AREs. Class II AREs possess two or more overlapping UUAUUUA(U/A)(U/A) (SEQ ID NO: 34) nonamers. Molecules containing this type of AREs include GM-CSF and TNF-a. Class III ARES are less well defined. These U rich regions do not contain an AUUUA motif. c-Jun and Myogenin are two well-studied examples of this class. Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo.

Introduction, removal or modification of 3' UTR AU rich elements (AREs) can be used to modulate the stability of nucleic acids (e.g., mRNA) of the disclosure. When engineering specific nucleic acids, one or more copies of an ARE can be introduced to make nucleic acids of the disclosure less stable and thereby curtail translation and decrease production of the resultant protein. Likewise, AREs can be identified and removed or mutated to increase the intracellular stability and thus increase translation and production of the resultant protein. Transfection experiments can be conducted in relevant cell lines, using nucleic acids of the disclosure and protein production can be assayed at various time points post-transfection. For example, cells can be transfected with different ARE-engineering molecules and by using an ELISA kit to the relevant protein and assaying protein produced at 6 hours, 12 hours, 24 hours, 48 hours, 3 days, 4 days, 5 days, 6 days, and/or 7 days post-transfection.

Figure 4A:
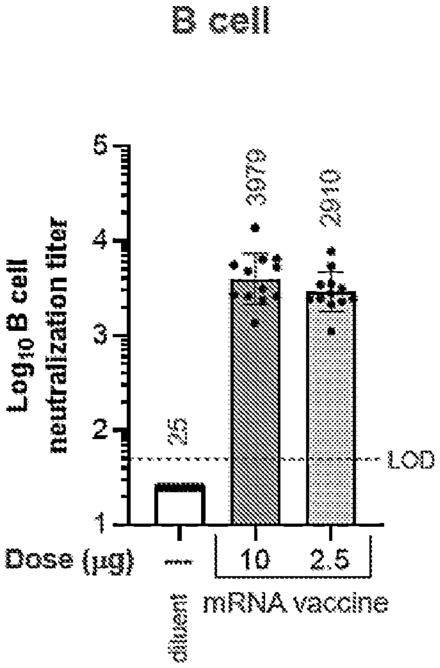
FIGS. 4A-4B include graphs showing antibodies against B cell infection (FIG. 4A) and against epithelial cell infection (FIG. 4B) observed in preclinical studies using Balb/c mice and two different doses of mRNA vaccine: 10 μg (5.33 μg mRNA encoding EBV gp220, 2 μg mRNA encoding EBV gH, 1.33 μg mRNA encoding EBV gL, 1.33 μg mRNA encoding EBV sgp42) and 2.5 μg (1.33 μg mRNA encoding EBV gp220, 0.5 μg mRNA encoding EBV gH, 0.33 μg mRNA encoding EBV gL, 0.33 μg mRNA encoding EBV sgp42). The mRNA vaccine was immunogenic at both doses, raising B cell and epithelial cell neutralizing antibodies (gHgL, gp220 and gp42).

3' UTRs may be heterologous or synthetic. With respect to 3' UTRs, globin UTRs, including Xenopus β-globin UTRs and human β-globin UTRs are known in the art (U.S. Pat. Nos. 8,278,063, 9,012,219, US20110086907). A nucleic acid (e.g., mRNA) encoding a modified β-globin with enhanced stability in some cell types by cloning two sequential human β-globin 3' UTRs head to tail has been developed and is well known in the art (US2012/0195936, WO2014/071963). In addition, a2-globin, a1-globin, UTRs and mutants thereof are also known in the art (WO2015101415, WO2015024667). Other 3' UTRs described in the mRNA in the non-patent literature include CYBA (Ferizi et al., 2015) and albumin (Thess et al., 2015). Other exemplary 3' UTRs include that of bovine or human growth hormone (wild type or modified) (WO2013/185069, US20140206753, WO2014152774), rabbit β globin and hepatitis B virus (HBV), α-globin 3' UTR and Viral VEEV 3' UTR sequences are also known in the art. In some embodiments, the sequence UUUGAAUU (WO2014144196) is used. In some embodiments, 3' UTRs of human and mouse ribosomal protein are used. Other examples include rps9 3' UTR (WO2015101414), FIG. 4 (WO2015101415), and human albumin 7 (WO2015101415).

In some embodiments, a 3' UTR of the present disclosure comprises a sequence selected from SEQ ID NO: 3 and SEQ ID NO: 25.

Those of ordinary skill in the art will understand that 5' UTRs that are heterologous or synthetic may be used with any desired 3' UTR sequence. For example, a heterologous 5' UTR may be used with a synthetic 3' UTR with a heterologous 3' UTR.

Non-UTR sequences may also be used as regions or subregions within a nucleic acid. For example, introns or portions of introns sequences may be incorporated into regions of nucleic acid of the disclosure. Incorporation of intronic sequences may increase protein production as well as nucleic acid levels.

Combinations of features may be included in flanking regions and may be contained within other features. For example, the ORF may be flanked by a 5' UTR which may contain a strong Kozak translational initiation signal and/or a 3' UTR which may include an oligo(dT) sequence for templated addition of a poly-A tail. 5' UTR may comprise a first polynucleotide fragment and a second polynucleotide fragment from the same and/or different genes such as the 5' UTRs described in US Patent Application Publication No. 20100293625 and PCT/US2014/069155, herein incorporated by reference in its entirety.

It should be understood that any UTR from any gene may be incorporated into the regions of a nucleic acid. Furthermore, multiple wild-type UTRs of any known gene may be utilized. It is also within the scope of the present disclosure to provide artificial UTRs which are not variants of wild type regions. These UTRs or portions thereof may be placed in the same orientation as in the transcript from which they were selected or may be altered in orientation or location. Hence a 5' or 3' UTR may be inverted, shortened, lengthened, made with one or more other 5' UTRs or 3' UTRs. As used herein, the term "altered" as it relates to a UTR sequence, means that the UTR has been changed in some way in relation to a reference sequence. For example, a 3' UTR or 5' UTR may be altered relative to a wild-type or native UTR by the change in orientation or location as taught above or may be altered by the inclusion of additional nucleotides, deletion of nucleotides, swapping or transposition of nucleotides. Any of these changes producing an "altered" UTR (whether 3' or 5') comprise a variant UTR.

In some embodiments, a double, triple or quadruple UTR such as a 5' UTR or 3' UTR may be used. As used herein, a "double" UTR is one in which two copies of the same UTR are encoded either in series or substantially in series. For example, a double beta-globin 3' UTR may be used as described in US Patent publication 20100129877, the contents of which are incorporated herein by reference in its entirety.

It is also within the scope of the present disclosure to have patterned UTRs. As used herein "patterned UTRs" are those UTRs which reflect a repeating or alternating pattern, such as ABABAB or AABBAABBAABB or ABCABCABC or variants thereof repeated once, twice, or more than 3 times. In these patterns, each letter, A, B, or C represent a different UTR at the nucleotide level.

In some embodiments, flanking regions are selected from a family of transcripts whose proteins share a common function, structure, feature or property. For example, polypeptides of interest may belong to a family of proteins which are expressed in a particular cell, tissue or at some time during development. The UTRs from any of these genes may be swapped for any other UTR of the same or different family of proteins to create a new polynucleotide. As used herein, a "family of proteins" is used in the broadest sense to refer to a group of two or more polypeptides of interest which share at least one function, structure, feature, localization, origin, or expression pattern.

The untranslated region may also include translation enhancer elements (TEE). As a non-limiting example, the TEE may include those described in US Application No. 20090226470, herein incorporated by reference in its entirety, and those known in the art.

In Vitro Transcription of mRNA cDNA encoding the polynucleotides described herein may be transcribed using an in vitro transcription (IVT) system. In vitro transcription of mRNA is known in the art and is described in International Publication WO/2014/152027, which is incorporated by reference herein in its entirety.

In some embodiments, the mRNA transcript is generated using a non-amplified, linearized DNA template in an in vitro transcription reaction to generate the mRNA transcript. In some embodiments, the template DNA is isolated DNA. In some embodiments, the template DNA is cDNA. In some embodiments, the cDNA is formed by reverse transcription of a mRNA, for example, but not limited to EBV mRNA. In some embodiments, cells, e.g., bacterial cells, e.g., *E. coli*, e.g., DH-1 cells are transfected with the plasmid DNA template. In some embodiments, the transfected cells are cultured to replicate the plasmid DNA which is then isolated and purified. In some embodiments, the DNA template includes an RNA polymerase promoter, e.g., a T7 promoter located 5' to and operably linked to the gene of interest.

In some embodiments, an in vitro transcription template encodes a 5' untranslated (UTR) region, contains an open reading frame, and encodes a 3' UTR and a poly(A) tail. The particular nucleic acid sequence and length of an in vitro transcription template will depend on the mRNA encoded by the template.

A "5' untranslated region" (UTR) refers to a region of an mRNA that is directly upstream (i.e., 5') from the start codon (i.e., the first codon of an mRNA transcript translated by a ribosome) that does not encode a polypeptide. When mRNA transcripts are being generated, the 5' UTR may comprise a promoter sequence. Such promoter sequences are known in the art. It should be understood that such promoter sequences will not be present in a vaccine of the disclosure.

A "3' untranslated region" (UTR) refers to a region of an mRNA that is directly downstream (i.e., 3') from the stop codon (i.e., the codon of an mRNA transcript that signals a termination of translation) that does not encode a polypeptide.

An "open reading frame" is a continuous stretch of DNA beginning with a start codon (e.g., methionine (ATG)), and ending with a stop codon (e.g., TAA, TAG or TGA) and encodes a polypeptide.

A "poly(A) tail" is a region of mRNA that is downstream, e.g., directly downstream (i.e., 3'), from the 3' UTR that contains multiple, consecutive adenosine monophosphates. A poly(A) tail may contain 10 to 300 adenosine monophosphates. For example, a poly(A) tail may contain 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300 adenosine monophosphates. In some embodiments, a poly(A) tail contains 50 to 250 adenosine monophosphates. In a relevant biological setting (e.g., in cells, in vivo) the poly(A) tail functions to protect mRNA from enzymatic degradation, e.g., in the cytoplasm, and aids in transcription termination, and/or export of the mRNA from the nucleus and translation.

In some embodiments, a nucleic acid includes 200 to 3,000 nucleotides. For example, a nucleic acid may include 200 to 500, 200 to 1000, 200 to 1500, 200 to 3000, 500 to 1000, 500 to 1500, 500 to 2000, 500 to 3000, 1000 to 1500, 1000 to 2000, 1000 to 3000, 1500 to 3000, or 2000 to 3000 nucleotides).

An in vitro transcription system typically comprises a transcription buffer, nucleotide triphosphates (NTPs), an RNase inhibitor and a polymerase.

The NTPs may be manufactured in house, may be selected from a supplier, or may be synthesized as described herein. The NTPs may be selected from, but are not limited to, those described herein including natural and unnatural (modified) NTPs.

Any number of RNA polymerases or variants may be used in the method of the present disclosure. The polymerase may be selected from, but is not limited to, a phage RNA polymerase, e.g., a T7 RNA polymerase, a T3 RNA polymerase, a SP6 RNA polymerase, and/or 5 mutant polymerases such as, but not limited to, polymerases able to incorporate modified nucleic acids and/or modified nucleotides, including chemically modified nucleic acids and/or nucleotides. Some embodiments exclude the use of DNase.

In some embodiments, the mRNA transcript is capped via enzymatic capping. In some embodiments, the mRNA comprises 5' terminal cap, for example, 7mG(5')ppp(5')NlmpNp.

Chemical Synthesis

Solid-phase chemical synthesis. Nucleic acids the present disclosure may be manufactured in whole or in part using solid phase techniques. Solid-phase chemical synthesis of nucleic acids is an automated method wherein molecules are immobilized on a solid support and synthesized step by step in a reactant solution. Solid-phase synthesis is useful in site-specific introduction of chemical modifications in the nucleic acid sequences.

Liquid Phase Chemical Synthesis. The synthesis of nucleic acids of the present disclosure by the sequential addition of monomer building blocks may be carried out in a liquid phase.

Combination of Synthetic Methods. The synthetic methods discussed above each has its own advantages and limitations. Attempts have been conducted to combine these methods to overcome the limitations. Such combinations of methods are within the scope of the present disclosure. The use of solid-phase or liquid-phase chemical synthesis in combination with enzymatic ligation provides an efficient way to generate long chain nucleic acids that cannot be obtained by chemical synthesis alone.

Ligation of Nucleic Acid Regions or Subregions

Assembling nucleic acids by a ligase may also be used. DNA or RNA ligases promote intermolecular ligation of the 5' and 3' ends of polynucleotide chains through the formation of a phosphodiester bond. Nucleic acids such as chimeric polynucleotides and/or circular nucleic acids may be prepared by ligation of one or more regions or subregions. DNA fragments can be joined by a ligase catalyzed reaction to create recombinant DNA with different functions. Two oligodeoxynucleotides, one with a 5' phosphoryl group and another with a free 3' hydroxyl group, serve as substrates for a DNA ligase.

Purification

Purification of the nucleic acids described herein may include, but is not limited to, nucleic acid clean-up, quality assurance and quality control. Clean-up may be performed by methods known in the arts such as, but not limited to, AGENCOURT® beads (Beckman Coulter Genomics, Danvers, MA), poly-T beads, LNA™ oligo-T capture probes (EXIQON® Inc, Vedback, Denmark) or HPLC based purification methods such as, but not limited to, strong anion exchange HPLC, weak anion exchange HPLC, reverse phase HPLC (RP-HPLC), and hydrophobic interaction HPLC (HIC-HPLC). The term "purified" when used in relation to a nucleic acid such as a "purified nucleic acid" refers to one that is separated from at least one contaminant. A "contaminant" is any substance that makes another unfit, impure or inferior. Thus, a purified nucleic acid (e.g., DNA and RNA) is present in a form or setting different from that in which it is found in nature, or a form or setting different from that which existed prior to subjecting it to a treatment or purification method.

A quality assurance and/or quality control check may be conducted using methods such as, but not limited to, gel electrophoresis, UV absorbance, or analytical HPLC.

In some embodiments, the nucleic acids may be sequenced by methods including, but not limited to reverse-transcriptase-PCR.

Quantification

In some embodiments, the nucleic acids of the present disclosure may be quantified in exosomes or when derived from one or more bodily fluid. Bodily fluids include peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. Alternatively, exosomes may be retrieved from an organ selected from the group consisting of lung, heart, pancreas, stomach, intestine, bladder, kidney, ovary, testis, skin, colon, breast, prostate, brain, esophagus, liver, and placenta.

Assays may be performed using antigen-specific probes, cytometry, qRT-PCR, real-time PCR, PCR, flow cytometry, electrophoresis, mass spectrometry, or combinations thereof while the exosomes may be isolated using immunohistochemical methods such as enzyme linked immunosorbent assay (ELISA) methods. Exosomes may also be isolated by size exclusion chromatography, density gradient centrifugation, differential centrifugation, nanomembrane ultrafiltration, immunosorbent capture, affinity purification, microfluidic separation, or combinations thereof.

These methods afford the investigator the ability to monitor, in real time, the level of nucleic acids remaining or delivered. This is possible because the nucleic acids of the present disclosure, in some embodiments, differ from the endogenous forms due to the structural or chemical modifications.

In some embodiments, the nucleic acid may be quantified using methods such as, but not limited to, ultraviolet visible spectroscopy (UV/Vis). A non-limiting example of a UV/Vis spectrometer is a NANODROP® spectrometer (ThermoFisher, Waltham, MA). The quantified nucleic acid may be analyzed in order to determine if the nucleic acid may be of proper size, check that no degradation of the nucleic acid has occurred. Degradation of the nucleic acid may be checked by methods such as, but not limited to, agarose gel electrophoresis, HPLC based purification methods such as, but not limited to, strong anion exchange HPLC, weak anion exchange HPLC, reverse phase HPLC (RP-HPLC), and hydrophobic interaction HPLC (HIC-HPLC), liquid chromatography-mass spectrometry (LCMS), capillary electrophoresis (CE) and capillary gel electrophoresis (CGE).

Lipid Nanoparticles (LNPs)

In some embodiments, the mRNA of the disclosure is formulated in a lipid nanoparticle (LNP). Lipid nanoparticles typically comprise ionizable amino lipid, non-cationic lipid, sterol and PEG lipid components along with the nucleic acid cargo of interest. The lipid nanoparticles of the disclosure can be generated using components, compositions, and methods as are generally known in the art, see for example PCT/US2016/052352; PCT/US2016/068300; PCT/US2017/037551; PCT/US2015/027400; PCT/US2016/047406; PCT/US2016/000129; PCT/US2016/014280; PCT/US2016/014280; PCT/US2017/038426; PCT/US2014/027077; PCT/US2014/055394; PCT/US2016/052117; PCT/US2012/069610; PCT/US2017/027492; PCT/US2016/059575 and PCT/US2016/069491 all of which are incorporated by reference herein in their entirety.

Vaccines of the present disclosure are typically formulated in lipid nanoparticles. The vaccines can be made, for example, using mixing processes such as microfluidics and T-junction mixing of two fluid streams, one of which contains the mRNA and the other has the lipid components. In some embodiments, the vaccines are prepared by combining an ionizable amino lipid, a phospholipid (such as DOPE or DSPC), a PEG lipid (such as 1,2-dimyristoyl-OT-glycerol methoxypoly ethylene glycol, also known as PEG-DMG), and a structural lipid (such as cholesterol) in an alcohol (e.g., ethanol). The lipids may be combined to yield desired molar ratios and diluted with water and alcohol (e.g., ethanol) to a final lipid concentration of between about 5.5 mM and about 25 mM, for example.

Vaccines including mRNA and a lipid component may be prepared, for example, by combining a lipid solution with an mRNA solution at lipid component to mRNA wt:wt ratios of between about 5:1 and about 50:1. The lipid solution may be rapidly injected using a microfluidic based system (e.g., NanoAssemblr) at flow rates between about 10 ml/min and about 18 ml/min, for example, into the mRNA solution to produce a suspension (e.g., with a water to alcohol ratio between about 1:1 and about 4:1).

Vaccines can be processed by dialysis to remove the alcohol (e.g., ethanol) and achieve buffer exchange. Formulations may be dialyzed against phosphate buffered saline (PBS), pH 7.4, for example, at volumes greater than that of the primary product (e.g., using Slide-A-Lyzer cassettes (Thermo Fisher Scientific Inc., Rockford, IL)) with a molecular weight cutoff of 10 kD, for example. The forgoing exemplary method induces nanoprecipitation and particle formation. Alternative processes including, but not limited to, T-junction and direct injection, may be used to achieve the same nanoprecipitation.

In some embodiments, the lipid nanoparticle comprises at least one ionizable amino (cationic) lipid, at least one non-cationic lipid, at least one sterol, and/or at least one polyethylene glycol (PEG)-modified lipid.

In some embodiments, the lipid nanoparticle comprises 20-60 mol % ionizable amino lipid. For example, the lipid nanoparticle may comprise 20-50 mol %, 20-40 mol %, 20-30 mol %, 30-60 mol %, 30-50 mol %, 30-40 mol %, 40-60 mol %, 40-50 mol %, or 50-60 mol % ionizable amino lipid. In some embodiments, the lipid nanoparticle comprises 20 mol %, 30 mol %, 40 mol %, 50, or 60 mol % ionizable amino lipid.

In some embodiments, the lipid nanoparticle comprises 5-25 mol % non-cationic lipid. For example, the lipid nanoparticle may comprise 5-20 mol %, 5-15 mol %, 5-10 mol %, 10-25 mol %, 10-20 mol %, 10-25 mol %, 15-25 mol %, 15-20 mol %, or 20-25 mol % non-cationic lipid. In some embodiments, the lipid nanoparticle comprises 5 mol %, 10 mol %, 15 mol %, 20 mol %, or 25 mol % non-cationic lipid.

In some embodiments, the lipid nanoparticle comprises 25-55 mol % sterol. For example, the lipid nanoparticle may comprise 25-50 mol %, 25-45 mol %, 25-40 mol %, 25-35 mol %, 25-30 mol %, 30-55 mol %, 30-50 mol %, 30-45 mol %, 30-40 mol %, 30-35 mol %, 35-55 mol %, 35-50 mol %, 35-45 mol %, 35-40 mol %, 40-55 mol %, 40-50 mol %, 40-45 mol %, 45-55 mol %, 45-50 mol %, or 50-55 mol % sterol. In some embodiments, the lipid nanoparticle comprises 25 mol %, 30 mol %, 35 mol %, 40 mol %, 45 mol %, 50 mol %, or 55 mol % sterol.

In some embodiments, the lipid nanoparticle comprises 0.5-15 mol % PEG-modified lipid. For example, the lipid nanoparticle may comprise 0.5-10 mol %, 0.5-5 mol %, 1-15 mol %, 1-10 mol %, 1-5 mol %, 2-15 mol %, 2-10 mol %, 2-5 mol %, 5-15 mol %, 5-10 mol %, or 10-15 mol %. In some embodiments, the lipid nanoparticle comprises 0.5 mol %, 1 mol %, 2 mol %, 3 mol %, 4 mol %, 5 mol %, 6 mol %, 7 mol %, 8 mol %, 9 mol %, 10 mol %, 11 mol %, 12 mol %, 13 mol %, 14 mol %, or 15 mol % PEG-modified lipid.

In some embodiments, the lipid nanoparticle comprises 20-60 mol % ionizable amino lipid, 5-25 mol % non-cationic lipid, 25-55 mol % sterol, and 0.5-15 mol % PEG-modified lipid.

In some embodiments, an ionizable amino lipid of the disclosure comprises a compound of Formula (I):

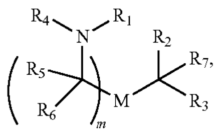

(I)

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a carbocycle, heterocycle, —OR, $—O(CH_2)_nN(R)_2$, —C(O)OR, —OC(O)R, $—CX_3$, $—CX_2H$, $—CXH_2$, —CN, $—N(R)_2$, $—C(O)N(R)_2$, —N(R)C(O)R, $—N(R)S(O)_2R$, $—N(R)C(O)N(R)_2$, $—N(R)C(S)N(R)_2$, $—N(R)R_8$, $—O(CH_2)_nOR$, $—N(R)C(═NR_9)N(R)_2$, $—N(R)C(═CHR_9)N(R)_2$, $—OC(O)N(R)_2$, —N(R)C(O)OR, —N(OR)C(O)R, $—N(OR)S(O)_2R$, —N(OR)C(O)OR, $—N(OR)C(O)N(R)_2$, $—N(OR)C(S)N(R)_2$, $—N(OR)C(═NR_9)N(R)_2$, $—N(OR)C(═CHR_9)N(R)_2$, $—C(═NR_9)N(R)_2$, $—C(═NR_9)R$, —C(O)N(R)OR, and $—C(R)N(R)_2C(O)OR$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, $—S(O)_2R$, $—S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

In some embodiments, a subset of compounds of Formula (I) includes those in which when $R_4$ is $—(CH_2)_bQ$, $—(CH_2)_nCHQR$, —CHQR, or $—CQ(R)_2$, then (i) Q is not $—N(R)_2$ when n is 1, 2, 3, 4 or 5, or (ii) Q is not 5, 6, or 7-membered heterocycloalkyl when n is 1 or 2.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR. $—O(CH_2)_nN(R)_2$, —C(O)OR, —OC(O)R, $—CX_3$, $—CX_2H$, $—CXH_2$, —CN, $—C(O)N(R)_2$, —N(R)C(O)R, $—N(R)S(O)_2R$, $—N(R)C(O)N(R)_2$, $—N(R)C(S)N(R)_2$, $—CRN(R)_2C(O)OR$, $—N(R)R_8$, $—O(CH_2)_nOR$, $—N(R)C(═NR_9)N(R)_2$, $—N(R)C(═CHR_9)N(R)_2$, $—OC(O)N(R)_2$, —N(R)C(O)OR, —N(OR)C(O)R, $—N(OR)S(O)_2R$, —N(OR)C(O)OR, $—N(OR)C(O)N(R)_2$, $—N(OR)C(S)N(R)_2$, $—N(OR)C(═NR_9)N(R)_2$. $—N(OR)C(═CHR_9)N(R)_2$, $—C(═NR_9)N(R)_2$, $—C(═NR_9)R$, —C(O)N(R)OR, and a 5- to 14-membered heterocycloalkyl having one or more heteroatoms selected from N, O, and S which is substituted with one or more substituents selected from oxo (═O), OH, amino, mono- or di-alkylamino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, $—S(O)_2R$, $—S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —CQ$(R)_2$, and unsubstituted $C_{1-6}$ alkyl, where Q is selected from a $C_{3-6}$ carbocycle, a 5- to 14-membered heterocycle having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —C(O)$N(R)_2$, —N(R)C(O)R, —N(R)$S(O)_2$R, —N(R)C(O)N$(R)_2$, —N(R)C(S)N$(R)_2$, —CRN$(R)_2$C(O)OR, —N(R)$R_8$, —$O(CH_2)_n$OR, —N(R)C(═$NR_9$)N$(R)_2$, —N(R)C(═$CHR_9$)N$(R)_2$, —OC(O)N$(R)_2$, —N(R)C(O)OR, —N(OR)C(O)R, —N(OR)$S(O)_2$R, —N(OR)C(O)OR, —N(OR)C(O)N$(R)_2$, —N(OR)C(S)N$(R)_2$, —N(OR)C(═$NR_9$)N$(R)_2$, —N(OR)C(═$CHR_9$)N$(R)_2$, —C(═$NR_9$)R, —C(O)N(R)OR, and —C(═$NR_9$)N$(R)_2$, and each n is independently selected from 1, 2, 3, 4, and 5; and when Q is a 5- to 14-membered heterocycle and (i) $R_4$ is —$(CH_2)_n$Q in which n is 1 or 2, or (ii) $R_4$ is —$(CH_2)_n$CHQR in which n is 1, or (iii) $R_4$ is —CHQR, and —CQ$(R)_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2$R, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —CQ$(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —C(O)N$(R)_2$, —N(R)C(O)R, —N(R)$S(O)_2$R, —N(R)C(O)N$(R)_2$, —N(R)C(S)N$(R)_2$, —CRN$(R)_2$C(O)OR, —N(R)$R_8$, —$O(CH_2)_n$OR, —N(R)C(═$NR_9$)N$(R)_2$, —N(R)C(═$CHR_9$)N$(R)_2$, —OC(O)N$(R)_2$, —N(R)C(O)OR, —N(OR)C(O)R, —N(OR)$S(O)_2$R, —N(OR)C(O)OR, —N(OR)C(O)N$(R)_2$, —N(OR)C(S)N$(R)_2$, —N(OR)C(═$NR_9$)N$(R)_2$, —N(OR)C(═$CHR_9$)N$(R)_2$, —C(═$NR_9$)R, —C(O)N(R)OR, and —C(═$NR_9$)N$(R)_2$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2$R, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is —$(CH_2)_n$Q or —$(CH_2)_n$CHQR, where Q is —N$(R)_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of —$(CH_2)_n$Q, —$(CH_2)_n$CHQR, —CHQR, and —$CQ(R)_2$, where Q is —$N(R)_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those of Formula (IA):

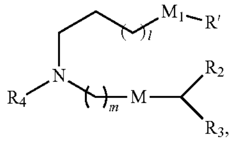

(IA)

or a salt or isomer thereof, wherein 1 is selected from 1, 2, 3, 4, and 5; m is selected from 5, 6, 7, 8, and 9; $M_1$ is a bond or M'; $R_4$ is unsubstituted $C_{1-3}$ alkyl, or —$(CH_2)_n$Q, in which Q is OH, —NHC(S)$N(R)_2$, —NHC(O)$N(R)_2$, —N(R)C(O)R, —N(R)$S(O)_2$R, —N(R)$R_8$, —NHC(=$NR_9$)$N(R)_2$, —NHC(=$CHR_9$)$N(R)_2$, —OC(O)$N(R)_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (II):

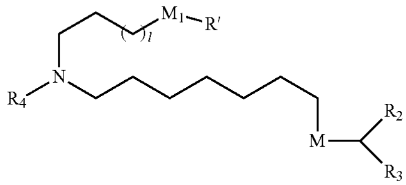

(II)

or a salt or isomer thereof, wherein 1 is selected from 1, 2, 3, 4, and 5; $M_1$ is a bond or M'; $R_4$ is unsubstituted $C_{1-3}$ alkyl, or —$(CH_2)$»Q, in which n is 2, 3, or 4, and Q is OH, —NHC(S)$N(R)_2$, —NHC(O)$N(R)_2$, —N(R)C(O)R, —N(R)$S(O)_2$R, —N(R)$R_8$, —NHC(=$NR_9$)$N(R)_2$, —NHC(=$CHR_9$)$N(R)_2$, —OC(O)$N(R)_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (IIa), (IIb), (IIc), or (IIe):

(IIa)

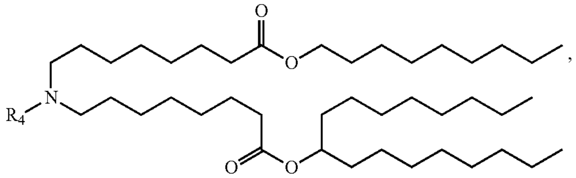

(IIb)

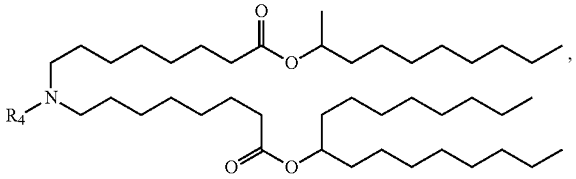

-continued (IIc)

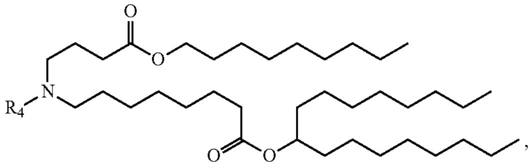

, or (IIe)

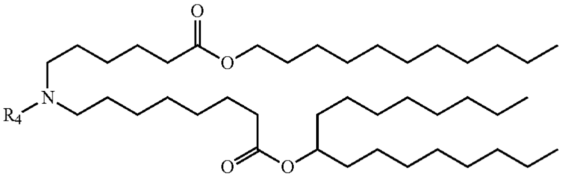

, or a salt or isomer thereof, wherein $R_4$ is as described herein.

In some embodiments, a subset of compounds of Formula (I) includes those of Formula (IId):

(IId)

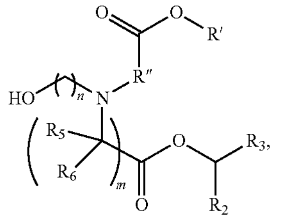

or a salt or isomer thereof, wherein n is 2, 3, or 4; and m, R', R", and $R_2$ through $R_6$ are as described herein. For example, each of $R_2$ and $R_3$ may be independently selected from the group consisting of $C_{5-14}$ alkyl and $C_{5-14}$ alkenyl.

In some embodiments, an ionizable amino lipid of the disclosure comprises a compound having structure:

(Compound I)

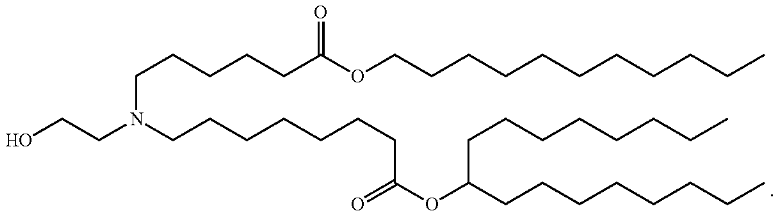

.

In some embodiments, an ionizable amino lipid of the disclosure comprises a compound having structure:

(Compound II)

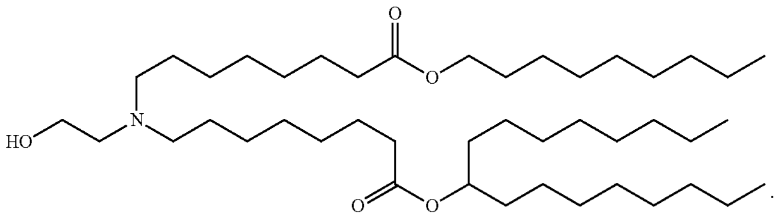

.

In some embodiments, a non-cationic lipid of the disclosure comprises 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-gly cero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2 cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-diolcoyl-sn-glycero-3-phospho-rac-(1-glycerol) sodium salt (DOPG), sphingomyelin, and mixtures thereof.

In some embodiments, a PEG modified lipid of the disclosure comprises a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof. In some embodiments, the PEG-modified lipid is DMG-PEG, PEG-c-DOMG (also referred to as PEG-DOMG), PEG-DSG and/or PEG-DPG.

In some embodiments, a sterol of the disclosure comprises cholesterol, fecosterol, sitosterol, ergosterol, campesterol, stigmasterol, brassicasterol, tomatidine, ursolic acid, alpha-tocopherol, and mixtures thereof.

In some embodiments, a LNP of the disclosure comprises an ionizable amino lipid of Compound 1, wherein the non-cationic lipid is DSPC, the structural lipid that is cholesterol, and the PEG lipid is DMG-PEG.

In some embodiments, the lipid nanoparticle comprises 45-55 mole percent ionizable amino lipid. For example, lipid nanoparticle may comprise 45, 46, 47, 48, 49, 50, 51, 52, 53, 54, or 55 mole percent ionizable amino lipid.

In some embodiments, the lipid nanoparticle comprises 5-15 mole percent DSPC. For example, the lipid nanoparticle may comprise 5, 6, 7, 8, 9, 10, 11, 12, 13, 14, or 15 mole percent DSPC.

In some embodiments, the lipid nanoparticle comprises 35-40 mole percent cholesterol. For example, the lipid nanoparticle may comprise 35, 36, 37, 38, 39, or 40 mole percent cholesterol.

In some embodiments, the lipid nanoparticle comprises 1-2 mole percent DMG-PEG. For example, the lipid nanoparticle may comprise 1, 1.5, or 2 mole percent DMG-PEG.

In some embodiments, the lipid nanoparticle comprises 50 mole percent ionizable amino lipid, 10 mole percent DSPC, 38.5 mole percent cholesterol, and 1.5 mole percent DMG-PEG.

In some embodiments, a LNP of the disclosure comprises an N:P ratio of from about 2:1 to about 30:1.

In some embodiments, a LNP of the disclosure comprises an N:P ratio of about 6:1.

In some embodiments, a LNP of the disclosure comprises an N:P ratio of about 3:1.

In some embodiments, a LNP of the disclosure comprises a wt/wt ratio of the ionizable amino lipid component to the mRNA of from about 10:1 to about 100:1.

In some embodiments, a LNP of the disclosure comprises a wt/wt ratio of the ionizable amino lipid component to the mRNA of about 20:1.

In some embodiments, a LNP of the disclosure comprises a wt/wt ratio of the ionizable amino lipid component to the mRNA of about 10:1.

In some embodiments, a LNP of the disclosure has a mean diameter from about 50 nm to about 150 nm.

In some embodiments, a LNP of the disclosure has a mean diameter from about 70 nm to about 120 nm.

Multivalent Vaccines

The vaccines, as provided herein, include multiple mRNAs, each encoding one or more EBV antigens. In some embodiments, a vaccine includes 1, 2, 3, 4, 5, 6, 7, 8, 9, 10, 11, 12, or more mRNAs encoding EBV antigens.

In some embodiments, two or more different mRNA encoding antigens may be formulated in the same lipid nanoparticle. In other embodiments, two or more different mRNA encoding antigens may be formulated in separate lipid nanoparticles (each mRNA formulated in a single lipid nanoparticle). The lipid nanoparticles may then be combined and administered as a single vaccine (e.g., comprising multiple mRNA encoding multiple antigens) or may be administered separately.

In some embodiments, the EBV vaccines provided herein include a first mRNA encoding EBV gp220, a second mRNA encoding EBV gp42 (soluble or wild type), a third mRNA encoding EBV gH, and a fourth mRNA encoding EBV gL. In some embodiments, the EBV vaccine further comprises a fifth mRNA encoding EBV gB.

Multivalent mRNAs are typically produced by transcribing one mRNA at a time, purifying each mRNA, and then mixing the purified mRNA together prior to formulation.

In some embodiments, a vaccine comprises (a) a first mRNA comprising an open reading frame encoding EBV glycoprotein 220 (gp220); (b) a second mRNA comprising an open reading frame encoding glycoprotein 42 (gp42) (e.g., a soluble form of gp42); (c) a third mRNA comprising an open reading frame encoding glycoprotein L (gL); and (d) a fourth mRNA comprising an open reading frame encoding glycoprotein H (gH).

In some embodiments, the mass ratio of (a):(b) is 4:1, 4:1.5, 2:1, 4:2.5, 4:3, 4:3.5, or 1:1. In some embodiments, the mass ratio of (a):(c) 4:1, 4:1.5, 2:1, 4:2.5, 4:3, 4:3.5, or 1:1. In some embodiments, the mass ratio of (a):(d) 4:1, 4:1.5, 2:1, 4:2.5, 4:3, 4:3.5, or 1:1.

In some embodiments, the mass ratio of (b):(c) is 2:1, 2:1.5, 1:1, 1:1.5, or 1:2. In some embodiments, the ratio of (b):(d) is 2:1, 2:1.5, 1:1, 1:1.5, or 1:2.

In some embodiments, the mass ratio of (c):(d) is 2:1, 2:1.5, 1:1, 1:1.5, or 1:2.

In some embodiments, the mass ratio of (a):(b):(c):(d) is 4:1:1:1.5. In some embodiments, the mass ratio of (a):(b):(c):(d) is 4:1:1:1.

In some embodiments, a vaccine comprises mRNA encoding EBV gp220 at 5×, 4.5×, 4×, 3.5×, 3×, 2.5×, 2×, or 1.5× the mRNA encoding EBV gp42. In some embodiments, a vaccine comprises mRNA encoding EBV gp220 at equal mass to the mRNA encoding EBV gp42.

In some embodiments, a vaccine comprises mRNA encoding EBV gp220 at 5×, 4.5×, 4×, 3.5×, 3×, 2.5×, 2×, or 1.5× the mRNA encoding EBV gL. In some embodiments, a vaccine comprises mRNA encoding EBV gp220 at equal mass to the mRNA encoding EBV gL.

In some embodiments, a vaccine comprises mRNA encoding EBV gp220 at 5×, 4.5×, 4×, 3.5×, 3×, 2.5×, 2×, or 1.5× the mRNA encoding EBV gH. In some embodiments, a vaccine comprises mRNA encoding EBV gp220 at equal mass to the mRNA encoding EBV gH.

In some embodiments, a vaccine comprises mRNA encoding EBV gp42 at 5×, 4.5×, 4×, 3.5×, 3×, 2.5×, 2×, or 1.5× the mRNA encoding EBV gp220. In some embodiments, a vaccine comprises mRNA encoding EBV gp42 at equal mass to the mRNA encoding EBV gp220.

In some embodiments, a vaccine comprises mRNA encoding EBV gp42 at 5×, 4.5×, 4×, 3.5×, 3×, 2.5×, 2×, or 1.5× the mRNA encoding EBV gL. In some embodiments, a vaccine comprises mRNA encoding EBV gp42 at equal mass to the mRNA encoding EBV gL.

In some embodiments, a vaccine comprises mRNA encoding EBV gp42 at 5×, 4.5×, 4×, 3.5×, 3×, 2.5×, 2×, or 1.5× the mRNA encoding EBV gH. In some embodiments, a vaccine comprises mRNA encoding EBV gp42 at equal mass to the mRNA encoding EBV gH.

In some embodiments, a vaccine comprises mRNA encoding EBV gL at 5×, 4.5×, 4×, 3.5×, 3×, 2.5×, 2×, or 1.5× the mRNA encoding EBV gp220. In some embodiments, a vaccine comprises mRNA encoding EBV gL at equal mass to the mRNA encoding EBV gp220.

In some embodiments, a vaccine comprises mRNA encoding EBV gL at 5×, 4.5×, 4×, 3.5×, 3×, 2.5×, 2×, or 1.5× the mRNA encoding EBV gp42. In some embodiments, a vaccine comprises mRNA encoding EBV gL at equal mass to the mRNA encoding EBV g42.

In some embodiments, a vaccine comprises mRNA encoding EBV gL at 5×, 4.5×, 4×, 3.5×, 3×, 2.5×, 2×, or 1.5× the mRNA encoding EBV gH. In some embodiments, a vaccine comprises mRNA encoding EBV gL at equal mass to the mRNA encoding EBV gH.

In some embodiments, a vaccine comprises mRNA encoding EBV gH at 5×, 4.5×, 4×, 3.5×, 3×, 2.5×, 2×, or 1.5× the mRNA encoding EBV gp220. In some embodiments, a vaccine comprises mRNA encoding EBV gH at equal mass to the mRNA encoding EBV gp220.

In some embodiments, a vaccine comprises mRNA encoding EBV gH at 5×, 4.5×, 4×, 3.5×, 3×, 2.5×, 2×, or 1.5× the mRNA encoding EBV gp42. In some embodiments, a vaccine comprises mRNA encoding EBV gH at equal mass to the mRNA encoding EBV gp42.

In some embodiments, a vaccine comprises mRNA encoding EBV gH at 5×, 4.5×, 4×, 3.5×, 3×, 2.5×, 2×, or 1.5× the mRNA encoding EBV gL. In some embodiments, a vaccine comprises mRNA encoding EBV gH at equal mass to the mRNA encoding EBV gL.

In some embodiments, the vaccine further comprises (c) a fifth mRNA comprising an open reading frame encoding EBV glycoprotein B (gB).

In some embodiments, the mass ratio of (a):(c) is 4:1, 4:1.5, 2:1, 4:2.5, 4:3, 4:3.5, or 1:1. In some embodiments, the mass ratio of (b):(c) is 2:1, 2:1.5, 1:1, 1:1.5, or 1:2. In some embodiments, the ratio of (c):(c) is 2:1, 2:1.5, 1:1, 1:1.5, or 1:2. In some embodiments, the mass ratio of (d):(c) is 2:1, 2:1.5, 1:1, 1:1.5, or 1:2.

In some embodiments, the mass ratio of (a):(b):(c):(d):(c) is 4:1:1:1.5:1.5. In some embodiments, the ratio of (a):(b):(c):(d):(c) is 4:1:1:1:1.

In some embodiments, a vaccine comprises mRNA encoding EBV gp220 at 5×, 4.5×, 4×, 3.5×, 3×, 2.5×, 2×, or 1.5× the mRNA encoding EBV gB. In some embodiments, a vaccine comprises mRNA encoding EBV gp220 at equal mass to the mRNA encoding EBV gB.

In some embodiments, a vaccine comprises mRNA encoding EBV gp42 at 5×, 4.5×, 4×, 3.5×, 3×, 2.5×, 2×, or 1.5× the mRNA encoding EBV gB. In some embodiments, a vaccine comprises mRNA encoding EBV gp42 at equal mass to the mRNA encoding EBV gB.

In some embodiments, a vaccine comprises mRNA encoding EBV gL at 5×, 4.5×, 4×, 3.5×, 3×, 2.5×, 2×, or 1.5× the mRNA encoding EBV gB. In some embodiments, a vaccine comprises mRNA encoding EBV gL at equal mass to the mRNA encoding EBV gB.

In some embodiments, a vaccine comprises mRNA encoding EBV gH at 5×, 4.5×, 4×, 3.5×, 3×, 2.5×, 2×, or 1.5× the mRNA encoding EBV gB. In some embodiments, a vaccine comprises mRNA encoding EBV gH at equal mass to the mRNA encoding EBV gB.

In some embodiments, a vaccine comprises mRNA encoding EBV gB at 5×, 4.5×, 4×, 3.5×, 3×, 2.5×, 2×, or 1.5× the mRNA encoding EBV gp220. In some embodiments, a vaccine comprises mRNA encoding EBV gB at equal mass to the mRNA encoding EBV gp220.

In some embodiments, a vaccine comprises mRNA encoding EBV gB at 5×, 4.5×, 4×, 3.5×, 3×, 2.5×, 2×, or 1.5× the mRNA encoding EBV gp42. In some embodiments, a vaccine comprises mRNA encoding EBV gB at equal mass to the mRNA encoding EBV gp42.

In some embodiments, a vaccine comprises mRNA encoding EBV gB at 5×, 4.5×, 4×, 3.5×, 3×, 2.5×, 2×, or 1.5× the mRNA encoding EBV gL. In some embodiments, a vaccine comprises mRNA encoding EBV gB at equal mass to the mRNA encoding EBV gL.

In some embodiments, a vaccine comprises mRNA encoding EBV gB at 5×, 4.5×, 4×, 3.5×, 3×, 2.5×, 2×, or 1.5× the mRNA encoding EBV gH. In some embodiments, a vaccine comprises mRNA encoding EBV gB at equal mass to the mRNA encoding EBV gH.

Vaccine Formulations and Dosing Schedules

Provided herein, in some aspects, are vaccines, methods, kits and reagents for prevention or treatment of EBV infection in humans. The vaccines provided herein can be used as prophylactic or therapeutic agents to prevent or treat EBV infection or disease progression. A vaccine may be administered prophylactically or therapeutically as part of an active immunization scheme to healthy individuals or early in infection during the incubation phase or during active infection after onset of symptoms. In some embodiments, the amount of mRNA provided to a cell, a tissue or a subject may be an amount effective for immune prophylaxis.

A vaccine may be utilized in various settings depending on the prevalence of the infection or the degree or level of unmet medical need. mRNA vaccines have superior properties in that they produce much larger antibody titers, better neutralizing immunity, produce more durable immune responses, and/or produce responses earlier than commercially available vaccines.

In some embodiments, the EBV vaccine containing mRNA as described herein can be administered to a subject (e.g., a mammalian subject, such as a human subject), and the mRNA is translated and expressed in vivo to produce an EBV antigen, which then stimulates an immune response in the subject. In some embodiments, an mRNA vaccine is administered to a subject (e.g., a mammalian subject, such as a human subject) in an effective amount to induce an antigen-specific (e.g., EBV-specific) immune response.

Formulation/Dose

A vaccine comprising mRNA and LNP may or may not further comprise one or more other components. For example, a vaccine may include other components including, but not limited to, adjuvants and/or excipients. In some embodiments, a vaccine does not include an adjuvant (they are adjuvant free).

Vaccines may be sterile, pyrogen-free or both sterile and pyrogen-free. General considerations in the formulation and/or manufacture of pharmaceutical agents, such as vaccines, may be found, for example, in Remington: The Science and Practice of Pharmacy 21st ed., Lippincott Williams & Wilkins, 2005 (incorporated herein by reference in its entirety).

Formulations of the vaccines described herein may be prepared by any method known or hereafter developed in the art of pharmacology. In general, such preparatory methods include the step of bringing the active ingredient (e.g., mRNA) into association with an excipient and/or one or more other accessory ingredients (e.g., lipid nanoparticle components described herein), and then, if necessary and/or desirable, dividing, shaping and/or packaging the product into a desired single- or multi-dose unit.

Relative amounts of the active ingredient (i.e., mRNA), the pharmaceutically acceptable excipient (e.g., LNP components), and/or any additional ingredients in a vaccine in accordance with the disclosure will vary, depending upon the identity, size, and/or condition of the subject treated and further depending upon the route by which the vaccine is to be administered. By way of example, the vaccine may comprise between 0.1% and 100%, e.g., between 0.5 and 50%, between 1-30%, between 5-80%, at least 80% (w/w) mRNA.

In some embodiments, an RNA is formulated using one or more excipients to: (1) increase stability; (2) increase cell transfection; (3) permit the sustained or delayed release (e.g., from a depot formulation); (4) alter the biodistribution (e.g., target to specific tissues or cell types); (5) increase the translation of encoded protein in vivo; and/or (6) alter the release profile of encoded protein (antigen) in vivo. In addition to traditional excipients such as any and all solvents, dispersion media, diluents, or other liquid vehicles, dispersion or suspension aids, surface active agents, isotonic agents, thickening or emulsifying agents, preservatives, excipients can include, without limitation, lipidoids, liposomes, lipid nanoparticles, polymers, lipoplexes, core-shell nanoparticles, peptides, proteins, cells transfected with the mRNA (e.g., for transplantation into a subject), hyaluronidase, nanoparticle mimics and combinations thereof.

An effective amount (e.g., effective dose) prevents infection by the virus at a clinically acceptable level. In some embodiments, the effective dose is a dose listed in a package insert for the vaccine. An effective amount (e.g., effective dose) of a vaccine (e.g., comprising mRNA) is based, at least in part, on the target tissue, target cell type, means of administration, physical characteristics of the mRNA (e.g., length, nucleotide composition, and/or extent of modified nucleosides), other components of the vaccine, and other determinants, such as age, body weight, height, sex and general health of the subject. Typically, an effective amount of a vaccine provides an induced or boosted immune response as a function of antigen production in the cells of the subject. In some embodiments, an effective amount of the vaccine containing mRNA having at least one chemical modification is more efficient than a vaccine containing a corresponding unmodified polynucleotide encoding the same antigen or a peptide antigen. Increased antigen production may be demonstrated by increased cell transfection (the percentage of cells transfected with the mRNA vaccine), increased protein translation and/or expression from the polynucleotide, decreased nucleic acid degradation (as demonstrated, for example, by increased duration of protein translation from a modified polynucleotide), or altered antigen specific immune response of the host cell.

The effective amount of the mRNA, as provided herein, depends at least in part on the age of the subject being vaccinated and the vaccine dosing schedule. In some embodiments, the vaccine is administered as a single dose. In other some embodiments, one or more booster dose(s) of the vaccine is administered.

In some embodiments, the vaccine comprises about 25-125 μg mRNA encoding EBV gp220. For example, the vaccine may comprise about 25, 26, 27, 28, 29, 30, 35, 40, 45, 50, 51, 52, 53, 54, 55, 60, 65, 70, 75, 80, 85, 90, 95, 100, 105, 106, 107, 108, 109, 110, 115, 120, or 125 μg mRNA encoding EBV gp220. In some embodiments, the vaccine comprises about 25-30 μg. 50-55 μg, or 105-110 μg mRNA encoding EBV gp220.

In some embodiments, the vaccine comprises about 5-30 μg mRNA encoding EBV gp42. For example, the vaccine may comprise about 5, 6, 7, 8, 9, 10, 11, 12, 13, 14, 15, 16, 17, 18, 19, 20, 21, 22, 23, 24, 25, 26, 27, 28, 29, or 30 μg mRNA encoding EBV gp42. In some embodiments, the vaccine comprises about 5-10 μg. 10-15 μg, or 25-20 μg mRNA encoding EBV gp42.

In some embodiments, the vaccine comprises about 5-30 μg mRNA encoding EBV gL. For example, the vaccine may comprise about 5, 6, 7, 8, 9, 10, 11, 12, 13, 14, 15, 16, 17, 18, 19, 20, 21, 22, 23, 24, 25, 26, 27, 28, 29, or 30 μg mRNA encoding EBV gL. In some embodiments, the vaccine comprises about 5-10 μg. 10-15 μg, or 25-20 μg mRNA encoding EBV gL.

In some embodiments, the vaccine comprises about 10-50 μg mRNA encoding EBV gH. For example, the vaccine may comprise about 10, 15, 20, 25, 30, 35, 40, 45, or 50 μg mRNA encoding EBV gH. In some embodiments, the vaccine comprises about 5-15 μg. 15-25 μg, or 30-50 μg mRNA encoding EBV gH.

In some embodiments, the vaccine comprises 26.7 μg mRNA encoding EBV gp220, 6.7 μg mRNA encoding EBV gp42, 6.7 μg mRNA encoding EBV gL, and 10 μg mRNA encoding EBV gH.

In other embodiments, the vaccine comprises 53.3 μg mRNA encoding EBV gp220, 13.3 μg mRNA encoding EBV gp42, 13.3 μg mRNA encoding EBV gL, and 20 μg mRNA encoding EBV gH.

In still other embodiments, the vaccine comprises 106.7 μg mRNA encoding EBV gp220, 26.7 μg mRNA encoding EBV gp42, 26.7 μg mRNA encoding EBV gL, and 40 μg mRNA encoding EBV gH.

It should be understood that a "total dose" refers to the total amount of mRNA administered, either as a single vaccination or cumulative of an initial dose and any booster dose(s). Thus, if a vaccine is administered as a single dose of 50 μg of mRNA, then the total dose is 50 μg of mRNA. If a vaccine is administered as an initial dose of 50 μg of mRNA then later as a booster dose of 50 μg of mRNA, then the total dose is 100 μg of mRNA.

In some embodiments, a vaccine may be administered intramuscularly, intranasally or intradermally, similarly to the administration of inactivated vaccines known in the art. In preferred embodiments, the vaccine is administered intramuscularly.

The RNA described herein can be formulated into a dosage form described herein, such as an intranasal, intratracheal, or injectable (e.g., intravenous, intraocular, intravitreal, intramuscular, intradermal, intracardiac, intraperitoneal, and subcutaneous).

Dosing Schedule

Prophylactic protection from EBV infection can be achieved following administration of an mRNA vaccine of the present disclosure. Vaccines can be administered once, twice, three times, four times or more but it is likely sufficient to administer the vaccine once (optionally followed by a single booster). It is also possible to administer a vaccine to an infected individual to achieve a therapeutic response. Dosing may need to be adjusted accordingly.

A booster dose refers to an extra administration of the vaccine. A booster (or booster dose or booster vaccine) may be given after an earlier administration of the vaccine. Any two doses of an mRNA vaccine (e.g., an initial dose and a booster dose, or a booster dose and a second booster dose) may be administered, for example, at least one month (~28, 29, 30, or 31 days) apart, or at least 2, 3, 4, 5, 6, 7, 8, 9, 10, 11, or 12 months apart. In some embodiments, a booster dose is administered yearly.

In some embodiments, a booster dose (e.g., a first, second or third booster dose) is administered at least one month, at least two months, at least three months, at least four months, at least five months, or at least six months after the initial dose or after another booster dose. In some embodiments, a booster dose is administered one month, two months, three months, four months, five months, or six months after the initial dose or after another booster dose. In some embodiments, a second booster dose is administered at least one month, at least two months, at least three months, at least four months, at least five months, or at least six months after a first booster dose. In some embodiments, a second booster dose is administered one month, two months, three months, four months, five months, or six months after a first booster dose. In some embodiments, a booster dose is administered one year or at least one year after the initial dose. In some embodiments, a second booster dose is administered one year or at least one year after a first booster dose.

A method of eliciting an immune response in a subject against an EBV antigen (or multiple antigens) is provided in aspects of the present disclosure. In some embodiments, the method involves administering to the subject a vaccine comprising a mRNA having an open reading frame encoding an EBV antigen, thereby inducing in the subject an immune response specific to the EBV antigen, wherein anti-antigen antibody titer in the subject is increased following vaccination relative to anti-antigen antibody titer in a subject vaccinated with a prophylactically effective dose of a traditional vaccine against the antigen (e.g., EBV antigen).

An anti-antigen antibody is a serum antibody the binds specifically to the antigen (e.g., EBV antigen). In some embodiments, the anti-antigen antibody titer in the subject is increased 1 log to 10 log following vaccination relative to anti-antigen antibody titer in a subject vaccinated with a prophylactically effective dose of a traditional vaccine against the EBV or an unvaccinated subject. In some embodiments, the anti-antigen antibody titer in the subject is increased 1 log, 2 log, 3 log, 4 log. 5 log, or 10 log following vaccination relative to anti-antigen antibody titer in a subject vaccinated with a prophylactically effective dose of a traditional vaccine against the EBV or an unvaccinated subject.

A traditional vaccine, as used herein, refers to a vaccine other than the mRNA vaccines of the present disclosure. For instance, a traditional vaccine includes, but is not limited, to live microorganism vaccines, killed microorganism vaccines, subunit vaccines, protein antigen vaccines, DNA vaccines, virus like particle (VLP) vaccines, etc. In exemplary embodiments, a traditional vaccine is a vaccine that has achieved regulatory approval and/or is registered by a national drug regulatory body, for example the Food and Drug Administration (FDA) in the United States or the European Medicines Agency (EMA).

In some embodiments, the immune response in the subject is equivalent to an immune response in a subject vaccinated with a traditional vaccine against the EBV at 2 times to 100 times the dosage level relative to the vaccine. In some embodiments, the immune response in the subject is equivalent to an immune response in a subject vaccinated with a traditional vaccine at twice the dosage level relative to a vaccine of the present disclosure. In some embodiments, the immune response in the subject is equivalent to an immune response in a subject vaccinated with a traditional vaccine at three times the dosage level relative to a vaccine of the present disclosure. In some embodiments, the immune response in the subject is equivalent to an immune response in a subject vaccinated with a traditional vaccine at 4 times, 5 times, 10 times, 50 times, or 100 times the dosage level relative to a vaccine of the present disclosure. In some embodiments, the immune response in the subject is equivalent to an immune response in a subject vaccinated with a traditional vaccine at 10 times to 1000 times the dosage level relative to a vaccine of the present disclosure. In some embodiments, the immune response in the subject is equivalent to an immune response in a subject vaccinated with a traditional vaccine at 100 times to 1000 times the dosage level relative to a vaccine of the present disclosure.

In some embodiments, the immune response in the subject is induced 2 days to 10 weeks earlier relative to an immune response induced in a subject vaccinated with a prophylactically effective dose of a traditional vaccine against EBV. In some embodiments, the immune response in the subject is induced 2 days, 3 days, 1 week, 2 weeks, 3 weeks, 5 weeks, or 10 weeks earlier relative to an immune response induced in a subject vaccinated with a prophylactically effective dose of a traditional vaccine.

In some embodiments, the immune response is assessed by determining [protein] antibody titer in the subject. In other embodiments, the ability of serum or antibody from an immunized subject is tested for its ability to neutralize viral uptake or reduce EBV transformation of human B lymphocytes. In other embodiments, the ability to promote a robust T cell response(s) is measured using art recognized techniques.

Vaccine Efficacy

Some aspects of the present disclosure provide formulations of the mRNA vaccines, wherein the mRNA is formulated in an effective amount to produce an antigen specific immune response in a subject (e.g., production of antibodies specific to an EBV antigen). "An effective amount" is a dose of the mRNA effective to produce an antigen-specific immune response. Also provided herein are methods of inducing an antigen-specific immune response in a subject.

As used herein, an immune response to a vaccine or LNP of the present disclosure is the development in a subject of a humoral and/or a cellular immune response to a (one or more) EBV protein(s) present in the vaccine. For purposes of the present disclosure, a "humoral" immune response refers to an immune response mediated by antibody molecules, including, e.g., secretory (IgA) or IgG molecules, while a "cellular" immune response is one mediated by T-lymphocytes (e.g., CD4+ helper and/or CD8+ T cells (e.g., CTLs) and/or other white blood cells. One important aspect of cellular immunity involves an antigen-specific response by cytolytic T-cells (CTLs). CTLs have specificity for peptide antigens that are presented in association with proteins encoded by the major histocompatibility complex (MHC) and expressed on the surfaces of cells. CTLs help induce and promote the destruction of intracellular microbes or the lysis of cells infected with such microbes. Another aspect of cellular immunity involves and antigen-specific response by helper T-cells. Helper T-cells act to help stimulate the function and focus the activity nonspecific effector cells against cells displaying peptide antigens in association with MHC molecules on their surface. A cellular immune response also leads to the production of cytokines, chemokines, and other such molecules produced by activated T-cells and/or other white blood cells including those derived from CD4+ and CD8+ T-cells.

In some embodiments, the antigen-specific immune response is characterized by measuring an anti-EBV antigen antibody titer produced in a subject administered a vaccine as provided herein. An antibody titer is a measurement of the amount of antibodies within a subject, for example, antibodies that are specific to a particular antigen (e.g., an anti-EBV F glycoprotein) or epitope of an antigen. Antibody titer is typically expressed as the inverse of the greatest dilution that provides a positive result. Enzyme-linked immunosorbent assay (ELISA) is a common assay for determining antibody titers, for example.

In some embodiments, an antibody titer is used to assess whether a subject has had an infection or to determine whether immunizations are required. In some embodiments, an antibody titer is used to determine the strength of an autoimmune response, to determine whether a booster immunization is needed, to determine whether a previous vaccine was effective, and to identify any recent or prior infections. In accordance with the present disclosure, an antibody titer may be used to determine the strength of an immune response induced in a subject by an mRNA vaccine.

In some embodiments, an anti-EBV antigen antibody titer produced in a subject is increased by at least 1 log relative to a control. For example, anti-EBV antigen antibody titer produced in a subject may be increased by at least 1.5, at least 2, at least 2.5, or at least 3 log relative to a control. In some embodiments, the anti-EBV antigen antibody titer produced in the subject is increased by 1, 1.5, 2, 2.5 or 3 log relative to a control. In some embodiments, the anti-EBV antigen antibody titer produced in the subject is increased by 1-3 log relative to a control. For example, the anti-EBV antigen antibody titer produced in a subject may be increased by 1-1.5, 1-2, 1-2.5, 1-3, 1.5-2, 1.5-2.5, 1.5-3, 2-2.5, 2-3, or 2.5-3 log relative to a control.

In some embodiments, the anti-EBV antigen antibody titer produced in a subject is increased at least 2 times relative to a control. For example, the anti-EBV antigen n antibody titer produced in a subject may be increased at least 3 times, at least 4 times, at least 5 times, at least 6 times, at least 7 times, at least 8 times, at least 9 times, or at least 10 times relative to a control. In some embodiments, the anti-EBV antigen antibody titer produced in the subject is increased 2, 3, 4, 5, 6, 7, 8, 9, or 10 times relative to a control. In some embodiments, the anti-EBV antigen antibody titer produced in a subject is increased 2-10 times relative to a control. For example, the anti-EBV antigen antibody titer produced in a subject may be increased 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, or 9-10 times relative to a control.

In some embodiments, an antigen-specific immune response is measured as a ratio of geometric mean titer (GMT), referred to as a geometric mean ratio (GMR), of serum neutralizing antibody titers to EBV. A geometric mean titer (GMT) is the average antibody titer for a group of subjects calculated by multiplying all values and taking the nth root of the number, where n is the number of subjects with available data.

A control, in some embodiments, is an anti-EBV antigen antibody titer produced in a subject who has not been administered an mRNA vaccine. In some embodiments, a control is an anti-EBV antigen antibody titer produced in a subject administered a recombinant or purified protein vaccine. Recombinant protein vaccines typically include protein antigens that either have been produced in a heterologous expression system (e.g., bacteria or yeast) or purified from large amounts of the pathogenic organism.

In some embodiments, the ability of an mRNA vaccine to be effective is measured in a murine model. For example, a vaccine may be administered to a murine model and the murine model assayed for induction of neutralizing antibody titers. Viral challenge studies may also be used to assess the efficacy of a vaccine of the present disclosure. For example, a vaccine may be administered to a murine model, the murine model challenged with virus, and the murine model assayed for survival and/or immune response (e.g., neutralizing antibody response, T cell response (e.g., cytokine response)).

In some embodiments, an effective amount of an mRNA vaccine is a dose that is reduced compared to the standard of care dose of a recombinant protein vaccine. A "standard of care," as provided herein, refers to a medical or psychological treatment guideline and can be general or specific. "Standard of care" specifies appropriate treatment based on scientific evidence and collaboration between medical professionals involved in the treatment of a given condition. It is the diagnostic and treatment process that a physician/clinician should follow for a certain type of patient, illness or clinical circumstance. A "standard of care dose," as provided herein, refers to the dose of a recombinant or purified protein vaccine, or a live attenuated or inactivated vaccine, or a VLP vaccine, that a physician/clinician or other medical professional would administer to a subject to treat or prevent EBV infection or a related condition, while following the standard of care guideline for treating or preventing EBV infection or a related condition.

In some embodiments, the anti-EBV antigen antibody titer produced in a subject administered an effective amount of a vaccine is equivalent to an anti-EBV antigen antibody titer produced in a control subject administered a standard of care dose of a recombinant or purified protein vaccine, or a live attenuated or inactivated vaccine, or a VLP vaccine.

Vaccine efficacy may be assessed using standard analyses (sec, e.g., Weinberg et al., J Infect Dis. 2010 Jun. 1; 201(11):1607-10). For example, vaccine efficacy may be measured by double-blind, randomized, clinical controlled trials. Vaccine efficacy may be expressed as a proportionate reduction in disease attack rate (AR) between the unvaccinated (ARU) and vaccinated (ARV) study cohorts and can be calculated from the relative risk (RR) of disease among the vaccinated group with use of the following formulas:

$$\text{Efficacy}=(\text{ARU}-\text{ARV})/\text{ARU}\times 100\text{; and}$$

$$\text{Efficacy}=(1-\text{RR})\times 100.$$

Likewise, vaccine effectiveness may be assessed using standard analyses (see, e.g., Weinberg et al., J Infect Dis. 2010 Jun. 1; 201(11):1607-10). Vaccine effectiveness is an assessment of how a vaccine (which may have already proven to have high vaccine efficacy) reduces disease in a population. This measure can assess the net balance of benefits and adverse effects of a vaccination program, not just the vaccine itself, under natural field conditions rather than in a controlled clinical trial. Vaccine effectiveness is proportional to vaccine efficacy (potency) but is also affected by how well target groups in the population are immunized, as well as by other non-vaccine-related factors that influence the 'real-world' outcomes of hospitalizations, ambulatory visits, or costs. For example, a retrospective case control analysis may be used, in which the rates of vaccination among a set of infected cases and appropriate controls are compared. Vaccine effectiveness may be expressed as a rate difference, with use of the odds ratio (OR) for developing infection despite vaccination:

$$\text{Effectiveness}=(1-\text{OR})\times 100.$$

In some embodiments, efficacy of the vaccine is at least 60% relative to unvaccinated control subjects. For example, efficacy of the vaccine may be at least 65%, at least 70%, at least 75%, at least 80%, at least 85%, at least 95%, at least 98%, or 100% relative to unvaccinated control subjects.

Sterilizing Immunity. Sterilizing immunity refers to a unique immune status that prevents effective pathogen infection into the host. In some embodiments, the effective amount of a vaccine of the present disclosure is sufficient to provide sterilizing immunity in the subject for at least 1 year. For example, the effective amount of a vaccine of the present disclosure is sufficient to provide sterilizing immunity in the subject for at least 2 years, at least 3 years, at least 4 years, or at least 5 years. In some embodiments, the effective amount of a vaccine of the present disclosure is sufficient to provide sterilizing immunity in the subject at an at least 5-fold lower dose relative to control. For example, the effective amount may be sufficient to provide sterilizing immunity in the subject at an at least 10-fold lower, 15-fold, or 20-fold lower dose relative to a control.

Detectable Antigen. In some embodiments, the effective amount of a vaccine of the present disclosure is sufficient to produce detectable levels of EBV antigen as measured in serum of the subject at 1-72 hours post administration.

Titer. An antibody titer is a measurement of the amount of antibodies within a subject, for example, antibodies that are specific to a particular antigen (e.g., an anti-EBV antigen). Antibody titer is typically expressed as the inverse of the greatest dilution that provides a positive result. Enzyme-linked immunosorbent assay (ELISA) is a common assay for determining antibody titers, for example.

In some embodiments, the effective amount of a vaccine of the present disclosure is sufficient to produce a 1,000-10,000 neutralizing antibody titer produced by neutralizing antibody against the EBV antigen as measured in serum of the subject at 1-72 hours post administration. In some embodiments, the effective amount is sufficient to produce a 1,000-5,000 neutralizing antibody titer produced by neutralizing antibody against the EBV antigen as measured in serum of the subject at 1-72 hours post administration. In some embodiments, the effective amount is sufficient to produce a 5,000-10,000 neutralizing antibody titer produced by neutralizing antibody against the EBV antigen as measured in serum of the subject at 1-72 hours post administration.

In some embodiments, the neutralizing antibody titer is at least 100 $NT_{50}$. For example, the neutralizing antibody titer may be at least 200, 300, 400, 500, 600, 700, 800, 900 or 1000 $NT_{50}$. In some embodiments, the neutralizing antibody titer is at least 10,000 $NT_{50}$.

In some embodiments, the neutralizing antibody titer is at least 100 neutralizing units per milliliter (NU/mL). For example, the neutralizing antibody titer may be at least 200, 300, 400, 500, 600, 700, 800, 900 or 1000 NU/mL. In some embodiments, the neutralizing antibody titer is at least 10,000 NU/mL.

In some embodiments, an anti-EBV antigen antibody titer produced in the subject is increased by at least 1 log relative to a control. For example, an anti-EBV antigen antibody titer produced in the subject may be increased by at least 2, 3, 4, 5, 6, 7, 8, 9 or 10 log relative to a control.

In some embodiments, an anti-EBV antigen antibody titer produced in the subject is increased at least 2 times relative to a control. For example, an anti-EBV antigen antibody titer produced in the subject is increased by at least 3, 4, 5, 6, 7, 8, 9 or 10 times relative to a control.

In some embodiments, a geometric mean, which is the nth root of the product of n numbers, is generally used to describe proportional growth. Geometric mean, in some embodiments, is used to characterize antibody titer produced in a subject.

A control may be, for example, an unvaccinated subject, or a subject administered a live attenuated viral vaccine, an inactivated viral vaccine, or a protein subunit vaccine.

EXAMPLES

Example 1

In vivo studies in Balb/c mice were conducted to evaluate vaccines comprising mRNA encoding soluble EBV gp42 in combination with other EBV antigens. The experimental design is shown in Tables 1 and Table 2. The sequences of the mRNAs used are provided in Table 3, 5

TABLE 1

Studies with mRNA encoding WT EBV gp42

| Group # | Combination | mRNA | μg |
|---|---|---|---|
| 1 | WT gp42 | gH | 0.5 |
| | ⅓ Dose | gL | 0.33 |
| | | gp220 | 1.33 |
| | | wt gp42 | 0.33 |
| 2 | WT gp42 | gH | 1.5 |
| | Dose | gL | 1 |
| | | Gp220 | 4 |
| | | wt gp42 | 1 |
| 3 | WT gp42 | gH | 0.5 |
| | ⅓ Dose + gB | gL | 0.33 |
| | | gp220 | 1.33 |
| | | wt gp42 | 0.33 |
| | | gB | 0.5 |
| 4 | WT gp42 | gH | 1.5 |
| | Dose + gB | gL | 1 |
| | | gp220 | 4 |
| | | wt gp42 | 1 |
| | | gB | 1.5 |

TABLE 2

Studies with mRNA encoding soluble EBV gp42

| Group # | Combination | mRNA | Dose (μg) Ratios |
|---|---|---|---|
| 1 | Sol gp42 | gH | 0.5 |
| | ⅓ Dose | gL | 0.33 |
| | | gp220 | 1.33 |
| | | wt gp42 | 0.33 |
| 2 | Sol gp42 | gH | 1.5 |
| | Dose | gL | 1 |
| | | gp220 | 4 |
| | | wt gp42 | 1 |
| 3 | Sol gp42 | gH | 0.5 |
| | ⅓ Dose + gB | gL | 0.33 |
| | | gp220 | 1.33 |
| | | wt gp42 | 0.33 |
| | | gB | 0.5 |
| 4 | Sol gp42 | gH | 1.5 |
| | Dose + gB | gL | 1 |
| | | gp220 | 4 |
| | | wt gp42 | 1 |
| | | gB | 1.5 |

Two doses of each antigen combination were tested: 'Dose' and '⅓ Dose'. For each EBV gp42 design, the mRNA encoding EBV gp42 (ORF SEQ ID NO: 10 or 14) was included at equal mass to the mRNA encoding EBV gL (ORF SEQ ID NO: 8). Each gp42 design was tested in the presence and absence of mRNA encoding EBV gB (ORF SEQ ID NO: 12) for each dose. mRNA encoding EBV gH (ORF SEQ ID NO: 6) and mRNA encoding EBV gB (where applicable) were included at 1.5× the mass of mRNA encoding gL and mRNA encoding gp42 to account for stability. The mRNA encoding gp220 (ORF SEQ ID NO: 4) was included at 4× the mass of gL and gp42.

Figure 2A:
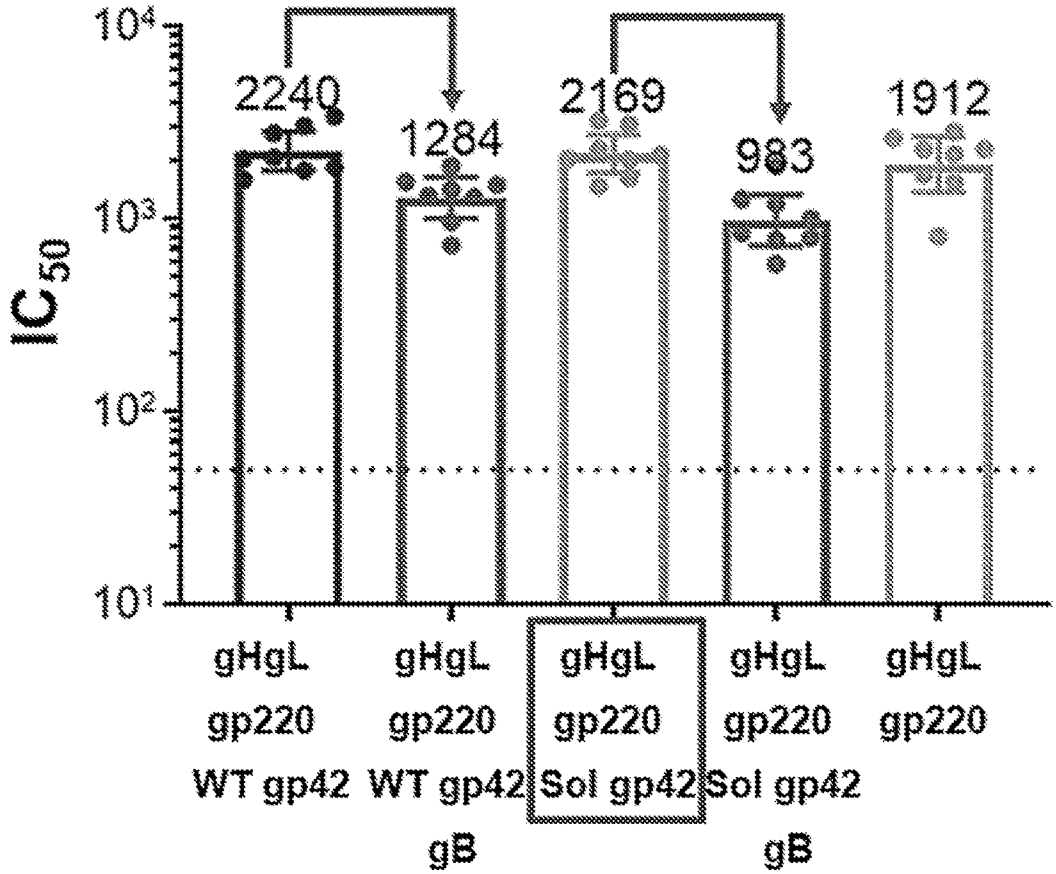
FIGS. 2A-2B are graphs of data showing that the addition of mRNA encoding soluble EBV gp42 to a vaccine comprising mRNA encoding EBV gH, mRNA encoding EBV gL, and mRNA encoding gp220 (1) improves neutralizing antibody titers produced against B cell infection, similar to mRNA encoding wild-type (membrane-bound) gp42 (FIG. 2A) and (2) does not dampen neutralizing antibody titers produced against epithelial cell to the extent of mRNA encoding wild-type gp42 (FIG. 2B). The data also shows that the addition of mRNA encoding EBV gB to a vaccine comprising either mRNA encoding soluble gp42 or mRNA encoding wild-type gp42 leads to a significant drop in B cell neutralizing antibody titers (FIG. 2A).
Figure 2B:
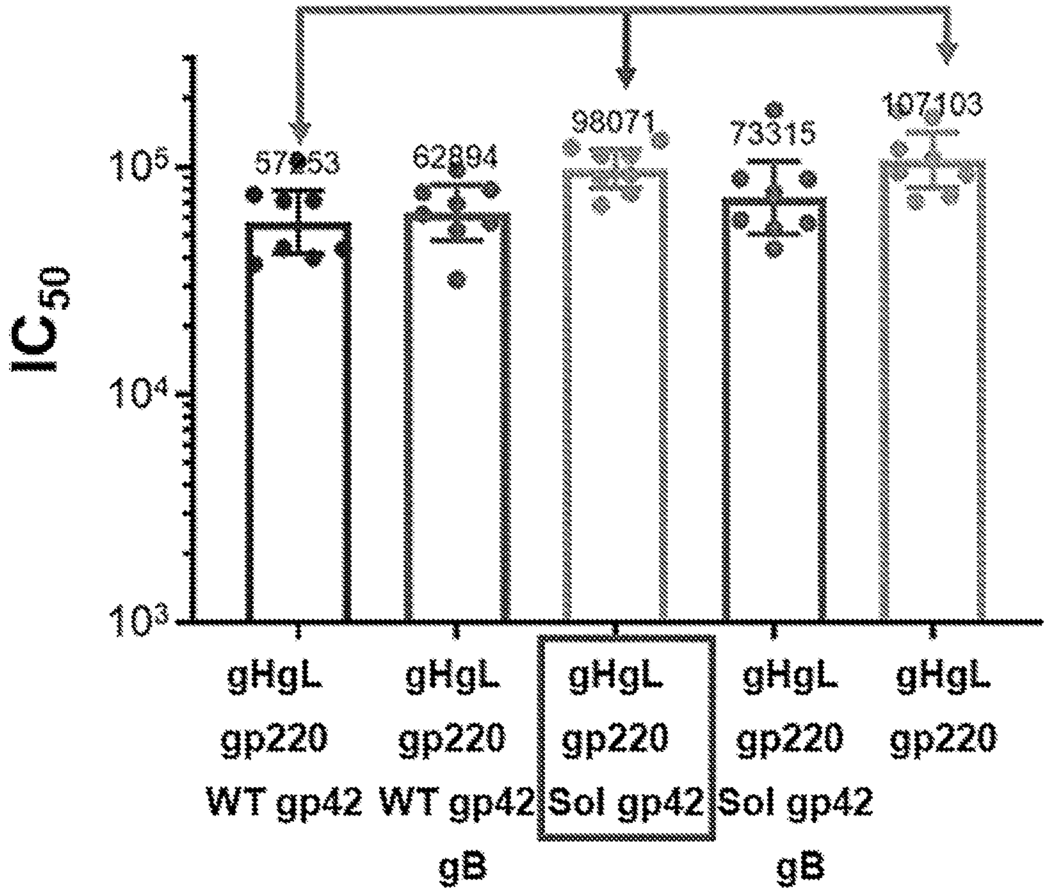

Balb/c mice were vaccinated intramuscularly with the EBV vaccines comprising mRNA encoding the various EBV antigens as set out above in Tables 1 and 2, formulated in a lipid nanoparticle. Neutralization against B cell infection (FIG. 2A) and neutralization against epithelial cell infection (FIG. 2B) was assessed for the 'Dose' groups.

These in vivo results show mRNA encoding soluble EBV gp42 adds positively to neutralizing antibody titers produced against B cell infection while not dampening neutralizing antibody titers produced against epithelial cell infection (unlike WT gp42). The addition of mRNA encoding EBV gB was found to cause a drop in neutralizing antibody titers produced against B cell infection when added to vaccines comprising individual mRNAs encoding EBV gH, EBV gL, EBV gp220, and soluble EBV gp42 (similar to WT gp42).

Example 2

Naïve Balb/c mice were given two doses of a vaccine comprising mRNAs encoding the EBV gp220, sol EBV gp42, EBV gL, and EBV gH proteins of Example 1 approximately three weeks apart. Neutralizing antibody titers against B cell or epithelial cell infection were measured two weeks after the second dose using GFP-labeled virus. Neutralizing antibodies in a set of eight convalescent human sera were measured for comparison.

Figure 3A:
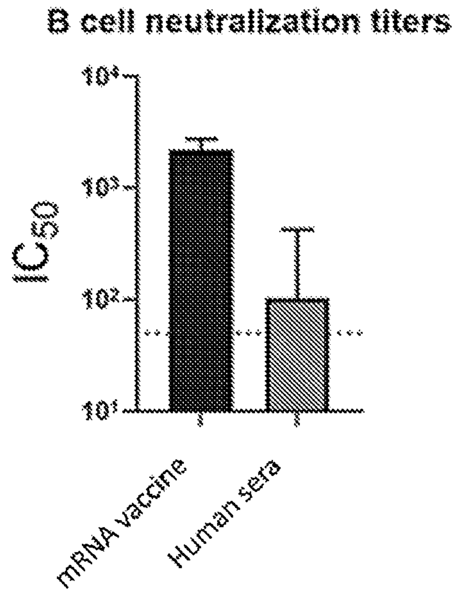
FIGS. 3A-3B include graphs showing neutralizing antibodies against B cell infection (FIG. 3A) and against epithelial cell infection (FIG. 3B) observed in preclinical studies.
Figure 3B:
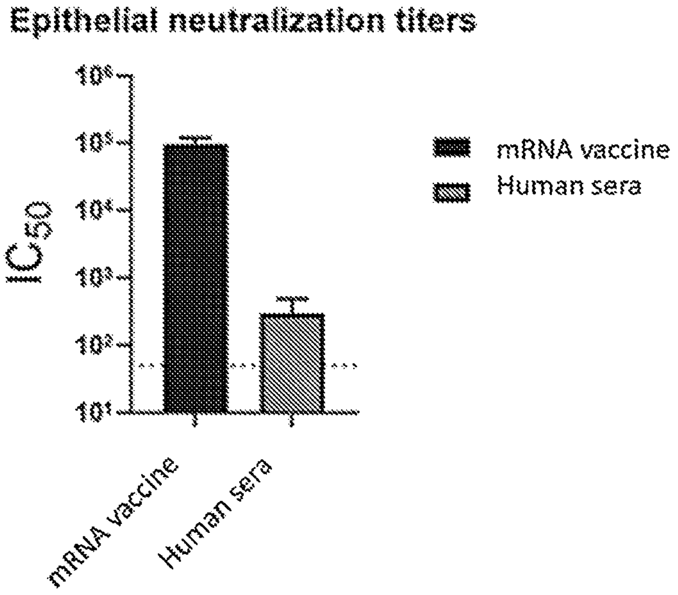

Results shown in FIG. 3 represent eight animals per group and demonstrate high levels of neutralizing antibodies against B cell and epithelial cell infection, and at levels significantly higher than those observed in naturally infected human sera.

Example 3

Figure 4B:
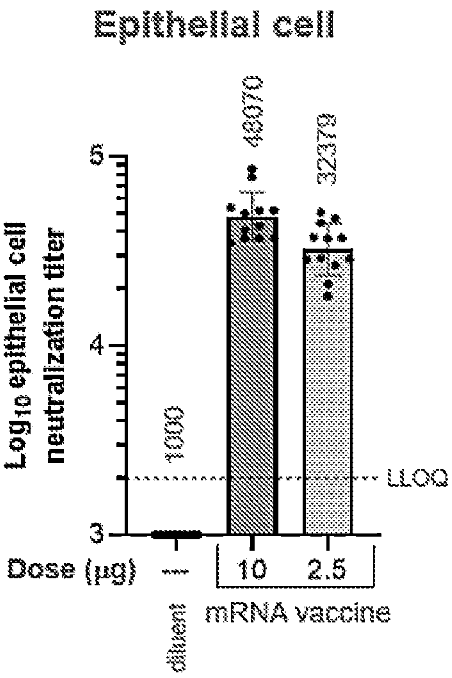
Figure 5A:
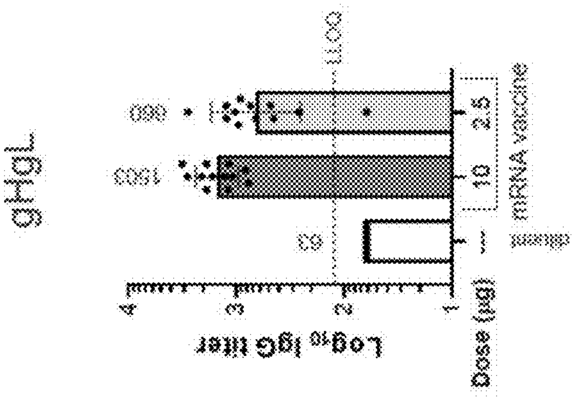
FIGS. 5A-5C include graphs showing IgG titers in an ELISA assay using samples from Balb/c mice administered two different doses of mRNA vaccine: 10 μg (5.33 μg mRNA encoding EBV gp220, 2 μg mRNA encoding EBV gH, 1.33 μg mRNA encoding EBV gL, 1.33 μg mRNA encoding EBV sgp42) and 2.5 μg (1.33 μg mRNA encoding EBV gp220, 0.5 μg mRNA encoding EBV gH, 0.33 μg mRNA encoding EBV gL, 0.33 μg mRNA encoding EBV gp42).
Figure 5B:
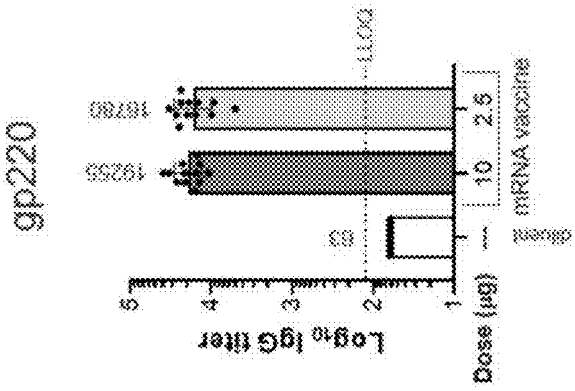
Figure 5C:
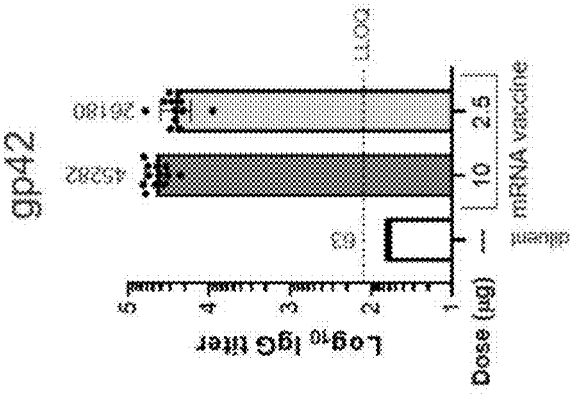

Balb/c mice were immunized twice (3 weeks apart) intramuscularly with diluent or mRNA vaccine encoding gp220, gH, gL and sgp42 (10 μg or 2.5 μg). Sera were collected 2 weeks post the second dose and analyzed for neutralizing and binding antibody levels. Neutralizing antibodies (nAb) were detected in the serum of mice immunized with either dose of mRNA vaccine, but not in mice injected with diluent. Antibodies raised by mRNA vaccine immunization were able to inhibit B cell (FIG. 4A) and epithelial cell infection (FIG. 4B). B cell and epithelial cell nAb titers exhibited a slight (<2-fold) dose-dependent effect. The levels of antigen-specific antibodies in serum were measured using ELISA. Three individual ELISAs were used to measure anti-gHgL (FIG. 5A), anti-gp220 (FIG. 5B) and anti-gp42 (FIG. 5C) IgG. Binding antibodies to each antigen were detected in serum from mice immunized with mRNA vaccine, but not diluent. As was seen with the nAb titers, the overall dose-dependent effect was modest: less than 2-fold for gp220 and gp42, and ~2.3-fold for gHgL.

Example 4

Figure 6A:
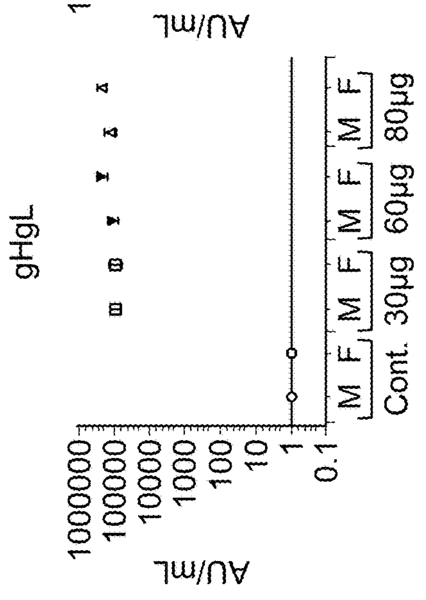
FIGS. 6A-6C include graphs showing antigen-binding antibody titers from a 2-dose 35-day immunogenicity study in rats. The animals were administered the first dose on Day 1 and the second dose on Day 22, then antibody titers were assessed on Day 35. Three different doses were assessed: 30 μg total mRNA, 60 μg total mRNA, and 80 μg total mRNA (mRNA encoding EBV gp220, mRNA encoding EBVgH, mRNA encoding EBV gL, mRNA encoding EBV sgp42). N=10 (5 males and 5 females).
Figure 6B:
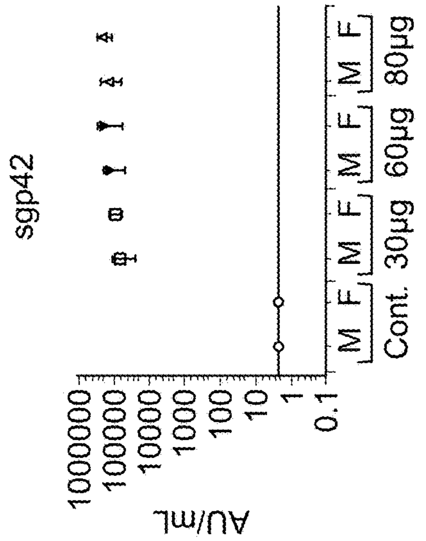
Figure 6C:
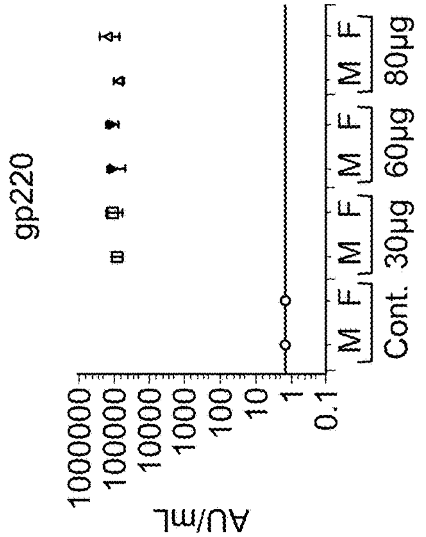

Sprague Dawley rats were immunized twice with intramuscular injections of mRNA vaccine at 30 μg. 60 μg or 80 μg, or PBS (control) at a 3 weeks' interval. Antibody titers were measured in serum 2 weeks after the second immunization using a multiplex assay. All animals receiving mRNA vaccine showed detectable antibody titers to gHgL (FIG. 6A), sgp42 (FIG. 6B) and gp220 (FIG. 6C).

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one." It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including." "carrying." "having." "containing," "involving." "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean±10% of the recited numerical value.

Where a range of values is provided, each value between the upper and lower ends of the range are specifically contemplated and described herein.

The entire contents of International Application Nos. PCT/US2015/027400, PCT/US2016/043348, PCT/US2016/058327, PCT/US2016/058324, PCT/US2016/058314, PCT/US2016/058310, and PCT/US2016/058321, are incorporated herein by reference.

SEQUENCES

It should be understood that any of the mRNA sequences described herein may include a 5' UTR and/or a 3' UTR. The UTR sequences may be selected from the following sequences, or other known UTR sequences may be used. It should also be understood that any of the mRNA constructs described herein may further comprise a polyA tail and/or cap (e.g., 7mG(5')ppp(5')NlmpNp). Further, while many of the mRNAs and encoded antigen sequences described herein include a signal peptide and/or a peptide tag (e.g., C-terminal His tag), it should be understood that the indicated signal peptide and/or peptide tag may be substituted for a different signal peptide and/or peptide tag, or the signal peptide and/or peptide tag may be omitted.

5' UTR:

(SEQ ID NO: 24)

GGGAAAUAAGAGAGAAAAGAAGAGUAAGAAGAAAUAUAAGAGCCACC

5' UTR:

(SEQ ID NO: 1)

GGGAAAUAAGAGAGAAAAGAAGAGUAAGAAGAAAUAUAAGACCCCGGCGC

CGCCACC

3' UTR:

(SEQ ID NO: 25)

UGAUAAUAGGCUGGAGCCUCGGUGGCCAUGCUUCUUGCCCCUUGGGCCUC

CCCCCAGCCCCUCCUCCCCUUCCUGCACCCGUACCCCCGUGGUCUUUGAA

UAAAGUCUGAGUGGGCGGC

3' UTR:

(SEQ ID NO: 3)

UGAUAAUAGGCUGGAGCCUCGGUGGCCUAGCUUCUUGCCCCUUGGGCCUC

CCCCCAGCCCCUCCUCCCCUUCCUGCACCCGUACCCCCGUGGUCUUUGAA

UAAAGUCUGAGUGGGCGGC

TABLE 3

Exemplary EBV Sequences
Sequences used in Examples 1 and 2 above

| gp220 | | SEQ ID NO: |
|---|---|---|
| SEQ ID NO: 17 consists of from 5' end to 3' end, 5' UTR SEQ ID NO: 1, mRNA ORF SEQ ID NO: 2, and 3' UTR SEQ ID NO: 3. | | 17 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUA<br>AGACCCCGGCGCCGCCACC | 1 |
| ORF of mRNA Construct (excluding the stop codon) | AUGGAGGCAGCACUGCUGGUCUGCCAGUAUACAAUCCAG<br>UCGCUCAUUCAUCUGACAGGCGAGGACCCCGGCUUCUUU<br>AACGUGGAAAUCCCAGAGUUCCCUUUCUAUCCAACCUGU<br>AACGUUUGCACUGCUGACGUGAACGUGACAAUCAAUUUC<br>GACGUGGGAGGAAAGAAGCAUCAGCUUGAUCUGGAUUUC<br>GGCCAACUGACGCCACACACCAAAGCGGUGUACCAACCAA<br>GGGGUGCAUUUGGAGGGAGCGAGAAUGCUACAAACCUGU<br>UCUUACUGGAACUGCUUGGUGCAGGAGAGCUGGCACUAA<br>CCAUGCGAAGCAAGAAGCUCCCCAUCAACGUUACCACCGG<br>GGAAGAACAGCAAGUCAGCCUUGAAUCCGUGGAUGUGUA<br>CUUUCAGGAUGUUUUCGGCACCAUGUGGUGUCACCACGC<br>UGAGAUGCAGAAUCCCGUGUAUCUCAUACCCGAGACUGU<br>ACCCUACAUCAAGUGGGAUAAUUGCAAUUCAACUAAUAU<br>UACGGCUGUGGUGAGGGCCCAGGGCUUGGACGUGACUCU<br>GCCCUUAUCUCUACCUACUUCUGCCCAAGACUCCAAUUUC<br>UCUGUCAAGACCGAGAUGCUCGGGAAUGAGAUCGAUAUC<br>GAGUGCAUCAUGGAGGACGGUGAGAUAAGCCAGGUUCUG<br>CCCGGCGACAACAAGUUCAAUAUCACUUGUUCUGGCUAC<br>GAGUCCCAUGUGCCUAGUGGUGGCAUACUCACAAGUACU<br>UCUCCCGUAGCCACGCCCAUUCCCGGAACCGGAUACGCCU<br>ACAGUCUGCGUCUGACCCCACGGCCUGUGUCCAGAUUCCU<br>GGGUAACAAUAGUAUCUUAUACGUGUUUUAUAGCGGAAA<br>CGGCCCUAAAGCGUCCGGAGGGGACUAUUGUAUUCAGAG<br>UAAUAUCGUUUUCUCUGAUGAGAUUCCUGCCAGUCAGGA<br>CAUGCCGACAAACACAACUGAUAUUACCUACGUGGGCGA<br>CAAUGCCACGUAUUCAGUGCCCAUGGUCACGAGCGAGGA<br>CGCCAAUUCACCAAAUGUUACUGUAACAGCUUUCUGGGC<br>CUGGCCAAAUAACACUGAGACUGACUUCAAAUGUAAGUG<br>GACUUUGACCUCUGGAACUCCGUCGGGUUGCGAGAAUAU<br>CAGCGGGGCCUUUGCUUCCAACAGGACUUUCGACAUCAC<br>UGUCUCAGGGCUGGGGACAGCACCGAAGACAUUAAUCAU<br>AACACGGACCGCCACCAACGCCACGACUACAACCCAUAAG<br>GUGAUCUUUUCCAAGGCACCUGAGUCCACCACUACCUCCC<br>CGACUCUUAACACUACGGGCUUCGCUGAUCCCAACACCAC<br>UACGGGGUUGCCUAGCUCGACACAUGUGCCGACGAACCU<br>GACUGCCCCUGCAUCGACCGGGCCCACAGUUUCGACCGCC<br>GAUGUGACAUCACCAACGCCCGCAGGUACAACCUCAGGC<br>GCCAGCCCAGUGACCCCUUCCCCAAGCCCCUGGGAUAAUG<br>GAACGGAGUCCACGCCUCCCCAGAACGCAACCAGUCCUCA<br>GGCGCCCAGCGGGCAGAAGACUGCGGUGCCAACUGUGAC<br>CAGCACCGGUGGCAAGGCCAACUCAACAACUGGAGGCAA<br>GCAUACGACGGGGCACGGCGCCCGGACCUCCACUGAACCC<br>ACGACCGAUUACGGAGGUGACAGCACAACACCGCGGCCA<br>CGAUAUAAUGCCACCACUUAUCUGCCACCAUCCACAAGCU<br>CCAAGCUGCGGCCACGGUGGACCUUCACAAGCCCACCCGU<br>GACGACUGCCCAAGCGACGGUGCCAGUGCCACCUACAAGC<br>CAGCCACGCUUCUCCAACCUUAGUAUGCUCGUUCUCCAGU<br>GGGCCAGCCUUGCUGUUCUGACCCUCCUCCUGCUGCUCGU<br>GAUGGCCGAUUGCGCCUUUAGGAGAAACCUCAGCACUAG<br>CCACACGUACACCACGCCGCCCUACGAUGACGCCGAGACU<br>UACGUC | 2 |
| 3' UTR | UGAUAAUAGGCUGGAGCCUCGGUGGCCUAGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGG<br>C | 3 |
| Corresponding amino acid sequence | MEAALLVCQYTIQSLIHLTGEDPGFFNVEIPEFPFYPTCNVCTA<br>DVNVTINFDVGGKKHQLDLDFGQLTPHTKAVYQPRGAFGGS<br>ENATNLFLLELLGAGELALTMRSKKLPINVTTGEEQQVSLESV<br>DVYFQDVFGTMWCHHAEMQNPVYLIPETVPYIKWDNCNSTN<br>ITAVVRAQGLDVTLPLSLPTSAQDSNFSVKTEMLGNEIDIECIM<br>EDGEISQVLPGDNKFNITCSGYESHVPSGGILTSTSPVATPIPGT<br>GYAYSLRLTPRPVSRFLGNNSILYVFYSGNGPKASGGDYCIQS<br>NIVFSDEIPASQDMPTNTTDITYVGDNATYSVPMVTSEDANSP<br>NVTVTAFWAWPNNTETDFKCKWTLTSGTPSGCENISGAFASN<br>RTFDITVSGLGTAPKTLIITRTATNATTTTHKVIFSKAPESTTTS<br>PTLNTTGFADPNTTTGLPSSTHVPTNLTAPASTGPTVSTADVTS<br>PTPAGTTSGASPVTPSPSPWDNGTESTPPQNATSPQAPSGQKT<br>AVPTVTSTGGKANSTTGGKHTTGHGARTSTEPTTDYGGDSTT<br>PRPRYNATTYLPPSTSSKLRPRWTFTSPPVTTAQATVPVPPTSQ | 4 |

TABLE 3-continued

Exemplary EBV Sequences
Sequences used in Examples 1 and 2 above

| | | |
|---|---|---|
| | PRFSNLSMLVLQWASLAVLTLLLLLVMADCAFRRNLSTSHTY<br>TTPPYDDAETYV | |
| PolyA tail | 100 nt | |
| **gH** | | **SEQ ID NO:** |
| SEQ ID NO: 18 consists of from 5' end to 3' end, 5' UTR SEQ ID NO: 1, mRNA ORF SEQ ID NO: 5, and 3' UTR SEQ ID NO: 3. | | 18 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUA<br>AGACCCCGGCGCCGCCACC | 1 |
| ORF of mRNA Construct (excluding the stop codon) | AUGCAGUUGUUGUGCGUGUUCUGCCUCGUGUUACUCUGG<br>GAGGUGGGCGCCGCCAGCCUUAGCGAGGUGAAGCUCCAC<br>UUGGACAUCGAGGGCCACGCCAGCCACUACACCAUCCCCU<br>GGACCGAGCUCAUGGCCAAGGUGCCCGGCCUUAGCCCCGA<br>GGCCCUGUGGCGGGAGGCCAACGUGACCGAGGACCUGGC<br>CAGCAUGCUGAACCGGUACAAGCUGAUCUACAAGACCAG<br>CGGCACCCUGGGCAUCGCCCUGGCCGAGCCCGUGGACAUC<br>CCCGCCGUUAGCGAAGGCAGCAUGCAGGUGGACGCCAGC<br>AAGGUGCACCCCGGCGUGAUCAGCGGCCUGAACAGCCCCG<br>CCUGUAUGUUGAGCGCCCCACUGGAGAAGCAGCUGUUCU<br>ACUACAUCGGCACCAUGCUGCCCAACACCCGGCCCCACAG<br>CUACGUGUUCUACCAGCUGCGGUGCCACCUGAGCUACGU<br>UGCCCUGAGCAUCAACGGCGACAAGUUCCAGUACACCGG<br>CGCCAUGACCAGCAAGUUCCUGAUGGGCACCUACAAGCG<br>GGUCACCGAGAAGGGCGACGAGCACGUGCUGUCACUGGU<br>GUUCGGCAAGACCAAGGACCUGCCCGACCUGCGGGGCCCC<br>UUCAGCUACCCUAGUUUGACCAGCGCCCAGAGCGGCGAC<br>UACAGCUUGGUGAUCGUGACCACCUUCGUGCACUACGCC<br>AACUUCCACAACUACUUCGUGCCCAACCUGAAGGACAUG<br>UUCAGCCGGGCCGUGACCAUGACUGCCGCUUCUUACGCCC<br>GGUACGUGCUGCAGAAGCUGGUCCUGCUGGAGAUGAAGG<br>GCGGCUGCCGGGAGCCCGAGCUGGACACCGAAACACUGA<br>CCACCAUGUUCGAGGUGAGCGUGGCCUUCUUCAAGGUGG<br>GUCACGCGGUGGGCGAAACCGGCAACGGCUGCGUGGACU<br>UACGCUGGCUGGCCAAGAGCUUCUUCGAGCUGACCGUGC<br>UGAAGGAUAUCAUCGGCAUCUGCUACGGCGCCACCGUGA<br>AGGGCAUGCAGAGCUACGGCCUGGAGCGGCUGGCCGCCA<br>UGCUUAUGGCAACAGUGAAGAUGGAGGAGCUGGGACACC<br>UGACAACAGAGAAGCAGGAGUACGCCCUGAGACUGGCCA<br>CAGUGGGCUACCCAAAGGCCGGCGUGUACAGUGGACUGA<br>UCGGCGGCGCAACCAGCGUGCUGCUAUCCGCUUACAACCG<br>GCACCCGCUGUUCCAGCCCCUGCACACCGUGAUGCGGGAA<br>ACCCUGUUCAUCGGAAGCCACGUCGUGCUGCGGGAGCUG<br>AGGCUGAACGUAACCACCCAGGGCCCUAAUCUGGCCCUG<br>UAUCAGCUCCUCAGUACCGCCCUGUGCAGCGCCCUUGAGA<br>UCGGCGAGGUGCUCAGAGGCCUGGCCCUCGGUACCGAGA<br>GCGGCCUCUUCAGCCCAUGCUACUUAAGCCUGCGGUUCG<br>ACCUGACCCGGGACAAGUUGCUGAGCAUGGCCCCGCAGG<br>AGGCCACACUGGACCAGGCAGCUGUAUCCAACGCCGUGG<br>ACGGCUUCCUGGGCAGACUGUCCCUGGAACGGGAGGACC<br>GGGACGCCUGGCACCUGCCUGCCUACAAGUGUGUGGAUC<br>GGCUGGACAAGGUGCUGAUGAUCAUCCCUCUGAUUAAUG<br>UCACCUUCAUCAUCAGCAGCGACCGGGAGGUGCGGGGAU<br>CCGCCCUCUACGAGGCCAGCACCACCUAUCUGAGCAGCAG<br>CCUGUUCCUGUCUCCUGUGAUCAUGAACAAGUGCAGCCA<br>GGGCGCCGUGGCCGGCGAGCCCCGGCAGAUCCCCAAGAUC<br>CAGAACUUCACCCGGACCCAGAAGUCUUGCAUCUUCUGC<br>GGCUUCGCCCUUUUGUCCUACGACGAGAAGGAGGGCUUG<br>GAGACUACAACCUACAUCACCAGCCAGGAGGUGCAGAAC<br>AGCAUCCUGUCAUCUAAUUACUUCGACUUCGACAACCUG<br>CACGUUCAUUACCUGCUCCUCACCACCAACGGUACCGUCA<br>UGGAAAUCGCCGGACUGUACGAGGAGCGGGCCCAUGUUG<br>UGCUGGCCAUCAUCCUGUACUUCAUCGCUUUCGCACUUG<br>GCAUCUUCCUGGUGCACAAGAUCGUGAUGUUCUUCCUG | 5 |
| 3' UTR | UGAUAAUAGGCUGGAGCCUCGGUGGCCUAGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGG<br>C | 3 |
| Corresponding amino acid sequence | MQLLCVFCLVLLWEVGAASLSEVKLHLDIEGHASHYTIPWTE<br>LMAKVPGLSPEALWREANVTEDLASMLNRYKLIYKTSGTLGI<br>ALAEPVDIPAVSEGSMQVDASKVHPGVISGLNSPACMLSAPLE<br>KQLFYYIGTMLPNTRPHSYVFYQLRCHLSYVALSINGDKFQYT<br>GAMTSKFLMGTYKRVTEKGDEHVLSLVFGKTKDLPDLRGPFS<br>YPSLTSAQSGDYSLVIVTTFVHYANFHNYFVPNLKDMFSRAV<br>TMTAASYARYVLQKLVLLEMKGGCREPELDTETLTTMFEVS | 6 |

TABLE 3-continued

Exemplary EBV Sequences
Sequences used in Examples 1 and 2 above

| | | |
|---|---|---|
| | VAFFKVGHAVGETGNGCVDLRWLAKSFFELTVLKDIIGICYG<br>ATVKGMQSYGLERLAAMLMATVKMEELGHLTTEKQEYALR<br>LATVGYPKAGVYSGLIGGATSVLLSAYNRHPLFQPLHTVMRE<br>TLFIGSHVVLRELRLNVTTQGPNLALYQLLSTALCSALEIGEVL<br>RGLALGTESGLFSPCYLSLRFDLTRDKLLSMAPQEATLDQAA<br>VSNAVDGFLGRLSLEREDRDAWHLPAYKCVDRLDKVLMIIPL<br>INVTFIISSDREVRGSALYEASTTYLSSSLFLSPVIMNKCSQGAV<br>AGEPRQIPKIQNFTRTQKSCIFCGFALLSYDEKEGLETTTYITSQ<br>EVQNSILSSNYFDFDNLHVHYLLLTTNGTVMEIAGLYEERAH<br>VVLAIILYFIAFALGIFLVHKIVMFFL | |
| PolyA tail | 100 nt | |
| **gL** | | **SEQ ID NO:** |
| SEQ ID NO: 19 consists of from 5' end to 3' end, 5' UTR SEQ ID NO: 1, mRNA ORF SEQ ID NO: 7, and 3' UTR SEQ ID NO: 3. | | 19 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUA<br>AGACCCCGGCGCCGCCACC | 1 |
| ORF of mRNA Construct (excluding the stop codon) | AUGAGAGCCGUGGGCGUGUUCCUGGCCAUCUGCCUGGUG<br>ACCAUCUUCGUGCUGCCCACCUGGGGCAACUGGGCCUACC<br>CCUGCUGCCACGUGACCCAGCUGAGAGCCCAGCACCUGCU<br>GGCCCUGGAGAACAUCAGCGACAUCUACCUGGUGAGCAA<br>CCAGACCUGCGACGGCUUCAGCCUGGCCAGCCUGAACAGC<br>CCCAAGAACGGCAGCAACCAGCUGGUGAUCAGCAGAUGC<br>GCCAACGGCCUGAACGUGGUGAGCUUCUUCAUCAGCAUC<br>CUGAAGAGAAGCAGCAGCGCCCUGACCGGCCACCUGAGA<br>GAGCUGCUGACCACCCUGGAGACCCUGUACGGCAGCUUC<br>AGCGUGGAGGACCUGUUCGGCGCCAACCUGAACAGAUAC<br>GCCUGGCACAGAGGCGGC | 7 |
| 3' UTR | UGAUAAUAGGCUGGAGCCUCGGUGGCCUAGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGG<br>C | 3 |
| Corresponding amino acid sequence | MRAVGVFLAICLVTIFVLPTWGNWAYPCCHVTQLRAQHLLA<br>LENISDIYLVSNQTCDGFSLASLNSPKNGSNQLVISRCANGLNV<br>VSFFISILKRSSSALTGHLRELLTTLETLYGSFSVEDLFGANLNR<br>YAWHRGG | 8 |
| PolyA tail | 100 nt | |
| **sol gp42** | | **SEQ ID NO:** |
| SEQ ID NO: 20 consists of from 5' end to 3' end, 5' UTR SEQ ID NO: 1, mRNA ORF SEQ ID NO: 9, and 3' UTR SEQ ID NO: 3. | | 20 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUA<br>AGACCCCGGCGCCGCCACC | 1 |
| ORF of mRNA Construct (excluding the stop codon) | AUGACCCGGCGGCGGGUGUUAAGCGUGGUGGUGCUCUUA<br>GCCGCCUUAGCCUGCCGGCUUGGCGCCAUCACCUGGGUGC<br>CCAAGCCCAACGUGGAGGUGUGGCCCGUGGACCCGCCACC<br>UCCCGUGAACUUCAACAAGACCGCCGAGCAGGAGUACGG<br>CGACAAGGAGGUGAAGCUGCCCCACUGGACGCCGACCCU<br>GCACACCUUCCAGGUGCCCCAGAACUACACCAAGGCCAAC<br>UGCACCUACUGCAACACCAGAGAGUACACCUUCAGCUAC<br>AAGGGCUGCUGCUUCUACUUCACCAAGAAGAAGCACACC<br>UGGAACGGCUGCUUCCAGGCCUGCGCCGAGCUGUACCCCU<br>GCACCUACUUCUACGGCCCCACCCCAGACAUCCUGCCCGU<br>GGUGACCAGAAACCUGAACGCCAUCGAGAGCCUGUGGGU<br>GGGCGUGUACAGAGUGGGCGAGGGCAACUGGACCAGCCU<br>GGACGGCGGCACCUUCAAGGUGUACCAGAUCUUCGGCAG<br>CCACUGCACCUACGUGAGCAAGUUCAGCACCGUGCCCGUG<br>AGCCACCACGAGUGCAGCUUCCUGAAGCCCUGCCUGUGCG<br>UGAGCCAGAGAAGCAACAGC | 9 |
| 3' UTR | UGAUAAUAGGCUGGAGCCUCGGUGGCCUAGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGGG<br>C | 3 |
| Corresponding amino acid sequence | MTRRRVLSVVVLLAALACRLGAITWVPKPNVEVWPVDPPPPV<br>NFNKTAEQEYGDKEVKLPHWTPTLHTFQVPQNYTKANCTYC<br>NTREYTFSYKGCCFYFTKKKHTWNGCFQACAELYPCTYFYGP<br>TPDILPVVTRNLNAIESLWVGVYRVGEGNWTSLDGGTFKVYQ<br>IFGSHCTYVSKFSTVPVSHHECSFLKPCLCVSQRSNS | 10 |
| PolyA tail | 100 nt | |

TABLE 3-continued

| Exemplary EBV Sequences<br>Sequences used in Examples 1 and 2 above | | |
|---|---|---|
| gB | | SEQ ID NO: |
| SEQ ID NO: 21 consists of from 5' end to 3' end, 5' UTR SEQ ID NO: 1, mRNA ORF SEQ ID NO: 11, and 3' UTR SEQ ID NO: 3. | | 21 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA<br>AGACCCCGGCGCCGCCACC | 1 |
| ORF of mRNA Construct (excluding the stop codon) | AUGACCCGGCGGCGGGUGUUAAGCGUGGUGGUGCUCUUA<br>GCCGCCUUAGCCUGCCGGCUUGGCGCCCAGACUCCGGAGC<br>AGCCCGCUCCUCCCGCCACCACCGUCCAGCCCACCGCCAC<br>CCGCCAGCAGACCUCCUUCCCCUUCCGCGUCUGCGAGCUC<br>UCCUCCCACGGCGACCUCUUCCGCUUCUCCUCCGACAUCC<br>AGUGCCCCUCCUUCGGCACCCGCGAGAACCACACCGAGGG<br>CCUCCUCAUGGUCUUCAAGGACAACAUCAUCCCCUACUCC<br>UUCAAGGUCCGCUCCUACACCAAGAUCGUCACCAACAUCC<br>UCAUCUACAACGGCUGGUACGCCGACUCUGUGACUAAUC<br>GCCACGAGGAGAAGUUCUCCGUCGACUCCUACGAGACUG<br>ACCAGAUGGACACCAUCUACCAGUGCUACAACGCCGUCA<br>AGAUGACCAAGGACGGCCUCACCCGCGUCUACGUCGACCG<br>CGACGGCGUCAACAUCACCGUCAACCUCAAGCCUACAGGC<br>GGCCUCGCCAACGGCGUCCGCCGCUACGCCUCCCAGACCG<br>AGCUCUACGACGCCCCUGGCUGGCUCAUCUGGACCUACCG<br>CACCAGGACCACUGUCAAUUGCCUCAUCACCGACAUGAU<br>GGCCAAGUCCAACUCCCCUUUCGACUUCUUCGUGACCACC<br>ACAGGCCAGACCGUCGAGAUGUCGCCAUUCUAUGACGGC<br>AAGAACAAGGAGACUUUCCACGAGAGAGCGGACUCUUUC<br>CAUGUCCGCACCAACUACAAGAUUGUCGACUACGACAAC<br>CGCGGCACCAAUCCACAGGGCGAGCGCCGCGCCUUCCUCG<br>ACAAGGGCACCUACACCCUCUCCUGGAAGCUCGAGAACCG<br>CACCGCCUACUGUCCUCUCCAGCACUGGCAGACCUUCGAU<br>UCCACCAUCGCCACCGAGACUGGCAAGUCCAUCCAUUUCG<br>UCACCGACGAAGGAACAUCUUCAUUCGUCACAAAUACAA<br>CCGUGGGCAUCGAGCUCCCCGACGCCUUCAAGUGCAUCGA<br>GGAGCAGGUCAACAAGACCAUGCACGAGAAGUACGAGGC<br>CGUCCAGGACCGGUAUACAAAGGGCCAGGAGGCCAUCAC<br>CUACUUCAUCACCAGCGGAGGUCUGCUUCUCGCCUGGCU<br>UCCACUCACACCUCGCUCCCUGGCCACAGUGAAGAACCUC<br>ACUGAGUUGACCACCCCAACAAGUUCCCCACCUAGUAGUC<br>CUAGCCCUCCUGCUCCUUCCGCCGCCCGCGGCUCCACGCC<br>UGCCGCCGUCCUGCGGAGACGGAGAAGGGACGCCGGCAA<br>CGCUACCACUCCUGUGCCGCCGACAGCCCCUGGAAAGUCC<br>CUAGGUACCCUCAACAACCCAGCGACAGUUCAGAUCCAG<br>UUCGCCUACGACUCUCUCAGGCGCCAGAUCAACCGCAUGC<br>UUGGUGACCUUGCCCGCGCCUGGUGCCUCGAGCAGAAGC<br>GCCAGAACAUGGUGCUUCGUGAACUAACAAAGAUUAAUC<br>CUACUACAGUGAUGUCCUCCAUCUACGGCAAGGCCGUCG<br>CCGCCAAGCGCCUCGGCGACGUCAUCUCCGUCUCCCAGUG<br>CGUCCCAGUGAACCAGGCUACCGUGACCCUCAGGAAGUCC<br>AUGAGAGUGCCAGGCUCCGAGACAAUGUGCUACUCCCGC<br>CCACUCGUCUCCUUCUCCUUCAUCAACGACACAAAGACCU<br>ACGAGGGCCAGUUAGGCACUGACAACGAGAUCUUCUUGA<br>CUAAGAAGAUGACUGAGGUAUGCCAGGCAACUUCUCAAU<br>ACUACUUCCAGUCUGGAAAUGAGAUCCACGUAUAUAACG<br>ACUACCACCACUUCAAGACUAUUGAACUCGACGGAAUUG<br>CCACCCUCCAAACAUUCAUCUCACUGAAUACCUCCCUCAU<br>CGAGAACAUCGACUUCGCCUCCCUCGAGCUGUAUAGCAG<br>AGACGAGCAGCGCGCCUCCAACGUCUUCGACCUCGAGGGC<br>AUCUUCCGCGAGUACAACUUCCAGGCACAGAACAUAGCC<br>GGCCUCCGUAAGGAUCUGGACAAUGCCGUGUCCAACGGC<br>CGCAACCAGUUCGUCGACGGUUUGGGUGAACUCAUGGAC<br>UCUCUGGGCUCCGUCGGCCAGUCCAUAACUAACUUAGUC<br>UCUACGGUGGGAGGCCUAUUCAGCAGCCUGGUGAGCGGC<br>UUCAUCUCUUUCUUCAAGAACCCCUUCGGCGGCAUGCUC<br>AUCCUCGUCCUCGUCGCCGGCGUCGUCAUACUGGUGAUC<br>UCACUCACAAGGAGGACGCGCCAAAUGUCCCAGCAGCCA<br>GUGCAGAUGCUCUACCCAGGCAUAGACGAGCUCGCUCAG<br>CAGCACGCGUCGGGUGAGGGACCAGGCAUCAAUCCUAUC<br>UCCAAGACUGAGCUGCAAGCCAUUAUGCUCGCCCUCCACG<br>AGCAGAACCAGGAACAGAAGCGGGCCGCCCAGCGAGCUG<br>CCGGCCCCUCCGUCGCCAGUAGGGCACUACAAGCCGCCCG<br>GGACCGCUUCCCAGGCCUGAGAAGGAGGAGAUACCACGA<br>CCCAGAGACAGCCGCUGCCCUCCUUGGCGAAGCAGAAACC<br>GAGUUC | 11 |
| 3' UTR | UGAUAAUAGGCUGGAGCCUCGGUGGCCUAGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGG | 3 |

TABLE 3-continued

| Exemplary EBV Sequences<br>Sequences used in Examples 1 and 2 above | | |
|---|---|---|
| | C | |
| Corresponding amino acid sequence | MTRRRVLSVVVLLAALACRLGAQTPEQPAPPATTVQPTATRQ<br>QTSFPFRVCELSSHGDLFRFSSDIQCPSFGTRENHTEGLLMVFK<br>DNIIPYSFKVRSYTKIVTNILIYNGWYADSVTNRHEEKFSVDSY<br>ETDQMDTIYQCYNAVKMTKDGLTRVYVDRDGVNITVNLKPT<br>GGLANGVRRYASQTELYDAPGWLIWTYRTRTTVNCLITDMM<br>AKSNSPFDFFVTTTGQTVEMSPFYDGKNKETFHERADSFHVR<br>TNYKIVDYDNRGTNPQGERRAFLDKGTYTLSWKLENRTAYC<br>PLQHWQTFDSTIATETGKSIHFVTDEGTSSFVTNTTVGIELPDA<br>FKCIEEQVNKTMHEKYEAVODRYTKGQEAITYFITSGGLLLA<br>WLPLTPRSLATVKNLTELTTPTSSPPSSPSPPAPSAARGSTPAA<br>VLRRRRRDAGNATTPVPPTAPGKSLGTLNNPATVQIQFAYDSL<br>RRQINRMLGDLARAWCLEQKRQNMVLRELTKINPTTVMSSIY<br>GKAVAAKRLGDVISVSQCVPVNQATVTLRKSMRVPGSETMC<br>YSRPLVSFSFINDTKTYEGQLGTDNEIFLTKKMTEVCQATSQY<br>YFQSGNEIHVYNDYHHFKTIELDGIATLQTFISLNTSLIENIDFA<br>SLELYSRDEQRASNVFDLEGIFREYNFQAQNIAGLRKDLDNAV<br>SNGRNQFVDGLGELMDSLGSVGQSITNLVSTVGGLFSSLVSGF<br>ISFFKNPFGGMLILVLVAGVVILVISLTRRTRQMSQQPVQMLY<br>PGIDELAQQHASGEGPGINPISKTELQAIMLALHEQNQEQKRA<br>AQRAAGPSVASRALQAARDRFPGLRRRRYHDPETAAALLGE<br>AETEF | 12 |
| PolyA tail | 100 nt | |
| WT gp42 | | SEQ ID NO: |
| SEQ ID NO: 22 consists of from 5' end to 3' end, 5' UTR SEQ ID NO: 1, mRNA ORF SEQ ID NO: 13, and 3' UTR SEQ ID NO: 3. | | 22 |
| Chemistry | 1-methylpseudouridine | |
| Cap | 7mG(5')ppp(5')NImpNp | |
| 5' UTR | GGGAAAUAAGAGAGAAAAGAAGAGUAAGAAGAAAUAUA<br>AGACCCCGGCGCCGCCACC | 1 |
| ORF of mRNA Construct (excluding the stop codon) | AUGGUGAGCUUCAAGCAGGUGAGAGUGCCCCUGUUCACC<br>GCCAUCGCCCUGGUGAUCGUGCUGCUGCUGGCCUACUUCC<br>UGCCACCCAGAGUGAGAGGCGGCGGCAGAGUGGCCGCCG<br>CCGCCAUCACCUGGGUGCCCAAGCCCAACGUGGAGGUGU<br>GGCCCGUGGACCCGCCACCUCCCGUGAACUUCAACAAGAC<br>CGCCGAGCAGGAGUACGGCGACAAGGAGGUGAAGCUGCC<br>CCACUGGACGCCGACCCUGCACACCUUCCAGGUGCCCCAG<br>AACUACACCAAGGCCAACUGCACCUACUGCAACACCAGAG<br>AGUACACCUUCAGCUACAAGGGCUGCUGCUUCUACUUCA<br>CCAAGAAGAAGCACACCUGGAACGGCUGCUUCCAGGCCU<br>GCGCCGAGCUGUACCCCUGCACCUACUUCUACGGCCCCAC<br>CCCAGACAUCCUGCCCGUGGUGACCAGAAACCUGAACGCC<br>AUCGAGAGCCUGUGGGUGGGCGUGUACAGAGUGGGCGAG<br>GGCAACUGGACCAGCCUGGACGGCGGCACCUUCAAGGUG<br>UACCAGAUCUUCGGCAGCCACUGCACCUACGUGAGCAAG<br>UUCAGCACCGUGCCCGUGAGCCACCACGAGUGCAGCUUCC<br>UGAAGCCCUGCCUGUGCGUGAGCCAGAGAAGCAACAGC | 13 |
| 3' UTR | UGAUAAUAGGCUGGAGCCUCGGUGGCCUAGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGG<br>C | 3 |
| Corresponding amino acid sequence | MVSFKQVRVPLFTAIALVIVLLLAYFLPPRVRGGGRVAAAAIT<br>WVPKPNVEVWPVDPPPPVNFNKTAEQEYGDKEVKLPHWTPT<br>LHTFQVPQNYTKANCTYCNTREYTFSYKGCCFYFTKKKHTW<br>NGCFQACAELYPCTYFYGPTPDILPVVTRNLNAIESLWVGVYR<br>VGEGNWTSLDGGTFKVYQIFGSHCTYVSKFSTVPVSHHECSFL<br>KPCLCVSQRSNS | 14 |
| PolyA tail | 100 nt | |
| gp350 | | SEQ ID NO: |
| SEQ ID NO: 23 consists of from 5' end to 3' end, 5' UTR SEQ ID NO: 1, mRNA ORF SEQ ID NO: 15, and 3' UTR SEQ ID NO: 3. | | 23 |
| Chemistry | 1-methylpseudouridine | |
| Cap | 7mG(5')ppp(5')NImpNp | |
| 5' UTR | GGGAAAUAAGAGAGAAAAGAAGAGUAAGAAGAAAUAUA<br>AGACCCCGGCGCCGCCACC | 1 |
| ORF of mRNA Construct (excluding the stop codon) | AUGGAGGCAGCACUGCUGGUCUGCCAGUAUACAAUCCAG<br>UCGCUCAUUCAUCUGACAGGCGAGGACCCCGGCUUCUUU<br>AACGUGGAAAUCCCAGAGUUCCCUUUCUAUCCAACCUGU<br>AACGUUUGCACUGCUGACGUGAACGUGACAAUCAAUUUC<br>GACGUGGGAGGAAAGAAGCAUCAGCUUGAUCUGGAUUUC<br>GGCCAACUGACGCCACACACCAAAGCGGUGUACCAACCAA<br>GGGGUGCAUUUGGAGGGAGCGAGAAUGCUACAAAUCUGU<br>UCUUACUGGAACUGCUUGGUGCAGGAGAGCUGGCACUAA | 15 |

TABLE 3-continued

| Exemplary EBV Sequences<br>Sequences used in Examples 1 and 2 above | | |
|---|---|---|
| | CCAUGCGAAGCAAGAAGCUCCCCAUCAACGUUACCACCGG<br>GGAAGAACAGCAAGUCAGCCUUGAAUCCGUGGAUGUGUA<br>CUUUCAGGAUGUUUUCGGCACCAUGUGGUGUCACCACGC<br>UGAGAUGCAGAAUCCCGUGUAUCUCAUACCCGAGACUGU<br>ACCCUACAUCAAGUGGGAUAAUUGCAAUUCAACUAAUAU<br>UACGGCUGUGGUGAGGGCCCAGGGCUUGGACGUGACUCU<br>GCCCUUAUCUCUACCUACUUCUGCCCAAGACUCCAAUUUC<br>UCUGUCAAGACCGAGAUGCUCGGGAAUGAGAUCGAUAUC<br>GAGUGCAUCAUGGAGGACGGUGAGAUAAGCCAGGUUCUG<br>CCCGGCGACAACAAGUUCAAUAUCACUUGUUCUGGCUAC<br>GAGUCCCAUGUGCCUAGUGGUGGCAUACUCACAAGUACU<br>UCUCCCGUAGCCACGCCCAUUCCCGGAACCGGAUACGCCU<br>ACAGUCUGCGUCUGACCCCACGGCCUGUGUCCAGAUUCCU<br>GGGUAACAAUAGUAUCUUAUACGUGUUUUAUAGCGGAAA<br>CGGCCCUAAAGCGUCCGGAGGGGACUAUUGUAUUCAGAG<br>UAAUAUCGUUUUCUCUGAUGAGAUUCCUGCCAGUCAGGA<br>CAUGCCGACAAACACAACUGAUAUUACCUACGUGGGCGA<br>CAAUGCCACGUAUUCAGUGCCCAUGGUCACGAGCGAGGA<br>CGCCAAUUCACCAAAUGUUACUGUAACAGCUUUCUGGGC<br>CUGGCCAAAUAACACUGAGACUGACUUCAAAUGUAAGUG<br>GACUUUGACCUCUGGAACUCCGUCGGGUUGCGAGAAUAU<br>CAGCGGGGCCUUUGCUUCCAACAGGACUUUCGACAUCAC<br>UGUCUCAGGGCUGGGGACAGCACCGAAGACAUUAAUCAU<br>AACACGGACCGCCACCAACGCCACGACUACAACCCAUAAG<br>GUGAUCUUUUCCAAGGCACCUGAGUCCACCACUACCUCCC<br>CGACUCUUAACACUACGGGCUUCGCUGAUCCCAACACCAC<br>UACGGGGUUGCCUAGCUCGACACAUGUGCCGACGAACCU<br>GACUGCCCCUGCAUCGACCGGGCCCACAGUUUCGACCGCC<br>GAUGUGACAUCACCAACGCCCGCAGGUACAACCUCAGGC<br>GCCAGCCCAGUGACCCCUUCCCCAAGCCCCUGGGAUAAUG<br>GAACGGAGUCCAAGGCUCCUGAUAUGACUUCCUCUACCA<br>GCCCCGUGACUACACCCACUCCCAACGCAACUAGCCCAAC<br>CCCAGCUGUGACGACGCCCACCCCGAACGCGACAUCUCCC<br>ACACCUGCUGUGACAACCCCAACCCCUAACGCCACUAGCC<br>CUACCCUAGGUAAGACCAGUCCGACUAGCGCCGUUACAA<br>CCCCUACCCCUAACGCAACCGGCCCGACCGUGGGCGAGAC<br>UUCCCCGCAAGCCAAUGCGACAAAUCACACAUUGGGCGG<br>GACCUCUCCUACACCAGUCGUUACAUCUCAGCCUAAGAAC<br>GCUACCUCCGCUGUCACUACCGGACAGCACAACAUCACCA<br>GCUCAAGCACGAGUUCCAUGAGCUUGCGGCCGAGCUCAA<br>AUCCCGAGACCCUAUCACCAUCCACAUCAGACAACAGUAC<br>UUCACACAUGCCACUCUUGACGAGCGCUCACCCCACCGGC<br>GGCGAGAACAUCACCCAGGUGACUCCGGCGUCUAUUUCC<br>ACCCACCACGUCAGCACGUCGUCUCCCGCACCGAGACCAG<br>GGACGACUUCUCAGGCCAGUGGGCCUGGCAACUCCUCUA<br>CAAGCACAAAGCCAGGCGAAGUUAACGUGACAAAGGGAA<br>CGCCUCCCCAGAACGCAACCAGUCCUCAGGCGCCCAGCGG<br>GCAGAAGACUGCGGUGCCAACUGUGACCAGCACCGGUGG<br>CAAGGCCAACUCAACAACUGGAGGCAAGCAUACGACGGG<br>GCACGGCGCCCGGACCUCCACUGAACCCACGACCGAUUAC<br>GGAGGUGACAGCACAACACCGCGGCCACGAUAUAAUGCC<br>ACCACUUAUCUGCCACCAUCCACAAGCUCCAAGCUGCGGC<br>CACGGUGGACCUUCACAAGCCCACCCGUGACGACUGCCCA<br>AGCGACGGUGCCAGUGCCACCUACAAGCCAGCCACGCUUC<br>UCCAACCUUAGUAUGCUCGUUCUCCAGUGGGCCAGCCUU<br>GCUGUUCUGACCCUCCUCCUGCUGCUCGUGAUGGCCGAU<br>UGCGCCUUUAGGAGAAACCUCAGCACUAGCCACACGUAC<br>ACCACGCCGCCCUACGAUGACGCCGAGACUUACGUC | |
| 3' UTR | UGAUAAUAGGCUGGAGCCUCGGUGGCCUAGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGG<br>C | 3 |
| Corresponding amino acid sequence | MEAALLVCQYTIQSLIHLTGEDPGFFNVEIPEFPFYPTCNVCTA<br>DVNVTINFDVGGKKHQLDLDFGQLTPHTKAVYQPRGAFGGS<br>ENATNLFLLELLGAGELALTMRSKKLPINVTTGEEQQVSLESV<br>DVYFQDVFGTMWCHHAEMQNPVYLIPETVPYIKWDNCNSTN<br>ITAVVRAQGLDVTLPLSLPTSAQDSNFSVKTEMLGNEIDIECIM<br>EDGEISQVLPGDNKFNITCSGYESHVPSGGILTSTSPVATPIPGT<br>GYAYSLRLTPRPVSRFLGNNSILYVFYSGNGPKASGGDYCIQS<br>NIVFSDEIPASQDMPTNTTDITYVGDNATYSVPMVTSEDANSP<br>NVTVTAFWAWPNNTETDFKCKWTLTSGTPSGCENISGAFASN<br>RTFDITVSGLGTAPKTLIITRTATNATTTTHKVIFSKAPESTTTS<br>PTLNTTGFADPNTTTGLPSSTHVPTNLTAPASTGPTVSTADVTS<br>PTPAGTTSGASPVTPSPSPWDNGTESKAPDMTSSTSPVTTPTPN<br>ATSPTPAVTTPTPNATSPTPAVTTPTPNATSPTLGKTSPTSAVT<br>TPTPNATGPTVGETSPQANATNHTLGGTSPTPVVTSQPKNATS<br>AVTTGQHNITSSSTSSMSLRPSSNPETLSPSTSDNSTSHMPLLTS | 16 |

TABLE 3-continued

| Exemplary EBV Sequences Sequences used in Examples 1 and 2 above | |
|---|---|
| | AHPTGGENITQVTPASISTHHVSTSSPAPRPGTTSQASGPGNSS TSTKPGEVNVTKGTPPQNATSPQAPSGQKTAVPTVTSTGGKA NSTTGGKHTTGHGARTSTEPTTDYGGDSTTPRPRYNATTYLPP STSSKLRPRWTFTSPPVTTAQATVPVPPTSQPRFSNLSMLVLQ WASLAVLTLLLLLVMADCAFRRNLSTSHTYTTPPYDDAETYV |
| PolyA tail | 100 nt |

It should be understood that any one of the sequences of Table 3 may be fully modified by N1-methylpseudoruidine.

What is claimed is:

1. An immunogenic composition, comprising a lipid nanoparticle that comprises:

(a) a messenger ribonucleic acid (mRNA) comprising an open reading frame encoding an Epstein-Barr virus (EBV) glycoprotein 220 (gp220);

(b) an mRNA comprising an open reading frame encoding a soluble EBV glycoprotein 42 (gp42);

(c) an mRNA comprising an open reading frame encoding an EBV glycoprotein L (gL); and (d) an mRNA comprising an open reading frame encoding an EBV glycoprotein H (gH).

2. The immunogenic composition of claim 1, wherein:

the mRNA of (a) is at a mass 5 times, 4.5 times, 4 times, 3.5 times, 3 times, 2.5 times, 2 times, or 1.5 times the mass of the mRNA of (b), the mRNA of (c), and/or the mRNA of (d);

the mRNA of (b) is at a mass 5 times, 4.5 times, 4 times, 3.5 times, 3 times, 2.5 times, 2 times, or 1.5 times the mass of the mRNA of (a), the mRNA of (c), and/or the mRNA of (d);

the mRNA of (c) is at a mass 5 times, 4.5 times, 4 times, 3.5 times, 3 times, 2.5 times, 2 times, or 1.5 times the mass of the mRNA of (a), the mRNA of (b), and/or the mRNA of (d); or the mRNA of (d) is at a mass 5 times, 4.5 times, 4 times, 3.5 times, 3 times, 2.5 times, 2 times, or 1.5 times the mass of the mRNA of (a), the mRNA of (b), and/or the mRNA of (c).

3. The immunogenic composition of claim 1, wherein:

the mRNA of (a) is at equal mass to the mRNA of (b), the mRNA of (c), and/or the mRNA of (d);

the mRNA of (b) is at equal mass to the mRNA of (a), the mRNA of (c), and/or the mRNA of (d);

the mRNA of (c) is at equal mass to the mRNA of (a), the mRNA of (b), and/or the mRNA of (d); or the mRNA of (d) is at equal mass to the mRNA of (a), the mRNA of (b), and/or the mRNA of (c).

4. The immunogenic composition of claim 1, wherein the mass ratio of the mRNA of (a):the mRNA of (b):the mRNA of (c):the mRNA of (d) is 4:1:1:1.5.

5. The immunogenic composition of claim 1, wherein the mass ratio of the mRNA of (a):the mRNA of (b):the mRNA of (c):the mRNA of (d) is 4:1:1:1.

6. The immunogenic composition of claim 1, wherein the immunogenic composition comprises 26.7 μg of the mRNA encoding EBV gp220, 6.7 μg of the mRNA encoding soluble EBV gp42, 6.7 μg of the mRNA encoding EBV gL, and 10 μg of the mRNA encoding EBV gH.

7. The immunogenic composition of claim 1, wherein the immunogenic composition comprises 53.3 μg of the mRNA encoding EBV gp220, 13.3 μg of the mRNA encoding soluble EBV gp42, 13.3 μg of the mRNA encoding EBV gL, and 20 μg of the mRNA encoding EBV gH.

8. The immunogenic composition of claim 1, wherein the lipid nanoparticle further comprises (e) an mRNA comprising an open reading frame encoding EBV glycoprotein B (gB).

9. The immunogenic composition of claim 8, wherein the mass ratio of the mRNA of (a):the mRNA of (b):the mRNA of (c):the mRNA of (d):the mRNA of (e) is 4:1:1:1.5:1.5.

10. The immunogenic composition of claim 1, wherein;

the EBV gp220 comprises an amino acid sequence having at least 85% identity to the amino acid sequence of SEQ ID NO: 4.

11. The immunogenic composition of claim 10, wherein;

the EBV gp220 comprises the amino acid sequence of SEQ ID NO: 4.

12. The immunogenic composition of claim 1, wherein the soluble EBV gp42 comprises an amino acid sequence having at least 85% identity to the amino acid sequence of SEQ ID NO: 10.

13. The immunogenic composition of claim 12, wherein the soluble EBV gp42 comprises the amino acid sequence of SEQ ID NO: 10.

14. The immunogenic composition of claim 1, wherein the mRNA of any one or more of (a)-(d) comprises a 1-methylpseudourine chemical modification.

15. The immunogenic composition of claim 1, wherein the lipid nanoparticle comprises 45-55 mol % of an ionizable amino lipid, 15-20 mol % of a neutral lipid, 35-45 mol % of cholesterol, and 0.5-5 mol % of a PEG-modified lipid.

16. The immunogenic composition of claim 15, wherein the ionizable amino lipid is Compound I:

(Compound I)

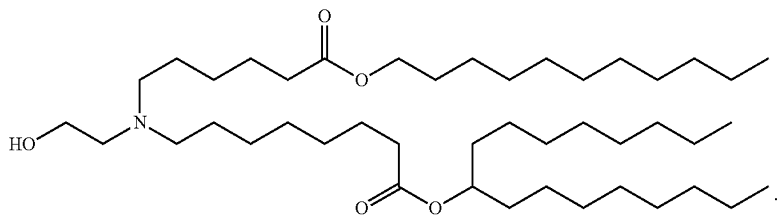

17. A method of inducing an immune response to EBV in a human subject, comprising administering to the human subject the immunogenic composition of claim 1 in an amount effective to induce an immune response to EBV.

18. The immunogenic composition of claim 1, wherein the EBV gL comprises an amino acid sequence having at least 85% identity to the amino acid sequence of SEQ ID NO: 8.

19. The immunogenic composition of claim 18, wherein the EBV gL comprises the amino acid sequence of SEQ ID NO: 8.

20. The immunogenic composition of claim 1, wherein the EBV gH comprises an amino acid sequence having at least 85% identity to the amino acid sequence of SEQ ID NO: 6.

21. The immunogenic composition of claim 20, wherein the EBV gH comprises the amino acid sequence of SEQ ID NO: 6.

22. The immunogenic composition of claim 1, wherein:

(a) the EBV gp220 comprises an amino acid sequence having at least 85% identity to the amino acid sequence of SEQ ID NO: 4;

(b) the soluble EBV gp42 comprises an amino acid sequence having at least 85% identity to the amino acid sequence of SEQ ID NO: 10;

(c) the EBV gL comprises an amino acid sequence having at least 85% identity to the amino acid sequence of SEQ ID NO: 8; and (d) the EBV gH comprises an amino acid sequence having at least 85% identity to the amino acid sequence of SEQ ID NO: 6.

23. The immunogenic composition of claim 1, wherein:

(a) the EBV gp220 comprises the amino acid sequence of SEQ ID NO: 4;

(b) the soluble EBV gp42 comprises the amino acid sequence of SEQ ID NO: 10;

(c) the EBV gL comprises the amino acid sequence of SEQ ID NO: 8; and (d) the EBV gH comprises the amino acid sequence of SEQ ID NO: 6.

24. The immunogenic composition of claim 23, wherein the mass ratio of the mRNA of (a):the mRNA of (b):the mRNA of (c):the mRNA of (d) is 4:1:1:1.5.

* * * * *

SEQUENCE LISTING

<160> NUMBER OF SEQ ID NOS: 34

<210> SEQ ID NO 1
<211> LENGTH: 57
<212> TYPE: RNA
<213> ORGANISM: Artificial Sequence
<220> FEATURE:
<223> OTHER INFORMATION: Synthetic

<400> SEQUENCE: 1
gggaaauaag agagaaaaga agaguaagaa gaaauauaag accccggcgc cgccacc 57

<210> SEQ ID NO 2
<211> LENGTH: 1974
<212> TYPE: RNA
<213> ORGANISM: Artificial Sequence
<220> FEATURE:
<223> OTHER INFORMATION: Synthetic

<400> SEQUENCE: 2
auggaggcag cacugcuggu cugccaguau acaauccagu cgcucauuca ucugacaggc 60
gaggaccccg gcuucuuuaa cguggaaauc ccagaguucc cuuucuaucc aaccuguaac 120
guuugcacug cugacgugaa cgugacaauc aauuucgacg ugggaggaaa gaagcaucag 180
cuugaucugg auuucggcca acugacgcca cacaccaaag cgguguacca accaaggggu 240
gcauuuggag ggagcgagaa ugcuacaaac cuguucuuac uggaacugcu uggugcagga 300
gagcuggcac uaaccaugcg aagcaagaag cuccccauca acguuaccac cggggaagaa 360
cagcaaguca gccuugaauc cguggaugug uacuuucagg auguuuucgg caccaugugg 420
ugucaccacg cugagaugca gaaucccgug uaucucauac ccgagacugu acccuacauc 480
aagugggaua auugcaauuc aacuaauauu acggcugugg ugagggccca gggcuuggac 540
gugacucugc ccuuaucucu accuacuucu gcccaagacu ccaauuucuc ugucaagacc 600
gagaugcucg ggaaugagau cgauaucgag ugcaucaugg aggacgguga gauaagccag 660
guucugcccg gcgacaacaa guucaauauc acuuguucug gcuacgaguc ccaugugccu 720
agugguggca uacucacaag uacuucuccc guagccacgc ccauucccgg aaccggauac 780
gccuacaguc ugcgucugac cccacggccu guguccagau uccugggguaa caauaguauc 840 uuauacgugu uuuauagcgg aaacggcccu aaagcguccg gaggggacua uuguauucag 900
aguaauaucg uuuucucuga ugagauuccu gccagucagg acaugccgac aaacacaacu 960
gauauuaccu acgugggcga caaugccacg uauucagugc ccauggucac gagcgaggac 1020
gccaauucac caaauguuac uguaacagcu uucugggccu ggccaaauaa cacugagacu 1080
gacuucaaau guaaguggac uuugaccucu ggaacuccgu cgguugcga gaauaucagc 1140 ggggccuuug cuuccaacag gacuuucgac aucacugucu cagggcuggg gacagcaccg 1200
aagacauuaa ucauaacacg gaccgccacc aacgccacga cuacaaccca uaaggugauc 1260
uuuuccaagg caccugaguc caccacuacc ucccgacuc uuaacacuac gggcuucgcu 1320
gaucccaaca ccacuacggg guugccuagc ucgacacaug ugccgacgaa ccugacugcc 1380
ccugcaucga ccgggcccac aguuucgacc gccgauguga caucaccaac gcccgcaggu 1440
acaaccucag gcgccagccc agugaccccu uccccaagcc ccugggauaa uggaacggag 1500
uccacgccuc cccagaacgc aaccaguccu caggcgccca gcgggcagaa gacugcggug 1560
ccaacuguga ccagcaccgg uggcaaggcc aacucaacaa cuggaggcaa gcauacgacg 1620
gggcacggcg cccggaccuc cacugaaccc acgaccgauu acggagguga cagcacaaca 1680
ccgcggccac gauauaaugc caccacuuau cugccaccau ccacaagcuc caagcugcgg 1740
ccacggugga ccuucacaag cccacccgug acgacugccc aagcgacggu gccagugcca 1800
ccuacaagcc agccacgcuu cuccaaccuu aguaugcucg uucuccagug ggccagccuu 1860
gcuguucuga cccuccuccu gcugcucgug auggccgauu gcgccuuuag gagaaaccuc 1920
agcacuagcc acacguacac cacgccgccc uacgaugacg ccgagacuua cguc 1974

<210> SEQ ID NO 3
<211> LENGTH: 119
<212> TYPE: RNA
<213> ORGANISM: Artificial Sequence
<220> FEATURE:
<223> OTHER INFORMATION: Synthetic

<400> SEQUENCE: 3
ugauaauagg cuggagccuc gguggccuag cuucuugccc cuugggccuc cccccagccc 60
cuccuccccu uccugcaccc guacccccgu ggucuuugaa uaaagucuga gugggcggc 119

<210> SEQ ID NO 4
<211> LENGTH: 658
<212> TYPE: PRT
<213> ORGANISM: Artificial Sequence
<220> FEATURE:
<223> OTHER INFORMATION: Synthetic

<400> SEQUENCE: 4

Met Glu Ala Ala Leu Leu Val Cys Gln Tyr Thr Ile Gln Ser Leu Ile
1 5 10 15

His Leu Thr Gly Glu Asp Pro Gly Phe Phe Asn Val Glu Ile Pro Glu
20 25 30

Phe Pro Phe Tyr Pro Thr Cys Asn Val Cys Thr Ala Asp Val Asn Val
35 40 45

Thr Ile Asn Phe Asp Val Gly Gly Lys Lys His Gln Leu Asp Leu Asp
50 55 60

Phe Gly Gln Leu Thr Pro His Thr Lys Ala Val Tyr Gln Pro Arg Gly
65 70 75 80

Ala Phe Gly Gly Ser Glu Asn Ala Thr Asn Leu Phe Leu Leu Glu Leu
85 90 95

Leu Gly Ala Gly Glu Leu Ala Leu Thr Met Arg Ser Lys Lys Leu Pro
100 105 110

Ile Asn Val Thr Thr Gly Glu Glu Gln Gln Val Ser Leu Glu Ser Val
115 120 125

Asp Val Tyr Phe Gln Asp Val Phe Gly Thr Met Trp Cys His His Ala
130 135 140

```
Glu Met Gln Asn Pro Val Tyr Leu Ile Pro Glu Thr Val Pro Tyr Ile
145                 150                 155                 160

Lys Trp Asp Asn Cys Asn Ser Thr Asn Ile Thr Ala Val Val Arg Ala
                165                 170                 175

Gln Gly Leu Asp Val Thr Leu Pro Leu Ser Leu Pro Thr Ser Ala Gln
            180                 185                 190

Asp Ser Asn Phe Ser Val Lys Thr Glu Met Leu Gly Asn Glu Ile Asp
        195                 200                 205

Ile Glu Cys Ile Met Glu Asp Gly Glu Ile Ser Gln Val Leu Pro Gly
    210                 215                 220

Asp Asn Lys Phe Asn Ile Thr Cys Ser Gly Tyr Glu Ser His Val Pro
225                 230                 235                 240

Ser Gly Gly Ile Leu Thr Ser Thr Ser Pro Val Ala Thr Pro Ile Pro
                245                 250                 255

Gly Thr Gly Tyr Ala Tyr Ser Leu Arg Leu Thr Pro Arg Pro Val Ser
            260                 265                 270

Arg Phe Leu Gly Asn Asn Ser Ile Leu Tyr Val Phe Tyr Ser Gly Asn
        275                 280                 285

Gly Pro Lys Ala Ser Gly Gly Asp Tyr Cys Ile Gln Ser Asn Ile Val
    290                 295                 300

Phe Ser Asp Glu Ile Pro Ala Ser Gln Asp Met Pro Thr Asn Thr Thr
305                 310                 315                 320

Asp Ile Thr Tyr Val Gly Asp Asn Ala Thr Tyr Ser Val Pro Met Val
                325                 330                 335

Thr Ser Glu Asp Ala Asn Ser Pro Asn Val Thr Val Thr Ala Phe Trp
            340                 345                 350

Ala Trp Pro Asn Asn Thr Glu Thr Asp Phe Lys Cys Lys Trp Thr Leu
        355                 360                 365

Thr Ser Gly Thr Pro Ser Gly Cys Glu Asn Ile Ser Gly Ala Phe Ala
    370                 375                 380

Ser Asn Arg Thr Phe Asp Ile Thr Val Ser Gly Leu Gly Thr Ala Pro
385                 390                 395                 400

Lys Thr Leu Ile Ile Thr Arg Thr Ala Thr Asn Ala Thr Thr Thr Thr
                405                 410                 415

His Lys Val Ile Phe Ser Lys Ala Pro Glu Ser Thr Thr Thr Ser Pro
            420                 425                 430

Thr Leu Asn Thr Thr Gly Phe Ala Asp Pro Asn Thr Thr Thr Gly Leu
        435                 440                 445

Pro Ser Ser Thr His Val Pro Thr Asn Leu Thr Ala Pro Ala Ser Thr
    450                 455                 460

Gly Pro Thr Val Ser Thr Ala Asp Val Thr Ser Pro Thr Pro Ala Gly
465                 470                 475                 480

Thr Thr Ser Gly Ala Ser Pro Val Thr Pro Ser Pro Ser Pro Trp Asp
                485                 490                 495

Asn Gly Thr Glu Ser Thr Pro Pro Gln Asn Ala Thr Ser Pro Gln Ala
            500                 505                 510

Pro Ser Gly Gln Lys Thr Ala Val Pro Thr Val Thr Ser Thr Gly Gly
        515                 520                 525

Lys Ala Asn Ser Thr Thr Gly Gly Lys His Thr Thr Gly His Gly Ala
    530                 535                 540

Arg Thr Ser Thr Glu Pro Thr Thr Asp Tyr Gly Gly Asp Ser Thr Thr
545                 550                 555                 560
```

-continued

```
Pro Arg Pro Arg Tyr Asn Ala Thr Thr Tyr Leu Pro Pro Ser Thr Ser
                565                 570                 575

Ser Lys Leu Arg Pro Arg Trp Thr Phe Thr Ser Pro Pro Val Thr Thr
            580                 585                 590

Ala Gln Ala Thr Val Pro Val Pro Pro Thr Ser Gln Pro Arg Phe Ser
        595                 600                 605

Asn Leu Ser Met Leu Val Leu Gln Trp Ala Ser Leu Ala Val Leu Thr
    610                 615                 620

Leu Leu Leu Leu Leu Val Met Ala Asp Cys Ala Phe Arg Arg Asn Leu
625                 630                 635                 640

Ser Thr Ser His Thr Tyr Thr Thr Pro Pro Tyr Asp Asp Ala Glu Thr
                645                 650                 655

Tyr Val


<210> SEQ ID NO 5
<211> LENGTH: 2118
<212> TYPE: RNA
<213> ORGANISM: Artificial Sequence
<220> FEATURE:
<223> OTHER INFORMATION: Synthetic

<400> SEQUENCE: 5

augcaguugu ugugcguguu cugccucgug uuacucuggg aggugggcgc cgccagccuu     60

agcgagguga agcuccacuu ggacaucgag ggccacgcca gccacuacac cauccccugg    120

accgagcuca uggccaaggu gcccggccuu agccccgagg cccuguggcg ggaggccaac    180

gugaccgagg accuggccag caugcugaac cgguacaagc ugaucuacaa gaccagcggc    240

acccugggca ucgcccuggc cgagcccgug gacauccccg ccguuagcga aggcagcaug    300

cagguggacg ccagcaaggu gcaccccggc gugaucagcg gccugaacag ccccgccugu    360

auguugagcg ccccacugga gaagcagcug uucuacuaca ucggcaccau gcugcccaac    420

acccggcccc acagcuacgu guucuaccag cugcggugcc accugagcua cguugcccug    480

agcaucaacg gcgacaaguu ccaguacacc ggcgccauga ccagcaaguu ccugaugggc    540

accuacaagc gggucaccga gaagggcgac gagcacgugc ugucacuggu guucggcaag    600

accaaggacc ugcccgaccu gcggggcccc uucagcuacc cuaguuugac cagcgcccag    660

agcggcgacu acagcuuggu gaucgugacc accuucgugc acuacgccaa cuuccacaac    720

uacuucgugc ccaaccugaa ggacauguuc agccgggccg ugaccaugac ugccgcuucu    780

uacgcccggu acgugcugca gaagcugguc cugcuggaga ugaagggcgg cugccgggag    840

cccgagcugg acaccgaaac acugaccacc auguucgagg ugagcguggc cuucuucaag    900

gugggucacg cggugggcga aaccggcaac ggcugcgugg acuuacgcug gcuggccaag    960

agcuucuucg agcugaccgu gcugaaggau aucaucggca ucugcuacgg cgccaccgug   1020

aagggcaugc agagcuacgg ccuggagcgg cuggccgcca ugcuuauggc aacagugaag   1080

auggaggagc ugggacaccu gacaacagag aagcaggagu acgcccugag acuggccaca   1140

gugggcuacc caaaggccgg cguguacagu ggacugaucg gcggcgcaac cagcgugcug   1200

cuauccgcuu acaaccggca cccgcuguuc cagccccugc acaccgugau gcgggaaacc   1260

cuguucaucg gaagccacgu cgugcugcgg gagcugaggc ugaacguaac cacccagggc   1320

ccuaaucugg cccuguauca gcuccucagu accgcccugu gcagcgcccu ugagaucggc   1380

gaggugcuca gaggccuggc ccucgguacc gagagcggcc ucuucagccc augcuacuua   1440

agccugcggu ucgaccugac ccgggacaag uugcugagca uggccccgca ggaggccaca   1500
```

cuggaccagg cagcuguauc caacgccgug gacggcuucc ugggcagacu gucccuggaa 1560
cgggaggacc gggacgccug gcaccugccu gccuacaagu guguggaucg gcuggacaag 1620
gugcugauga ucaucccucu gauuaauguc accuucauca ucagcagcga ccgggaggug 1680
cggggauccg cccucuacga ggccagcacc accuaucuga gcagcagccu guuccugucu 1740
ccugugauca ugaacaagug cagccagggc gccguggccg gcgagccccg gcagaucccc 1800
aagauccaga acuucacccg gacccagaag ucuugcaucu ucugcggcuu cgcccuuuug 1860
uccuacgacg agaaggaggg cuuggagacu acaaccuaca ucaccagcca ggaggugcag 1920
aacagcaucc ugucaucuaa uuacuucgac uucgacaacc ugcacguuca uuaccugcuc 1980
cucaccacca acgguaccgu cauggaaauc gccggacugu acgaggagcg ggcccauguu 2040
gugcuggcca ucauccugua cuucaucgcu uucgcacuug gcaucuuccu ggugcacaag 2100
aucgugaugu ucuuccug 2118

<210> SEQ ID NO 6
<211> LENGTH: 706
<212> TYPE: PRT
<213> ORGANISM: Artificial Sequence
<220> FEATURE:
<223> OTHER INFORMATION: Synthetic

<400> SEQUENCE: 6

Met Gln Leu Leu Cys Val Phe Cys Leu Val Leu Leu Trp Glu Val Gly
1 5 10 15

Ala Ala Ser Leu Ser Glu Val Lys Leu His Leu Asp Ile Glu Gly His
20 25 30

Ala Ser His Tyr Thr Ile Pro Trp Thr Glu Leu Met Ala Lys Val Pro
35 40 45

Gly Leu Ser Pro Glu Ala Leu Trp Arg Glu Ala Asn Val Thr Glu Asp
50 55 60

Leu Ala Ser Met Leu Asn Arg Tyr Lys Leu Ile Tyr Lys Thr Ser Gly
65 70 75 80

Thr Leu Gly Ile Ala Leu Ala Glu Pro Val Asp Ile Pro Ala Val Ser
85 90 95

Glu Gly Ser Met Gln Val Asp Ala Ser Lys Val His Pro Gly Val Ile
100 105 110

Ser Gly Leu Asn Ser Pro Ala Cys Met Leu Ser Ala Pro Leu Glu Lys
115 120 125

Gln Leu Phe Tyr Tyr Ile Gly Thr Met Leu Pro Asn Thr Arg Pro His
130 135 140

Ser Tyr Val Phe Tyr Gln Leu Arg Cys His Leu Ser Tyr Val Ala Leu
145 150 155 160

Ser Ile Asn Gly Asp Lys Phe Gln Tyr Thr Gly Ala Met Thr Ser Lys
165 170 175

Phe Leu Met Gly Thr Tyr Lys Arg Val Thr Glu Lys Gly Asp Glu His
180 185 190

Val Leu Ser Leu Val Phe Gly Lys Thr Lys Asp Leu Pro Asp Leu Arg
195 200 205

Gly Pro Phe Ser Tyr Pro Ser Leu Thr Ser Ala Gln Ser Gly Asp Tyr
210 215 220

Ser Leu Val Ile Val Thr Thr Phe Val His Tyr Ala Asn Phe His Asn
225 230 235 240

Tyr Phe Val Pro Asn Leu Lys Asp Met Phe Ser Arg Ala Val Thr Met

-continued

```
                245                 250                 255

Thr Ala Ala Ser Tyr Ala Arg Tyr Val Leu Gln Lys Leu Val Leu Leu
            260                 265                 270

Glu Met Lys Gly Gly Cys Arg Glu Pro Glu Leu Asp Thr Glu Thr Leu
        275                 280                 285

Thr Thr Met Phe Glu Val Ser Val Ala Phe Phe Lys Val Gly His Ala
    290                 295                 300

Val Gly Glu Thr Gly Asn Gly Cys Val Asp Leu Arg Trp Leu Ala Lys
305                 310                 315                 320

Ser Phe Phe Glu Leu Thr Val Leu Lys Asp Ile Ile Gly Ile Cys Tyr
                325                 330                 335

Gly Ala Thr Val Lys Gly Met Gln Ser Tyr Gly Leu Glu Arg Leu Ala
            340                 345                 350

Ala Met Leu Met Ala Thr Val Lys Met Glu Glu Leu Gly His Leu Thr
        355                 360                 365

Thr Glu Lys Gln Glu Tyr Ala Leu Arg Leu Ala Thr Val Gly Tyr Pro
    370                 375                 380

Lys Ala Gly Val Tyr Ser Gly Leu Ile Gly Gly Ala Thr Ser Val Leu
385                 390                 395                 400

Leu Ser Ala Tyr Asn Arg His Pro Leu Phe Gln Pro Leu His Thr Val
                405                 410                 415

Met Arg Glu Thr Leu Phe Ile Gly Ser His Val Val Leu Arg Glu Leu
            420                 425                 430

Arg Leu Asn Val Thr Thr Gln Gly Pro Asn Leu Ala Leu Tyr Gln Leu
        435                 440                 445

Leu Ser Thr Ala Leu Cys Ser Ala Leu Glu Ile Gly Glu Val Leu Arg
    450                 455                 460

Gly Leu Ala Leu Gly Thr Glu Ser Gly Leu Phe Ser Pro Cys Tyr Leu
465                 470                 475                 480

Ser Leu Arg Phe Asp Leu Thr Arg Asp Lys Leu Leu Ser Met Ala Pro
                485                 490                 495

Gln Glu Ala Thr Leu Asp Gln Ala Ala Val Ser Asn Ala Val Asp Gly
            500                 505                 510

Phe Leu Gly Arg Leu Ser Leu Glu Arg Glu Asp Arg Asp Ala Trp His
        515                 520                 525

Leu Pro Ala Tyr Lys Cys Val Asp Arg Leu Asp Lys Val Leu Met Ile
    530                 535                 540

Ile Pro Leu Ile Asn Val Thr Phe Ile Ile Ser Ser Asp Arg Glu Val
545                 550                 555                 560

Arg Gly Ser Ala Leu Tyr Glu Ala Ser Thr Thr Tyr Leu Ser Ser Ser
                565                 570                 575

Leu Phe Leu Ser Pro Val Ile Met Asn Lys Cys Ser Gln Gly Ala Val
            580                 585                 590

Ala Gly Glu Pro Arg Gln Ile Pro Lys Ile Gln Asn Phe Thr Arg Thr
        595                 600                 605

Gln Lys Ser Cys Ile Phe Cys Gly Phe Ala Leu Leu Ser Tyr Asp Glu
    610                 615                 620

Lys Glu Gly Leu Glu Thr Thr Thr Tyr Ile Thr Ser Gln Glu Val Gln
625                 630                 635                 640

Asn Ser Ile Leu Ser Ser Asn Tyr Phe Asp Phe Asp Asn Leu His Val
                645                 650                 655

His Tyr Leu Leu Leu Thr Thr Asn Gly Thr Val Met Glu Ile Ala Gly
            660                 665                 670
```

Leu Tyr Glu Glu Arg Ala His Val Val Leu Ala Ile Ile Leu Tyr Phe
        675                 680                 685

Ile Ala Phe Ala Leu Gly Ile Phe Leu Val His Lys Ile Val Met Phe
    690                 695                 700

Phe Leu
705

<210> SEQ ID NO 7
<211> LENGTH: 411
<212> TYPE: RNA
<213> ORGANISM: Artificial Sequence
<220> FEATURE:
<223> OTHER INFORMATION: Synthetic

<400> SEQUENCE: 7
augagagccg ugggcguguu ccuggccauc ugccugguga ccaucuucgu gcugcccacc 60
uggggcaacu gggccuaccc cugcugccac gugacccagc ugagagccca gcaccugcug 120
gcccuggaga acaucagcga caucuaccug gugagcaacc agaccugcga cggcuucagc 180
cuggccagcc ugaacagccc caagaacggc agcaaccagc uggugaucag cagaugcgcc 240
aacggccuga acguggugag cuucuucauc agcauccuga agagaagcag cagcgcccug 300
accggccacc ugagagagcu gcugaccacc cuggagaccc uguacggcag cuucagcgug 360
gaggaccugu ucggcgccaa ccugaacaga uacgccuggc acagaggcgg c 411

<210> SEQ ID NO 8
<211> LENGTH: 137
<212> TYPE: PRT
<213> ORGANISM: Artificial Sequence
<220> FEATURE:
<223> OTHER INFORMATION: Synthetic

<400> SEQUENCE: 8

Met Arg Ala Val Gly Val Phe Leu Ala Ile Cys Leu Val Thr Ile Phe
1               5                   10                  15

Val Leu Pro Thr Trp Gly Asn Trp Ala Tyr Pro Cys Cys His Val Thr
            20                  25                  30

Gln Leu Arg Ala Gln His Leu Leu Ala Leu Glu Asn Ile Ser Asp Ile
        35                  40                  45

Tyr Leu Val Ser Asn Gln Thr Cys Asp Gly Phe Ser Leu Ala Ser Leu
    50                  55                  60

Asn Ser Pro Lys Asn Gly Ser Asn Gln Leu Val Ile Ser Arg Cys Ala
65                  70                  75                  80

Asn Gly Leu Asn Val Val Ser Phe Phe Ile Ser Ile Leu Lys Arg Ser
                85                  90                  95

Ser Ser Ala Leu Thr Gly His Leu Arg Glu Leu Leu Thr Thr Leu Glu
            100                 105                 110

Thr Leu Tyr Gly Ser Phe Ser Val Glu Asp Leu Phe Gly Ala Asn Leu
        115                 120                 125

Asn Arg Tyr Ala Trp His Arg Gly Gly
    130                 135

<210> SEQ ID NO 9
<211> LENGTH: 612
<212> TYPE: RNA
<213> ORGANISM: Artificial Sequence
<220> FEATURE:
<223> OTHER INFORMATION: Synthetic -continued

<400> SEQUENCE: 9
augacccggc ggcggguguu aagcguggug gugcucuuag ccgccuuagc cugccggcuu 60
ggcgccauca ccugggugcc caagcccaac guggaggugu ggcccgugga cccgccaccu 120
cccgugaacu ucaacaagac cgccgagcag gaguacggcg acaaggaggu gaagcugccc 180
cacuggacgc cgacccugca caccuuccag gugccccaga acuacaccaa ggccaacugc 240
accuacugca acaccagaga guacaccuuc agcuacaagg gcugcugcuu cuacuucacc 300
aagaagaagc acaccuggaa cggcugcuuc caggccugcg ccgagcugua ccccugcacc 360
uacuucuacg gccccacccc agacauccug cccgugguga ccagaaaccu gaacgccauc 420
gagagccugu gggugggcgu guacagagug ggcgagggca acuggaccag ccuggacggc 480
ggcaccuuca aggugu acca gaucuucggc agccacugca ccuacgugag caaguucagc 540
accgugcccg ugagccacca cgagugcagc uuccugaagc ccugccugug cgugagccag 600
agaagcaaca gc 612

<210> SEQ ID NO 10
<211> LENGTH: 204
<212> TYPE: PRT
<213> ORGANISM: Artificial Sequence
<220> FEATURE:
<223> OTHER INFORMATION: Synthetic

<400> SEQUENCE: 10

Met Thr Arg Arg Arg Val Leu Ser Val Val Val Leu Leu Ala Ala Leu
1 5 10 15

Ala Cys Arg Leu Gly Ala Ile Thr Trp Val Pro Lys Pro Asn Val Glu
20 25 30

Val Trp Pro Val Asp Pro Pro Pro Pro Val Asn Phe Asn Lys Thr Ala
35 40 45

Glu Gln Glu Tyr Gly Asp Lys Glu Val Lys Leu Pro His Trp Thr Pro
50 55 60

Thr Leu His Thr Phe Gln Val Pro Gln Asn Tyr Thr Lys Ala Asn Cys
65 70 75 80

Thr Tyr Cys Asn Thr Arg Glu Tyr Thr Phe Ser Tyr Lys Gly Cys Cys
85 90 95

Phe Tyr Phe Thr Lys Lys Lys His Thr Trp Asn Gly Cys Phe Gln Ala
100 105 110

Cys Ala Glu Leu Tyr Pro Cys Thr Tyr Phe Tyr Gly Pro Thr Pro Asp
115 120 125

Ile Leu Pro Val Val Thr Arg Asn Leu Asn Ala Ile Glu Ser Leu Trp
130 135 140

Val Gly Val Tyr Arg Val Gly Glu Gly Asn Trp Thr Ser Leu Asp Gly
145 150 155 160

Gly Thr Phe Lys Val Tyr Gln Ile Phe Gly Ser His Cys Thr Tyr Val
165 170 175

Ser Lys Phe Ser Thr Val Pro Val Ser His His Glu Cys Ser Phe Leu
180 185 190

Lys Pro Cys Leu Cys Val Ser Gln Arg Ser Asn Ser
195 200

<210> SEQ ID NO 11
<211> LENGTH: 2571
<212> TYPE: RNA
<213> ORGANISM: Artificial Sequence
<220> FEATURE:

<223> OTHER INFORMATION: Synthetic

<400> SEQUENCE: 11
augacccggc ggcggguguu aagcguggug gugcucuuag ccgccuuagc cugccggcuu 60
ggcgcccaga cuccggagca gcccgcuccu cccgccacca ccguccagcc caccgccacc 120
cgccagcaga ccuccuuccc cuuccgcguc ugcgagcucu ccucccacgg cgaccucuuc 180
cgcuucuccu ccgacaucca gugccccucc uucggcaccc gcgagaacca caccgagggc 240
cuccucaugg ucuucaagga caacaucauc cccuacuccu ucaagguccg cuccuacacc 300
aagaucguca ccaacauccu caucuacaac ggcugguacg ccgacucugu gacuaaucgc 360
cacgaggaga aguucuccgu cgacuccuac gagacugacc agauggacac caucuaccag 420
ugcuacaacg ccgucaagau gaccaaggac ggccucaccc gcgucuacgu cgaccgcgac 480
ggcgucaaca ucaccgucaa ccucaagccu acaggcggcc ucgccaacgg cguccgccgc 540
uacgccuccc agaccgagcu cuacgacgcc ccuggcuggc ucaucuggac cuaccgcacc 600
aggaccacug ucaauugccu caucaccgac augauggcca aguccaacuc cccuuucgac 660
uucuucguga ccaccacagg ccagaccguc gagaugucgc cauucuauga cggcaagaac 720
aaggagacuu uccacgagag agcggacucu uuccaugucc gcaccaacua caagauuguc 780
gacuacgaca accgcggcac caauccacag ggcgagcgcc gcgccuuccu cgacaagggc 840
accuacaccc ucuccuggaa gcucgagaac cgcaccgccu acuguccucu ccagcacugg 900
cagaccuucg auuccaccau cgccaccgag acuggcaagu ccauccauuu cgucaccgac 960
gaaggaacau cuucauucgu cacaaauaca accgugggca ucgagcuccc cgacgccuuc 1020
aagugcaucg aggagcaggu caacaagacc augcacgaga aguacgaggc cguccaggac 1080
cgguauacaa agggccagga ggccaucacc uacuucauca ccagcggagg ucugcuucuc 1140
gccuggcuuc cacucacacc ucgcucccug gccacaguga agaaccucac ugaguugacc 1200
accccaacaa guuccccacc uaguaguccu agcccuccug cuccuuccgc cgcccgcggc 1260
uccacgccug ccgccguccu gcggagacgg agaagggacg ccggcaacgc uaccacuccu 1320
gugccgccga cagccccugg aaagucccua gguacccuca acaacccagc gacaguucag 1380
auccaguucg ccuacgacuc ucucaggcgc cagaucaacc gcaugcuugg ugaccuugcc 1440
cgcgccuggu gccucgagca gaagcgccag aacauggugc uucgugaacu aacaaagauu 1500
aauccuacua cagugauguc cuccaucuac ggcaaggccg ucgccgccaa gcgccucggc 1560
gacgucaucu ccgucuccca gugcguccca gugaaccagg cuaccgugac ccucaggaag 1620
uccaugagag ugccaggcuc cgagacaaug ugcuacuccc gcccacucgu cuccuucucc 1680
uucaucaacg acacaaagac cuacgagggc caguuaggca cugacaacga gaucuucuug 1740
acuaagaaga ugacugaggu augccaggca acuucucaau acuacuucca gucuggaaau 1800
gagauccacg uauauaacga cuaccaccac uucaagacua uugaacucga cggaauugcc 1860
acccuccaaa cauucaucuc acugaauacc ucccucaucg agaacaucga cuucgccucc 1920
cucgagcugu auagcagaga cgagcagcgc gccuccaacg ucuucgaccu cgagggcauc 1980
uuccgcgagu acaacuucca ggcacagaac auagccggcc uccguaagga ucuggacaau 2040
gccgugucca acggccgcaa ccaguucguc gacgguuugg gugaacucau ggacucucug 2100
ggcuccgucg gccaguccau aacuaacuua gucucuacgg ugggaggccu auucagcagc 2160
cuggugagcg gcuucaucuc uuucuucaag aaccccuucg gcggcaugcu cauccucguc 2220
cucgucgccg gcgucgucau acuggugauc ucacucacaa ggaggacgcg ccaaaugucc 2280
cagcagccag ugcagaugcu cuacccaggc auagacgagc ucgcucagca gcacgcgucg 2340
ggugagggac caggcaucaa uccuaucucc aagacugagc ugcaagccau uaugcucgcc 2400
cuccacgagc agaaccagga acagaagcgg gccgcccagc gagcugccgg ccccuccguc 2460
gccaguaggg cacuacaagc cgcccgggac cgcuucccag gccugagaag gaggagauac 2520
cacgacccag agacagccgc ugcccuccuu ggcgaagcag aaaccgaguu c 2571

<210> SEQ ID NO 12
<211> LENGTH: 857
<212> TYPE: PRT
<213> ORGANISM: Artificial Sequence
<220> FEATURE:
<223> OTHER INFORMATION: Synthetic

<400> SEQUENCE: 12

Met Thr Arg Arg Arg Val Leu Ser Val Val Val Leu Leu Ala Ala Leu
1 5 10 15

Ala Cys Arg Leu Gly Ala Gln Thr Pro Glu Gln Pro Ala Pro Pro Ala
20 25 30

Thr Thr Val Gln Pro Thr Ala Thr Arg Gln Gln Thr Ser Phe Pro Phe
35 40 45

Arg Val Cys Glu Leu Ser Ser His Gly Asp Leu Phe Arg Phe Ser Ser
50 55 60

Asp Ile Gln Cys Pro Ser Phe Gly Thr Arg Glu Asn His Thr Glu Gly
65 70 75 80

Leu Leu Met Val Phe Lys Asp Asn Ile Ile Pro Tyr Ser Phe Lys Val
85 90 95

Arg Ser Tyr Thr Lys Ile Val Thr Asn Ile Leu Ile Tyr Asn Gly Trp
100 105 110

Tyr Ala Asp Ser Val Thr Asn Arg His Glu Glu Lys Phe Ser Val Asp
115 120 125

Ser Tyr Glu Thr Asp Gln Met Asp Thr Ile Tyr Gln Cys Tyr Asn Ala
130 135 140

Val Lys Met Thr Lys Asp Gly Leu Thr Arg Val Tyr Val Asp Arg Asp
145 150 155 160

Gly Val Asn Ile Thr Val Asn Leu Lys Pro Thr Gly Gly Leu Ala Asn
165 170 175

Gly Val Arg Arg Tyr Ala Ser Gln Thr Glu Leu Tyr Asp Ala Pro Gly
180 185 190

Trp Leu Ile Trp Thr Tyr Arg Thr Arg Thr Thr Val Asn Cys Leu Ile
195 200 205

Thr Asp Met Met Ala Lys Ser Asn Ser Pro Phe Asp Phe Phe Val Thr
210 215 220

Thr Thr Gly Gln Thr Val Glu Met Ser Pro Phe Tyr Asp Gly Lys Asn
225 230 235 240

Lys Glu Thr Phe His Glu Arg Ala Asp Ser Phe His Val Arg Thr Asn
245 250 255

Tyr Lys Ile Val Asp Tyr Asp Asn Arg Gly Thr Asn Pro Gln Gly Glu
260 265 270

Arg Arg Ala Phe Leu Asp Lys Gly Thr Tyr Thr Leu Ser Trp Lys Leu
275 280 285

Glu Asn Arg Thr Ala Tyr Cys Pro Leu Gln His Trp Gln Thr Phe Asp
290 295 300

Ser Thr Ile Ala Thr Glu Thr Gly Lys Ser Ile His Phe Val Thr Asp

-continued

```
305                 310                 315                 320

Glu Gly Thr Ser Ser Phe Val Thr Asn Thr Thr Val Gly Ile Glu Leu
                325                 330                 335

Pro Asp Ala Phe Lys Cys Ile Glu Glu Gln Val Asn Lys Thr Met His
            340                 345                 350

Glu Lys Tyr Glu Ala Val Gln Asp Arg Tyr Thr Lys Gly Gln Glu Ala
        355                 360                 365

Ile Thr Tyr Phe Ile Thr Ser Gly Gly Leu Leu Leu Ala Trp Leu Pro
    370                 375                 380

Leu Thr Pro Arg Ser Leu Ala Thr Val Lys Asn Leu Thr Glu Leu Thr
385                 390                 395                 400

Thr Pro Thr Ser Ser Pro Pro Ser Ser Pro Ser Pro Pro Ala Pro Ser
                405                 410                 415

Ala Ala Arg Gly Ser Thr Pro Ala Ala Val Leu Arg Arg Arg Arg Arg
            420                 425                 430

Asp Ala Gly Asn Ala Thr Thr Pro Val Pro Pro Thr Ala Pro Gly Lys
        435                 440                 445

Ser Leu Gly Thr Leu Asn Asn Pro Ala Thr Val Gln Ile Gln Phe Ala
    450                 455                 460

Tyr Asp Ser Leu Arg Arg Gln Ile Asn Arg Met Leu Gly Asp Leu Ala
465                 470                 475                 480

Arg Ala Trp Cys Leu Glu Gln Lys Arg Gln Asn Met Val Leu Arg Glu
                485                 490                 495

Leu Thr Lys Ile Asn Pro Thr Thr Val Met Ser Ser Ile Tyr Gly Lys
            500                 505                 510

Ala Val Ala Ala Lys Arg Leu Gly Asp Val Ile Ser Val Ser Gln Cys
        515                 520                 525

Val Pro Val Asn Gln Ala Thr Val Thr Leu Arg Lys Ser Met Arg Val
    530                 535                 540

Pro Gly Ser Glu Thr Met Cys Tyr Ser Arg Pro Leu Val Ser Phe Ser
545                 550                 555                 560

Phe Ile Asn Asp Thr Lys Thr Tyr Glu Gly Gln Leu Gly Thr Asp Asn
                565                 570                 575

Glu Ile Phe Leu Thr Lys Lys Met Thr Glu Val Cys Gln Ala Thr Ser
            580                 585                 590

Gln Tyr Tyr Phe Gln Ser Gly Asn Glu Ile His Val Tyr Asn Asp Tyr
        595                 600                 605

His His Phe Lys Thr Ile Glu Leu Asp Gly Ile Ala Thr Leu Gln Thr
    610                 615                 620

Phe Ile Ser Leu Asn Thr Ser Leu Ile Glu Asn Ile Asp Phe Ala Ser
625                 630                 635                 640

Leu Glu Leu Tyr Ser Arg Asp Glu Gln Arg Ala Ser Asn Val Phe Asp
                645                 650                 655

Leu Glu Gly Ile Phe Arg Glu Tyr Asn Phe Gln Ala Gln Asn Ile Ala
            660                 665                 670

Gly Leu Arg Lys Asp Leu Asp Asn Ala Val Ser Asn Gly Arg Asn Gln
        675                 680                 685

Phe Val Asp Gly Leu Gly Glu Leu Met Asp Ser Leu Gly Ser Val Gly
    690                 695                 700

Gln Ser Ile Thr Asn Leu Val Ser Thr Val Gly Gly Leu Phe Ser Ser
705                 710                 715                 720

Leu Val Ser Gly Phe Ile Ser Phe Phe Lys Asn Pro Phe Gly Gly Met
                725                 730                 735
```

```
Leu Ile Leu Val Leu Val Ala Gly Val Val Ile Leu Val Ile Ser Leu
            740                 745                 750

Thr Arg Arg Thr Arg Gln Met Ser Gln Gln Pro Val Gln Met Leu Tyr
        755                 760                 765

Pro Gly Ile Asp Glu Leu Ala Gln Gln His Ala Ser Gly Glu Gly Pro
    770                 775                 780

Gly Ile Asn Pro Ile Ser Lys Thr Glu Leu Gln Ala Ile Met Leu Ala
785                 790                 795                 800

Leu His Glu Gln Asn Gln Glu Gln Lys Arg Ala Ala Gln Arg Ala Ala
                805                 810                 815

Gly Pro Ser Val Ala Ser Arg Ala Leu Gln Ala Ala Arg Asp Arg Phe
            820                 825                 830

Pro Gly Leu Arg Arg Arg Arg Tyr His Asp Pro Glu Thr Ala Ala Ala
        835                 840                 845

Leu Leu Gly Glu Ala Glu Thr Glu Phe
    850                 855


<210> SEQ ID NO 13
<211> LENGTH: 669
<212> TYPE: RNA
<213> ORGANISM: Artificial Sequence
<220> FEATURE:
<223> OTHER INFORMATION: Synthetic

<400> SEQUENCE: 13

auggugagcu ucaagcaggu gagagugccc cuguucaccg ccaucgcccu ggugaucgug      60

cugcugcugg ccuacuuccu gccacccaga gugagaggcg gcggcagagu ggccgccgcc     120

gccaucaccu gggugcccaa gcccaacgug gagguguggc ccguggaccc gccaccuccc     180

gugaacuuca acaagaccgc cgagcaggag uacggcgaca aggaggugaa gcugccccac     240

uggacgccga cccugcacac cuuccaggug ccccagaacu acaccaaggc caacugcacc     300

uacugcaaca ccagagagua caccuucagc uacaagggcu gcugcuucua cuucaccaag     360

aagaagcaca ccuggaacgg cugcuuccag gccugcgccg agcuguaccc cugcaccuac     420

uucuacggcc ccaccccaga cauccugccc guggugacca gaaaccugaa cgccaucgag     480

agccuguggg ugggcgugua cagagugggc gagggcaacu ggaccagccu ggacggcggc     540

accuucaagg uguaccagau cuucggcagc cacugcaccu acgugagcaa guucagcacc     600

gugcccguga gccaccacga gugcagcuuc cugaagcccu gccugugcgu gagccagaga     660

agcaacagc                                                             669


<210> SEQ ID NO 14
<211> LENGTH: 223
<212> TYPE: PRT
<213> ORGANISM: Artificial Sequence
<220> FEATURE:
<223> OTHER INFORMATION: Synthetic

<400> SEQUENCE: 14

Met Val Ser Phe Lys Gln Val Arg Val Pro Leu Phe Thr Ala Ile Ala
1               5                   10                  15

Leu Val Ile Val Leu Leu Leu Ala Tyr Phe Leu Pro Pro Arg Val Arg
            20                  25                  30

Gly Gly Gly Arg Val Ala Ala Ala Ala Ile Thr Trp Val Pro Lys Pro
        35                  40                  45

Asn Val Glu Val Trp Pro Val Asp Pro Pro Pro Pro Val Asn Phe Asn
```

```
    50                  55                  60

Lys Thr Ala Glu Gln Glu Tyr Gly Asp Lys Glu Val Lys Leu Pro His
65                  70                  75                  80

Trp Thr Pro Thr Leu His Thr Phe Gln Val Pro Gln Asn Tyr Thr Lys
                85                  90                  95

Ala Asn Cys Thr Tyr Cys Asn Thr Arg Glu Tyr Thr Phe Ser Tyr Lys
            100                 105                 110

Gly Cys Cys Phe Tyr Phe Thr Lys Lys Lys His Thr Trp Asn Gly Cys
        115                 120                 125

Phe Gln Ala Cys Ala Glu Leu Tyr Pro Cys Thr Tyr Phe Tyr Gly Pro
    130                 135                 140

Thr Pro Asp Ile Leu Pro Val Val Thr Arg Asn Leu Asn Ala Ile Glu
145                 150                 155                 160

Ser Leu Trp Val Gly Val Tyr Arg Val Gly Glu Gly Asn Trp Thr Ser
                165                 170                 175

Leu Asp Gly Gly Thr Phe Lys Val Tyr Gln Ile Phe Gly Ser His Cys
            180                 185                 190

Thr Tyr Val Ser Lys Phe Ser Thr Val Pro Val Ser His His Glu Cys
        195                 200                 205

Ser Phe Leu Lys Pro Cys Leu Cys Val Ser Gln Arg Ser Asn Ser
    210                 215                 220


<210> SEQ ID NO 15
<211> LENGTH: 2595
<212> TYPE: RNA
<213> ORGANISM: Artificial Sequence
<220> FEATURE:
<223> OTHER INFORMATION: Synthetic

<400> SEQUENCE: 15

auggaggcag cacugcuggu cugccaguau acaauccagu cgcucauuca ucugacaggc      60

gaggaccccg gcuucuuuaa cguggaaauc ccagaguucc cuuucuaucc aaccuguaac     120

guuugcacug cugacgugaa cgugacaauc aauuucgacg ugggaggaaa gaagcaucag     180

cuugaucugg auuucggcca acugacgcca cacaccaaag cgguguacca accaaggggu     240

gcauuuggag ggagcgagaa ugcuacaaau cuguucuuac uggaacugcu uggugcagga     300

gagcuggcac uaaccaugcg aagcaagaag cuccccauca acguuaccac cggggaagaa     360

cagcaaguca gccuugaauc cguggaugug uacuuucagg auguuuucgg caccaugugg     420

ugucaccacg cugagaugca gaaucccgug uaucucauac ccgagacugu acccuacauc     480

aagugggaua auugcaauuc aacuaauauu acggcugugg ugagggccca gggcuuggac     540

gugacucugc ccuuaucucu accuacuucu gcccaagacu ccaauuucuc ugucaagacc     600

gagaugcucg ggaaugagau cgauaucgag ugcaucaugg aggacgguga gauaagccag     660

guucugcccg gcgacaacaa guucaauauc acuuguucug gcuacgaguc ccaugugccu     720

aguggugca uacucacaag uacuucuccc guagccacgc ccauucccgg aaccggauac     780

gccuacaguc ugcgucugac cccacggccu guguccagau uccuggguaa caauaguauc     840

uuauacgugu uuuauagcgg aaacggcccu aaagcguccg gaggggacua uuguauucag     900

aguaauaucg uuuucucuga ugagauuccu gccagucagg acaugccgac aaacacaacu     960

gauauuaccu acgugggcga caaugccacg uauucagugc ccauggucac gagcgaggac    1020

gccaauucac caaauguuac uguaacagcu uucugggccu ggccaaauaa cacugagacu    1080

gacuucaaau guaaguggac uuugaccucu ggaacuccgu cgguugcga gaauaucagc    1140
```

```
ggggccuuug cuuccaacag gacuuucgac aucacugucu cagggcuggg gacagcaccg   1200

aagacauuaa ucauaacacg gaccgccacc aacgccacga cuacaaccca uaaggugauc   1260

uuuuccaagg caccugaguc caccacuacc uccccgacuc uuaacacuac gggcuucgcu   1320

gaucccaaca ccacuacggg guugccuagc ucgacacaug ugccgacgaa ccugacugcc   1380

ccugcaucga ccgggcccac aguuucgacc gccgauguga caucaccaac gcccgcaggu   1440

acaaccucag gcgccagccc agugaccccu uccccaagcc ccugggauaa uggaacggag   1500

uccaaggcuc cugauaugac uuccucuacc agccccguga cuacacccac ucccaacgca   1560

acuagcccaa ccccagcugu gacgacgccc accccgaacg cgacaucucc cacaccugcu   1620

gugacaaccc caaccccuaa cgccacuagc ccuacccuag guaagaccag uccgacuagc   1680

gccguuacaa ccccuacccc uaacgcaacc ggcccgaccg ugggcgagac uuccccgcaa   1740

gccaaugcga caaaucacac auugggcggg accucuccua caccagucgu uacaucucag   1800

ccuaagaacg cuaccuccgc ugucacuacc ggacagcaca acaucaccag cucaagcacg   1860

aguuccauga gcuugcggcc gagcucaaau cccgagaccc uaucaccauc cacaucagac   1920

aacaguacuu cacacaugcc acucuugacg agcgcucacc ccaccggcgg cgagaacauc   1980

acccagguga cuccggcguc uauuuccacc caccacguca gcacgucguc ucccgcaccg   2040

agaccaggga cgacuucuca ggccaguggg ccuggcaacu ccucuacaag cacaaagcca   2100

ggcgaaguua acgugacaaa gggaacgccu ccccagaacg caaccagucc ucaggcgccc   2160

agcgggcaga agacugcggu gccaacugug accagcaccg guggcaaggc caacucaaca   2220

acuggaggca agcauacgac ggggcacggc gcccggaccu ccacugaacc cacgaccgau   2280

uacggaggug acagcacaac accgcggcca cgauauaaug ccaccacuua ucugccacca   2340

uccacaagcu ccaagcugcg gccacggugg accuucacaa gcccacccgu gacgacugcc   2400

caagcgacgg ugccagugcc accuacaagc cagccacgcu ucuccaaccu uaguaugcuc   2460

guucuccagu gggccagccu ugcuguucug acccuccucc ugcugcucgu gauggccgau   2520

ugcgccuuua ggagaaaccu cagcacuagc cacacguaca ccacgccgcc cuacgaugac   2580

gccgagacuu acguc                                                    2595
```

<210> SEQ ID NO 16
<211> LENGTH: 865
<212> TYPE: PRT
<213> ORGANISM: Artificial Sequence
<220> FEATURE:
<223> OTHER INFORMATION: Synthetic

<400> SEQUENCE: 16

```
Met Glu Ala Ala Leu Leu Val Cys Gln Tyr Thr Ile Gln Ser Leu Ile
1               5                   10                  15

His Leu Thr Gly Glu Asp Pro Gly Phe Phe Asn Val Glu Ile Pro Glu
            20                  25                  30

Phe Pro Phe Tyr Pro Thr Cys Asn Val Cys Thr Ala Asp Val Asn Val
        35                  40                  45

Thr Ile Asn Phe Asp Val Gly Gly Lys Lys His Gln Leu Asp Leu Asp
    50                  55                  60

Phe Gly Gln Leu Thr Pro His Thr Lys Ala Val Tyr Gln Pro Arg Gly
65                  70                  75                  80

Ala Phe Gly Gly Ser Glu Asn Ala Thr Asn Leu Phe Leu Leu Glu Leu
                85                  90                  95
```

-continued

```
Leu Gly Ala Gly Glu Leu Ala Leu Thr Met Arg Ser Lys Lys Leu Pro
            100                 105                 110

Ile Asn Val Thr Thr Gly Glu Glu Gln Gln Val Ser Leu Glu Ser Val
        115                 120                 125

Asp Val Tyr Phe Gln Asp Val Phe Gly Thr Met Trp Cys His His Ala
    130                 135                 140

Glu Met Gln Asn Pro Val Tyr Leu Ile Pro Glu Thr Val Pro Tyr Ile
145                 150                 155                 160

Lys Trp Asp Asn Cys Asn Ser Thr Asn Ile Thr Ala Val Val Arg Ala
                165                 170                 175

Gln Gly Leu Asp Val Thr Leu Pro Leu Ser Leu Pro Thr Ser Ala Gln
            180                 185                 190

Asp Ser Asn Phe Ser Val Lys Thr Glu Met Leu Gly Asn Glu Ile Asp
        195                 200                 205

Ile Glu Cys Ile Met Glu Asp Gly Glu Ile Ser Gln Val Leu Pro Gly
    210                 215                 220

Asp Asn Lys Phe Asn Ile Thr Cys Ser Gly Tyr Glu Ser His Val Pro
225                 230                 235                 240

Ser Gly Gly Ile Leu Thr Ser Thr Ser Pro Val Ala Thr Pro Ile Pro
                245                 250                 255

Gly Thr Gly Tyr Ala Tyr Ser Leu Arg Leu Thr Pro Arg Pro Val Ser
            260                 265                 270

Arg Phe Leu Gly Asn Asn Ser Ile Leu Tyr Val Phe Tyr Ser Gly Asn
        275                 280                 285

Gly Pro Lys Ala Ser Gly Gly Asp Tyr Cys Ile Gln Ser Asn Ile Val
    290                 295                 300

Phe Ser Asp Glu Ile Pro Ala Ser Gln Asp Met Pro Thr Asn Thr Thr
305                 310                 315                 320

Asp Ile Thr Tyr Val Gly Asp Asn Ala Thr Tyr Ser Val Pro Met Val
                325                 330                 335

Thr Ser Glu Asp Ala Asn Ser Pro Asn Val Thr Val Thr Ala Phe Trp
            340                 345                 350

Ala Trp Pro Asn Asn Thr Glu Thr Asp Phe Lys Cys Lys Trp Thr Leu
        355                 360                 365

Thr Ser Gly Thr Pro Ser Gly Cys Glu Asn Ile Ser Gly Ala Phe Ala
    370                 375                 380

Ser Asn Arg Thr Phe Asp Ile Thr Val Ser Gly Leu Gly Thr Ala Pro
385                 390                 395                 400

Lys Thr Leu Ile Ile Thr Arg Thr Ala Thr Asn Ala Thr Thr Thr Thr
                405                 410                 415

His Lys Val Ile Phe Ser Lys Ala Pro Glu Ser Thr Thr Thr Ser Pro
            420                 425                 430

Thr Leu Asn Thr Thr Gly Phe Ala Asp Pro Asn Thr Thr Thr Gly Leu
        435                 440                 445

Pro Ser Ser Thr His Val Pro Thr Asn Leu Thr Ala Pro Ala Ser Thr
    450                 455                 460

Gly Pro Thr Val Ser Thr Ala Asp Val Thr Ser Pro Thr Pro Ala Gly
465                 470                 475                 480

Thr Thr Ser Gly Ala Ser Pro Val Thr Pro Ser Pro Ser Pro Trp Asp
                485                 490                 495

Asn Gly Thr Glu Ser Lys Ala Pro Asp Met Thr Ser Ser Thr Ser Pro
            500                 505                 510

Val Thr Thr Pro Thr Pro Asn Ala Thr Ser Pro Thr Pro Ala Val Thr
```

```
        515                 520                 525

Thr Pro Thr Pro Asn Ala Thr Ser Pro Thr Pro Ala Val Thr Thr Pro
    530                 535                 540

Thr Pro Asn Ala Thr Ser Pro Thr Leu Gly Lys Thr Ser Pro Thr Ser
545                 550                 555                 560

Ala Val Thr Thr Pro Thr Pro Asn Ala Thr Gly Pro Thr Val Gly Glu
                565                 570                 575

Thr Ser Pro Gln Ala Asn Ala Thr Asn His Thr Leu Gly Gly Thr Ser
            580                 585                 590

Pro Thr Pro Val Val Thr Ser Gln Pro Lys Asn Ala Thr Ser Ala Val
        595                 600                 605

Thr Thr Gly Gln His Asn Ile Thr Ser Ser Ser Thr Ser Ser Met Ser
    610                 615                 620

Leu Arg Pro Ser Ser Asn Pro Glu Thr Leu Ser Pro Ser Thr Ser Asp
625                 630                 635                 640

Asn Ser Thr Ser His Met Pro Leu Leu Thr Ser Ala His Pro Thr Gly
                645                 650                 655

Gly Glu Asn Ile Thr Gln Val Thr Pro Ala Ser Ile Ser Thr His His
            660                 665                 670

Val Ser Thr Ser Ser Pro Ala Pro Arg Pro Gly Thr Thr Ser Gln Ala
        675                 680                 685

Ser Gly Pro Gly Asn Ser Ser Thr Ser Thr Lys Pro Gly Glu Val Asn
    690                 695                 700

Val Thr Lys Gly Thr Pro Pro Gln Asn Ala Thr Ser Pro Gln Ala Pro
705                 710                 715                 720

Ser Gly Gln Lys Thr Ala Val Pro Thr Val Thr Ser Thr Gly Gly Lys
                725                 730                 735

Ala Asn Ser Thr Thr Gly Gly Lys His Thr Thr Gly His Gly Ala Arg
            740                 745                 750

Thr Ser Thr Glu Pro Thr Thr Asp Tyr Gly Gly Asp Ser Thr Thr Pro
        755                 760                 765

Arg Pro Arg Tyr Asn Ala Thr Thr Tyr Leu Pro Pro Ser Thr Ser Ser
    770                 775                 780

Lys Leu Arg Pro Arg Trp Thr Phe Thr Ser Pro Pro Val Thr Thr Ala
785                 790                 795                 800

Gln Ala Thr Val Pro Val Pro Pro Thr Ser Gln Pro Arg Phe Ser Asn
                805                 810                 815

Leu Ser Met Leu Val Leu Gln Trp Ala Ser Leu Ala Val Leu Thr Leu
            820                 825                 830

Leu Leu Leu Leu Val Met Ala Asp Cys Ala Phe Arg Arg Asn Leu Ser
        835                 840                 845

Thr Ser His Thr Tyr Thr Thr Pro Pro Tyr Asp Asp Ala Glu Thr Tyr
    850                 855                 860

Val
865


<210> SEQ ID NO 17
<211> LENGTH: 2150
<212> TYPE: RNA
<213> ORGANISM: Artificial Sequence
<220> FEATURE:
<223> OTHER INFORMATION: Synthetic

<400> SEQUENCE: 17

gggaaauaag agagaaaaga agaguaagaa gaaauauaag accccggcgc cgccaccaug     60
```

-continued gaggcagcac ugcuggucug ccaguauaca auccagucgc ucauucaucu gacaggcgag 120
gaccccggcu ucuuuaacgu ggaaauccca gaguucccuu ucuauccaac cuguaacguu 180
ugcacugcug acgugaacgu gacaaucaau uucgacgugg gaggaaagaa gcaucagcuu 240
gaucuggauu ucggccaacu gacgccacac accaaagcgg uguaccaacc aaggggugca 300
uuuggaggga gcgagaaugc uacaaaccug uucuuacugg aacugcuugg ugcaggagag 360
cuggcacuaa ccaugcgaag caagaagcuc cccaucaacg uuaccaccgg ggaagaacag 420
caagucagcc uugaauccgu ggauguguac uuucaggaug uuuucggcac cauguggugu 480
caccacgcug agaugcagaa ucccguguau cucauacccg agacuguacc cuacaucaag 540
ugggauaauu gcaauucaac uaauauuacg gcugugguga gggcccaggg cuuggacgug 600
acucugcccu uaucucuacc uacuucugcc caagacucca auuucucugu caagaccgag 660
augcucggga augagaucga uaucgagugc aucauggagg acggugagau aagccagguu 720
cugcccggcg acaacaaguu caauaucacu uguucuggcu acgaguccca ugugccuagu 780
gguggcauac ucacaaguac uucucccgua gccacgccca uucccggaac cggauacgcc 840
uacagucugc gucugacccc acggccugug uccagauucc uggguaacaa uaguaucuua 900
uacguguuuu auagcggaaa cggcccuaaa gcguccggag gggacuauug uauucagagu 960
aauaucguuu ucucugauga gauuccugcc agucaggaca ugccgacaaa cacaacugau 1020
auuaccuacg ugggcgacaa ugccacguau ucagugccca uggucacgag cgaggacgcc 1080
aauucaccaa auguuacugu aacagcuuuc ugggccuggc caaauaacac ugagacugac 1140
uucaaaugua aguggacuuu gaccucugga acuccgucgg guugcgagaa uaucagcggg 1200
gccuuugcuu ccaacaggac uuucgacauc acugucucag ggcuggggac agcaccgaag 1260
acauuaauca uaacacggac cgccaccaac gccacgacua caacccauaa ggugaucuuu 1320
uccaaggcac cugaguccac cacuaccucc ccgacucuua acacuacggg cuucgcugau 1380
cccaacacca cuacgggguu gccuagcucg acacaugugc cgacgaaccu gacugccccu 1440
gcaucgaccg ggcccacagu uucgaccgcc gaugugacau caccaacgcc cgcagguaca 1500
accucaggcg ccagcccagu gaccccuucc ccaagccccu gggauaaugg aacggagucc 1560
acgccucccc agaacgcaac caguccucag gcgcccagcg ggcagaagac ugcggugcca 1620
acugugacca gcaccggugg caaggccaac ucaacaacug gaggcaagca uacgacgggg 1680
cacggcgccc ggaccuccac ugaacccacg accgauuacg gaggugacag cacaacaccg 1740
cggccacgau auaaugccac cacuuaucug ccaccaucca caagcuccaa gcugcggcca 1800
cgguggaccu ucacaagccc acccgugacg acugcccaag cgacggugcc agugccaccu 1860
acaagccagc cacgcuucuc caaccuuagu augcucguuc uccagugggc cagccuugcu 1920
guucugaccc uccuccugcu gcucgugaug gccgauugcg ccuuuaggag aaaccucagc 1980
acuagccaca cguacaccac gccgcccuac gaugacgccg agacuuacgu cugauaauag 2040
gcuggagccu cgguggccua gcuucuugcc ccuugggccu ccccccagcc ccuccucccc 2100
uuccugcacc cguacccccg uggucuuuga auaaagucug agugggcggc 2150

<210> SEQ ID NO 18
<211> LENGTH: 2294
<212> TYPE: RNA
<213> ORGANISM: Artificial Sequence
<220> FEATURE:
<223> OTHER INFORMATION: Synthetic

<400> SEQUENCE: 18

```
gggaaauaag agagaaaaga agaguaagaa gaaauauaag accccggcgc cgccaccaug      60
caguuguugu gcguguucug ccucguguua cucugggagg ugggcgccgc cagccuuagc     120
gaggugaagc uccacuugga caucgagggc cacgccagcc acuacaccau ccccuggacc     180
gagcucaugg ccaaggugcc cggccuuagc cccgaggccc uguggcggga ggccaacgug     240
accgaggacc uggccagcau gcugaaccgg uacaagcuga ucuacaagac cagcggcacc     300
cugggcaucg cccuggccga gcccguggac auccccgccg uuagcgaagg cagcaugcag     360
guggacgcca gcaaggugca ccccggcgug aucagcggcc ugaacagccc cgccuguaug     420
uugagcgccc cacuggagaa gcagcuguuc uacuacaucg gcaccaugcu gcccaacacc     480
cggccccaca gcuacguguu cuaccagcug cggugccacc ugagcuacgu ugcccugagc     540
aucaacggcg acaaguucca guacaccggc gccaugacca gcaaguuccu gaugggcacc     600
uacaagcggg ucaccgagaa gggcgacgag cacgugcugu cacugguguu cggcaagacc     660
aaggaccugc ccgaccugcg gggccccuuc agcuacccua guuugaccag cgcccagagc     720
ggcgacuaca gcuuggugau cgugaccacc uucgugcacu acgccaacuu ccacaacuac     780
uucgugccca accugaagga cauguucagc cgggccguga ccaugacugc cgcuucuuac     840
gcccgguacg ugcugcagaa gcugguccug cuggagauga agggcggcug ccgggagccc     900
gagcuggaca ccgaaacacu gaccaccaug uucgagguga gcguggccuu cuucaaggug     960
ggucacgcgg ugggcgaaac cggcaacggc ugcguggacu uacgcuggcu ggccaagagc    1020
uucuucgagc ugaccgugcu gaaggauauc aucggcaucu gcuacggcgc caccgugaag    1080
ggcaugcaga gcuacggccu ggagcggcug gccgccaugc uuauggcaac agugaagaug    1140
gaggagcugg gacaccugac aacagagaag caggaguacg cccugagacu ggccacagug    1200
ggcuacccaa aggccggcgu guacagugga cugaucggcg gcgcaaccag cgugcugcua    1260
uccgcuuaca accggcaccc gcuguuccag ccccugcaca ccgugaugcg ggaaacccug    1320
uucaucggaa gccacgucgu gcugcgggag cugaggcuga acguaaccac ccagggcccu    1380
aaucuggccc uguaucagcu ccucaguacc gcccugugca gcgcccuuga gaucggcgag    1440
gugcucagag gccuggcccu cgguaccgag agcggccucu ucagcccaug cuacuuaagc    1500
cugcgguucg accugacccg ggacaaguug cugagcaugg ccccgcagga ggccacacug    1560
gaccaggcag cuguauccaa cgccguggac ggcuuccugg gcagacuguc ccuggaacgg    1620
gaggaccggg acgccuggca ccugccugcc uacaagugug uggaucggcu ggacaaggug    1680
cugaugauca ucccucugau uaaugucacc uucaucauca gcagcgaccg ggaggugcgg    1740
ggauccgccc ucuacgaggc cagcaccacc uaucugagca gcagccuguu ccugucuccu    1800
gugaucauga acaagugcag ccagggcgcc guggccggcg agccccggca gauccccaag    1860
auccagaacu ucacccggac ccagaagucu ugcaucuucu gcggcuucgc ccuuuugucc    1920
uacgacgaga aggagggcuu ggagacuaca accuacauca ccagccagga ggugcagaac    1980
agcauccugu caucuaauua cuucgacuuc gacaaccugc acguucauua ccugcuccuc    2040
accaccaacg guaccgucau ggaaaucgcc ggacuguacg aggagcgggc ccauguugug    2100
cuggccauca uccuguacuu caucgcuuuc gcacuuggca ucuuccuggu gcacaagauc    2160
gugauguucu uccugugaua auaggcugga gccucggugg ccuagcuucu ugccccuugg    2220
gccucccccc agccccuccu ccccuuccug cacccguacc cccgugguuu uugaauaaag    2280
ucugaguggg cggc                                                     2294
```

<210> SEQ ID NO 19
<211> LENGTH: 587
<212> TYPE: RNA
<213> ORGANISM: Artificial Sequence
<220> FEATURE:
<223> OTHER INFORMATION: Synthetic

<400> SEQUENCE: 19
gggaaauaag agagaaaaga agaguaagaa gaaauauaag accccggcgc cgccaccaug 60
agagccgugg gcguguuccu ggccaucugc cuggugacca ucuucgugcu gcccaccugg 120
ggcaacuggg ccuaccccug cugccacgug acccagcuga gagcccagca ccugcuggcc 180
cuggagaaca ucagcgacau cuaccuggug agcaaccaga ccugcgacgg cuucagccug 240
gccagccuga acagccccaa gaacggcagc aaccagcugg ugaucagcag augcgccaac 300
ggccugaacg uggugagcuu cuucaucagc auccugaaga gaagcagcag cgcccugacc 360
ggccaccuga gagagcugcu gaccacccug gagacccugu acggcagcuu cagcguggag 420
gaccuguucg gcgccaaccu gaacagauac gccuggcaca gaggcggcug auaauaggcu 480
ggagccucgg uggccuagcu ucuugccccu ugggccuccc cccagccccu ccuccccuuc 540
cugcacccgu acccccgugg ucuuugaaua aagucugagu gggcggc 587

<210> SEQ ID NO 20
<211> LENGTH: 788
<212> TYPE: RNA
<213> ORGANISM: Artificial Sequence
<220> FEATURE:
<223> OTHER INFORMATION: Synthetic

<400> SEQUENCE: 20
gggaaauaag agagaaaaga agaguaagaa gaaauauaag accccggcgc cgccaccaug 60
acccggcggc ggguguuaag cgugguggug cucuuagccg ccuuagccug ccggcuuggc 120
gccaucaccu gggugcccaa gcccaacgug gaggugugge ccguggaccc gccaccuccc 180
gugaacuuca acaagaccgc cgagcaggag uacggcgaca aggaggugaa gcugccccac 240
uggacgccga cccugcacac cuuccaggug ccccagaacu acaccaaggc caacugcacc 300
uacugcaaca ccagagagua caccuucagc uacaagggcu gcugcuucua cuucaccaag 360
aagaagcaca ccuggaacgg cugcuuccag gccugcgccg agcuguaccc cugcaccuac 420
uucuacggcc ccaccccaga cauccugccc guggugacca gaaaccugaa cgccaucgag 480
agccuguggg ugggcgugua cagagugggc gagggcaacu ggaccagccu ggacggcggc 540
accuucaagg uguaccagau cuucggcagc cacugcaccu acgugagcaa guucagcacc 600
gugcccguga gccaccacga gugcagcuuc cugaagcccu gccugugcgu gagccagaga 660
agcaacagcu gauaauaggc uggagccucg guggccuagc uucuugcccc uugggccucc 720
ccccagcccc uccuccccuu ccugcacccg uacccccgug gucuuugaau aaagucugag 780
ugggcggc 788

<210> SEQ ID NO 21
<211> LENGTH: 2747
<212> TYPE: RNA
<213> ORGANISM: Artificial Sequence
<220> FEATURE:
<223> OTHER INFORMATION: Synthetic

<400> SEQUENCE: 21

-continued

```
gggaaauaag agagaaaaga agaguaagaa gaaauauaag accccggcgc cgccaccaug     60
acccggcggc ggguguuaag cgugguggug cucuuagccg ccuuagccug ccggcuuggc    120
gcccagacuc cggagcagcc cgcuccuccc gccaccaccg uccagcccac cgccacccgc    180
cagcagaccu ccuuccccuu ccgcgucugc gagcucuccu cccacggcga ccucuuccgc    240
uucuccuccg acauccagug ccccuccuuc ggcacccgcg agaaccacac cgagggccuc    300
cucaugggucu ucaaggacaa caucaucccc uacuccuuca agguccgcuc cuacaccaag    360
aucgucacca acauccucau cuacaacggc ugguacgccg acucugugac uaaucgccac    420
gaggagaagu ucuccgucga cuccuacgag acugaccaga uggacaccau cuaccagugc    480
uacaacgccg ucaagaugac caaggacggc cucacccgcg ucuacgucga ccgcgacggc    540
gucaacauca ccgucaaccu caagccuaca ggcggccucg ccaacggcgu ccgccgcuac    600
gccucccaga ccgagcucua cgacgccccu ggcuggcuca ucuggaccua ccgcaccagg    660
accacuguca auugccucau caccgacaug auggccaagu ccaacucccc uuucgacuuc    720
uucgugacca ccacaggcca gaccgucgag augucgccau ucuaugacgg caagaacaag    780
gagacuuucc acgagagagc ggacucuuuc cauguccgca ccaacuacaa gauugucgac    840
uacgacaacc gcggcaccaa uccacagggc gagcgccgcg ccuuccucga caagggcacc    900
uacacccucu ccuggaagcu cgagaaccgc accgccuacu guccucucca gcacuggcag    960
accuucgauu ccaccaucgc caccgagacu ggcaagucca uccauuucgu caccgacgaa   1020
ggaacaucuu cauucgucac aaauacaacc gugggcaucg agcuccccga cgccuucaag   1080
ugcaucgagg agcaggucaa caagaccaug cacgagaagu acgaggccgu ccaggaccgg   1140
uauacaaagg gccaggaggc caucaccuac uucaucacca gcggaggucu gcuucucgcc   1200
uggcuuccac ucacaccucg cucccuggcc acagugaaga accucacuga guugaccacc   1260
ccaacaaguu ccccaccuag uaguccuagc ccuccugcuc cuuccgccgc ccgcggcucc   1320
acgccugccg ccguccugcg gagacggaga agggacgccg gcaacgcuac cacuccugug   1380
ccgccgacag ccccuggaaa gucccuaggu acccucaaca acccagcgac aguucagauc   1440
caguucgccu acgacucucu caggcgccag aucaaccgca ugcuugguga ccuugcccgc   1500
gccuggugcc ucgagcagaa gcgccagaac auggugcuuc gugaacuaac aaagauuaau   1560
ccuacuacag ugauguccuc caucuacggc aaggccgucg ccgccaagcg ccucggcgac   1620
gucaucuccg ucucccagug cgucccagug aaccaggcua ccgugacccu caggaagucc   1680
augagagugc caggcuccga gacaaugugc uacucccgcc cacucgucuc cuucuccuuc   1740
aucaacgaca caaagaccua cgagggccag uuaggcacug acaacgagau cuucuugacu   1800
aagaagauga cugagguaug ccaggcaacu ucucaauacu acuuccaguc uggaaaugag   1860
auccacguau auaacgacua ccaccacuuc aagacuauug aacucgacgg aauugccacc   1920
cuccaaacau ucaucucacu gaauaccucc cucaucgaga acaucgacuu cgccucccuc   1980
gagcuguaua gcagagacga gcagcgcgcc uccaacgucu ucgaccucga gggcaucuuc   2040
cgcgaguaca acuuccaggc acagaacaua gccggccucc guaaggaucu ggacaaugcc   2100
guguccaacg gccgcaacca guucgucgac gguuugggug aacucaugga cucucugggc   2160
uccgucggcc aguccauaac uaacuuaguc ucuacggugg gaggccuauu cagcagccug   2220
gugagcggcu ucaucucuuu cuucaagaac cccuucggcg gcaugcucau ccucguccuc   2280
gucgccggcg ucgucauacu ggugaucuca cucacaagga ggacgcgcca aaugucccag   2340
cagccagugc agaugcucua cccaggcaua gacgagcucg cucagcagca cgcgucgggu   2400
```

gagggaccag gcaucaaucc uaucuccaag acugagcugc aagccauuau gcucgcccuc 2460
cacgagcaga accaggaaca gaagcgggcc gcccagcgag cugccggccc cuccgucgcc 2520
aguagggcac uacaagccgc ccgggaccgc uucccaggcc ugagaaggag gagauaccac 2580
gacccagaga cagccgcugc ccuccuuggc gaagcagaaa ccgaguucug auaauaggcu 2640
ggagccucgg uggccuagcu ucuugccccu ugggccuccc cccagccccu ccucccccuuc 2700 cugcacccgu accccccgugg ucuuugaaua aagucugagu gggcggc 2747

<210> SEQ ID NO 22
<211> LENGTH: 845
<212> TYPE: RNA
<213> ORGANISM: Artificial Sequence
<220> FEATURE:
<223> OTHER INFORMATION: Synthetic

<400> SEQUENCE: 22
gggaaauaag agagaaaaga agaguaagaa gaaauauaag accccggcgc cgccaccaug 60
gugagcuuca agcaggugag agugccccug uucaccgcca ucgcccuggu gaucgugcug 120
cugcuggccu acuuccugcc acccagagug agaggcggcg gcagaguggc cgccgccgcc 180
aucaccuggg ugcccaagcc caacguggag guguggcccg uggacccgcc accucccgug 240
aacuucaaca agaccgccga gcaggaguac ggcgacaagg aggugaagcu gccccacugg 300
acgccgaccc ugcacaccuu ccaggugccc cagaacuaca ccaaggccaa cugcaccuac 360
ugcaacacca gagaguacac cuucagcuac aagggcugcu gcuucuacuu caccaagaag 420
aagcacaccu ggaacggcug cuuccaggcc ugcgccgagc uguaccccug caccuacuuc 480
uacggcccca ccccagacau ccugcccgug gugaccagaa accugaacgc caucgagagc 540
cugugggugg gcguguacag agugggcgag ggcaacugga ccagccugga cggcggcacc 600
uucaaggugu accagaucuu cggcagccac ugcaccuacg ugagcaaguu cagcaccgug 660
cccgugagcc accacgagug cagcuuccug aagcccugcc ugugcgugag ccagagaagc 720
aacagcugau aauaggcugg agccucggug gccuagcuuc uugccccuug ggccuccccc 780
cagccccucc uccccuuccu gcacccguac ccccgugguc uuugaauaaa gucugagugg 840
gcggc 845

<210> SEQ ID NO 23
<211> LENGTH: 2771
<212> TYPE: RNA
<213> ORGANISM: Artificial Sequence
<220> FEATURE:
<223> OTHER INFORMATION: Synthetic

<400> SEQUENCE: 23
gggaaauaag agagaaaaga agaguaagaa gaaauauaag accccggcgc cgccaccaug 60
gaggcagcac ugcuggucug ccaguauaca auccagucgc ucauucaucu gacaggcgag 120
gaccccggcu ucuuuaacgu ggaaauccca gaguucccuu ucuauccaac cuguaacguu 180
ugcacugcug acgugaacgu gacaaucaau uucgacgugg gaggaaagaa gcaucagcuu 240
gaucuggauu ucggccaacu gacgccacac accaaagcgg uguaccaacc aaggggugca 300
uuuggaggga gcgagaaugc uacaaaucug uucuuacugg aacugcuugg ugcaggagag 360
cuggcacuaa ccaugcgaag caagaagcuc cccaucaacg uuaccaccgg ggaagaacag 420
caagucagcc uugaauccgu ggauguguac uuucaggaug uuuucggcac cauguggugu 480

-continued

```
caccacgcug agaugcagaa ucccguguau cucauacccg agacuguacc cuacaucaag    540
ugggauaauu gcaauucaac uaauauuacg gcuguggugga gggcccaggg cuuggacgug   600
acucugcccu uaucucuacc uacuucugcc caagacucca auuucucugu caagaccgag    660
augcucggga augagaucga uaucgagugc aucauggagg acggugagau aagccagguu    720
cugcccggcg acaacaaguu caauaucacu uguucuggcu acgaguccca ugugccuagu    780
gguggcauac ucacaaguac uucucccgua gccacgccca uucccggaac cggauacgcc    840
uacagucugc gucugacccc acggccugug uccagauucc uggguaacaa uaguaucuua    900
uacguguuuu auagcggaaa cggcccuaaa gcguccggag gggacuauug uauucagagu    960
aauaucguuu ucucugauga gauuccugcc agucaggaca ugccgacaaa cacaacugau   1020
auuaccuacg ugggcgacaa ugccacguau ucagugccca uggucacgag cgaggacgcc   1080
aauucaccaa auguuacugu aacagcuuuc ugggccuggc caaauaacac ugagacugac   1140
uucaaaugua aguggacuuu gaccucugga acuccgucgg guugcgagaa uaucagcggg   1200
gccuuugcuu ccaacaggac uuucgacauc acugucucag ggcuggggac agcaccgaag   1260
acauuaauca uaacacggac cgccaccaac gccacgacua caacccauaa ggugaucuuu   1320
uccaaggcac cugaguccac cacuaccucc ccgacucuua acacuacggg cuucgcugau   1380
cccaacacca cuacgggguu gccuagcucg acacaugugc cgacgaaccu gacugccccu   1440
gcaucgaccg ggcccacagu uucgaccgcc gaugugacau caccaacgcc cgcagguaca   1500
accucaggcg ccagcccagu gaccccuucc ccaagccccu gggauaaugg aacggagucc   1560
aaggcuccug auaugacuuc cucuaccagc cccgugacua cacccacucc caacgcaacu   1620
agcccaaccc cagcugugac gacgcccacc ccgaacgcga caucucccac accugcugug   1680
acaaccccaa ccccuaacgc cacuagcccu acccuaggua agaccagucc gacuagcgcc   1740
guuacaaccc cuaccccuaa cgcaaccggc ccgaccgugg gcgagacuuc cccgcaagcc   1800
aaugcgacaa aucacacauu gggcgggacc ucuccuacac cagucguuac aucucagccu   1860
aagaacgcua ccuccgcugu cacuaccgga cagcacaaca ucaccagcuc aagcacgagu   1920
uccaugagcu ugcggccgag cucaaauccc gagacccuau caccauccac aucagacaac   1980
aguacuucac acaugccacu cuugacgagc gcucacccca ccggcggcga gaacaucacc   2040
caggugacuc cggcgucuau uuccacccac cacgucagca cgucgucucc cgcaccgaga   2100
ccagggacga cuucucaggc caguggggccu ggcaacuccu cuacaagcac aaagccaggc   2160
gaaguuaacg ugacaaaggg aacgccuccc cagaacgcaa ccaguccuca ggcgcccagc   2220
gggcagaaga cugcggugcc aacugugacc agcaccggug gcaaggccaa cucaacaacu   2280
ggaggcaagc auacgacggg gcacggcgcc cggaccucca cugaacccac gaccgauuac   2340
ggaggugaca gcacaacacc gcggccacga uauaaugcca ccacuuaucu gccaccaucc   2400
acaagcucca agcugcggcc acgguggacc uucacaagcc cacccgugac gacugcccaa   2460
gcgacggugc cagugccacc uacaagccag ccacgcuucu ccaaccuuag uaugcucguu   2520
cuccaguggg ccagccuugc uguucugacc cuccuccugc ugcucgugau ggccgauugc   2580
gccuuuagga gaaaccucag cacuagccac acguacacca cgccgcccua cgaugacgcc   2640
gagacuuacg ucugauaaua ggcuggagcc ucgguggccu agcuucuugc cccuugggcc   2700
uccccccagc cccuccuccc cuuccugcac ccguaccccc guggucuuug aauaaagucu   2760
gaguggggcgg c                                                        2771
```

-continued

<210> SEQ ID NO 24
<211> LENGTH: 47
<212> TYPE: RNA
<213> ORGANISM: Artificial Sequence
<220> FEATURE:
<223> OTHER INFORMATION: Synthetic

<400> SEQUENCE: 24
gggaaauaag agagaaaaga agaguaagaa gaaauauaag agccacc 47

<210> SEQ ID NO 25
<211> LENGTH: 119
<212> TYPE: RNA
<213> ORGANISM: Artificial Sequence
<220> FEATURE:
<223> OTHER INFORMATION: Synthetic

<400> SEQUENCE: 25
ugauaauagg cuggagccuc gguggccaug cuucuugccc cuugggccuc cccccagccc 60
cuccuccccu uccugcaccc guacccccgu ggucuuugaa uaaagucuga gugggcggc 119

<210> SEQ ID NO 26
<211> LENGTH: 30
<212> TYPE: PRT
<213> ORGANISM: Artificial Sequence
<220> FEATURE:
<223> OTHER INFORMATION: Synthetic

<400> SEQUENCE: 26

Met Asp Ser Lys Gly Ser Ser Gln Lys Gly Ser Arg Leu Leu Leu Leu
1 5 10 15

Leu Val Val Ser Asn Leu Leu Leu Pro Gln Gly Val Val Gly
20 25 30

<210> SEQ ID NO 27
<211> LENGTH: 18
<212> TYPE: PRT
<213> ORGANISM: Artificial Sequence
<220> FEATURE:
<223> OTHER INFORMATION: Synthetic

<400> SEQUENCE: 27

Met Asp Trp Thr Trp Ile Leu Phe Leu Val Ala Ala Ala Thr Arg Val
1 5 10 15

His Ser

<210> SEQ ID NO 28
<211> LENGTH: 20
<212> TYPE: PRT
<213> ORGANISM: Artificial Sequence
<220> FEATURE:
<223> OTHER INFORMATION: Synthetic

<400> SEQUENCE: 28

Met Glu Thr Pro Ala Gln Leu Leu Phe Leu Leu Leu Leu Trp Leu Pro
1 5 10 15

Asp Thr Thr Gly
20

<210> SEQ ID NO 29
<211> LENGTH: 24
<212> TYPE: PRT
<213> ORGANISM: Artificial Sequence
<220> FEATURE:
<223> OTHER INFORMATION: Synthetic

<400> SEQUENCE: 29

Met Leu Gly Ser Asn Ser Gly Gln Arg Val Val Phe Thr Ile Leu Leu
1 5 10 15

Leu Leu Val Ala Pro Ala Tyr Ser
20

<210> SEQ ID NO 30
<211> LENGTH: 17
<212> TYPE: PRT
<213> ORGANISM: Artificial Sequence
<220> FEATURE:
<223> OTHER INFORMATION: Synthetic

<400> SEQUENCE: 30

Met Lys Cys Leu Leu Tyr Leu Ala Phe Leu Phe Ile Gly Val Asn Cys
1 5 10 15

Ala

<210> SEQ ID NO 31
<211> LENGTH: 15
<212> TYPE: PRT
<213> ORGANISM: Artificial Sequence
<220> FEATURE:
<223> OTHER INFORMATION: Synthetic

<400> SEQUENCE: 31

Met Trp Leu Val Ser Leu Ala Ile Val Thr Ala Cys Ala Gly Ala
1 5 10 15

<210> SEQ ID NO 32
<211> LENGTH: 9
<212> TYPE: RNA
<213> ORGANISM: Artificial Sequence
<220> FEATURE:
<223> OTHER INFORMATION: Synthetic

<400> SEQUENCE: 32 uuauuuaww 9

<210> SEQ ID NO 33
<211> LENGTH: 9
<212> TYPE: RNA
<213> ORGANISM: Artificial Sequence
<220> FEATURE:
<223> OTHER INFORMATION: Synthetic

<400> SEQUENCE: 33 ccrccaugg 9

<210> SEQ ID NO 34
<211> LENGTH: 11
<212> TYPE: RNA
<213> ORGANISM: Artificial Sequence
<220> FEATURE:
<223> OTHER INFORMATION: Synthetic

<400> SEQUENCE: 34
gggauccuac c 11